US006890731B1

(12) United States Patent
Kodira et al.

(10) Patent No.: US 6,890,731 B1
(45) Date of Patent: May 10, 2005

(54) ISOLATED HUMAN G-PROTEIN COUPLED RECEPTORS THAT ARE MEMBERS OF THE AMINERGIC SUBFAMILY, NUCLEIC ACID MOLECULES ENCODING HUMAN GPCR PROTEINS, AND USES THEREOF

(75) Inventors: Chinnappa Kodira, Germantown, MD (US); Anibal Cravchik, Gaithersburg, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/633,145

(22) Filed: Aug. 4, 2000

Related U.S. Application Data

(60) Provisional application No. 60/192,311, filed on Mar. 27, 2000.

(51) Int. Cl.[7] ........................ C12N 15/00; C12N 15/63; C12N 15/85; C07H 21/04; C07K 5/00

(52) U.S. Cl. .................... 435/69.1; 536/23.1; 536/23.5; 435/6; 435/325; 435/252.3; 435/320.1; 530/350

(58) Field of Search ............................ 435/69.1, 320.1, 435/325, 252.3, 254.11; 536/23.5, 24.3; 530/350

(56) References Cited

PUBLICATIONS

Borowsky, et al, 2001, Proc. Natl. Acad. Sci., 98(16): 8966–8971.*
Bunzow, et al, 2001, Mol. Pharmacol., 60(6): 1181–1188.*
Bunzow, et al 2001, Mol. Pharmacol., 60: 1181–1188.*
Bunzow, et al, 2003, Accession No. NM_138327.*
Ji, et al, 1998, J. Biol. Chem., 273(28): 17299–17302.*
Sucher, N.J., 1999, Accession No. T31068.*
Skolnick et al., 2000, Trends in Biotech. 18:34–39.*
Bork, P., 2000, Genome Research 10:398–400.*
Doerks et al., 1998, Trends in Genetics 14:248–250.*
Smith et al., 1997, Nature Biotechnology 15:1222–1223.*
Brenner. S., 1999, Trends in Genetics 15:132–133.*
Bork et al., 1996, Trends in Genetics 12:425–427.*
Borowsky, et al, 2001, PNAS, 98(16): 8966–8971, esp. Table 1.*
Bunzow, et al, 2001, Mol. Pharmacol. 60: 1181–1188.*
Kim, et al, 2001, Mol. Pharmacol. 60: 1165–1167.*
Lee, et al, 2000, Accession No. AF112460.*
Lee, et al, 2000, Accession No. AF112461.*
Federal Register, 2001, 66: 1094–1099.*
Ji, et al, 1998, p. 17299–17302, 3rd paragraph.*
Probst, W.C.,et al, 1992, DNA and Cell Biol., 11(1):1–20.*
Ji, et al, 1998, J. Biol. Chem., 273:17299–17302.*
Bunzow et al. "Amphetamine, 3,4–Methylenediozymethamphetamine, Lysergic Acid Diethylamide, and Metabolites of the Catecholamine Neurotransmitters Are Agonists of a Rat Trace Amine Receptor": Mol Pharmacol 60:1181–1188, 2001.
Kim et al., "Old Drugs Learn New Tricks: Insights from Mammalian Trace Amine Receptors": Mol Pharmacol 60: 1165–1167, 2001.

(Continued)

*Primary Examiner*—Elizabeth Kemmerer
*Assistant Examiner*—Sandra Wegert
(74) *Attorney, Agent, or Firm*—Celera Genomics; Lin Sun-Hoffman

(57) ABSTRACT

The present invention provides amino acid sequences of peptides that are encoded by genes within the Human genome, the GPCR peptides of the present invention. The present invention specifically provides isolated peptide and nucleic acid molecules, methods of identifying orthologs and paralogs of the GPCR peptides and methods of identifying modulators of the GPCR peptides.

11 Claims, 35 Drawing Sheets

OTHER PUBLICATIONS

Borowsky et al. "Trace Amines: Identification of a Family of Mammalian G Protein—Coupled Receptors": PNAS 98 8966–8961, 2001.

WO 00/73449 A (Obozalek Kristine L; Borowsky Beth E [US]; Jones Kenneth A [US]; S): Dec. 7, 2000: Figures 5, 6.

EP 0 859 055 A (Smithkline Beecham Corp) Aug. 19, 1998: the whole document.

Lee D K et al.: "Cloning and characterization of additional members of the G Protein–Coupled Receptor Family": Biuochimica et biophysica acta. Gene structure and Expression, Elsevier, Amsterdam, NL: vol. 1490 No. 3: Feb. 29, 2000: pp. 311–333.

Hoyer D et al.: "VII. International Union of Pharmacology Classification of Receptors for 5–Hydroxytryptamine (Serotonin)": Pharmacological Reviews, Williams and Wilkins, Inc., Baltimore, MD, US: vol. 46, No. 2: Jun. 1, 1994: pp. 157–203.

* cited by examiner

```
   1 AAAATAACGA AAGAAAGGCA GAGAGGAAGT AGCGAGAGAA GAGAGAAAAT
  51 GAAGTCGGCG CTGGGGGAGC CTGCAGGAGG GTGGCCAACA GTGGAGGAAG
 101 GTGGATTTGG CTTCTTTTCC GCACCCCGGG CGTGAAAGCC CTCTCCAACG
 151 CGACCCCAGG AAATAAGTGG GTCTCGCCTG GGCAGAAAAG GAAAAGAATC
 201 CAGGCGAGAG CGCGTCGCTC CTCTGTCACT GCTGCCCCCG AGGAACTCCG
 251 GCTGCTTCTC ATCCCGGCCG CCTCGCGGGG CCGGACGCAG TGCCCGAGGC
 301 GCCCTGCAGA TGGGGCGGGC AGGGAACGGG CGCTCCAGCT GCGGGTGACA
 351 GGCGCCGGCC CGCCCGCCTG CCTGCTCAGC GCAGTGACCG GGCGGGCAGA
 401 GGATGCCAGG CGGAGGGACC TGGGAGCGGG ATCTGAGACT GCCGGAGGCG
 451 CGCTACGCTC CAACTTGCAT GGCCTAGAGA CCGCTCCAGC TCCTGGGACC
 501 GCTTCACCGA GTGGAGTGAA GCTGCGCGCG GGACCTGGAG GCGGAGACCT
 551 CAGGCAGCGG CTGCAGAGGG GCGAGCCGGG CGCAGGAGGG GGCGCGCTTT
 601 CTCCCTGCGG GTCTCAGTAA TGAGGAGACT GAGTTTGTGG TGGCTGCTGA
 651 GCAGGGTCTG TCTGCTGTTG CCGCCGCCCT GCGCACTGGT GCTGGCCGGG
 701 GTGCCCAGCT CCTCCTCGCA CCCGCAGCCC TGCCAGATCC TCAAGCGCAT
 751 CGGGCACGCG GTGAGGGTGG GCGCGGTGCA CTTGCAGCCC TGGACCACCG
 801 CCCCCCGCGC GGCCAGCCGC GCTCCGGACG ACAGCCGAGC AGGAGCCCAG
 851 AGGGATGAGC CGGAGCCAGG GACTAGGCGG TCCCCGGCGC CCTCGCCGGG
 901 CGCACGCTGG TTTGGGAGCA CCCTGCATGG CCGGGGGCCG CCGGGCTCCC
 951 GTAAGCCCGG GGAGGGCGCC AGGGCGGAGG CCCTGTGGCC ACGGGACGCC
1001 CTCCTATTTG CCGTGGACAA CCTGAACCGC GTGGAAGGGC TGCTACCCTA
1051 CAACCTGTCT TTGGAAGTAG TGATGGCCAT CGAGGCAGGC CTGGGCGATC
1101 TGCCACTTTT GCCCTTCTCC TCCCCTAGTT CGCCATGGAG CAGTGACCCT
1151 TTCTCCTTCC TGCAAAGTGT GTGCCATACC GTGGTGGTGC AAGGGGTGTC
1201 GGCGCTGCTC GCCTTCCCCC AGAGCCAGGG CGAAATGATG GAGCTCGACT
1251 TGGTCAGCTT AGTCCTGCAC ATTCCAGTGA TCAGCATCGT GCGCCACGAG
1301 TTTCCGCGGG AGAGTCAGAA TCCCCTTCAC CTACAACTGA GTTTAGAAAA
1351 TTCATTAAGT TCTGATGCTG ATGTCACTGT CTCAATCCTG ACCATGAACA
1401 ACTGGTACAA TTTTAGCTTG TTGCTGTGCC AGGAAGACTG GAACATCACC
1451 GACTTCCTCC TCCTTACCCA GAATAATTCC AAGTTCCACC TTGGTTCTAT
1501 CATCAACATC ACCGCTAACC TCCCCTCCAC CCAGGACCTC TTGAGCTTCC
1551 TACAGATCCA GCTTGAGAGT ATTAAGAACA GCACACCCAC AGTGGTGATG
1601 TTTGGCTGCG ACATGGAAAG TATCCGGCGG ATTTTCGAAA TTACAACCCA
1651 GTTTGGGGTC ATGCCCCCTG AACTTCGTTG GGTGCTGGGA GATTCCCAGA
1701 ATATGGAGGA ACTGAGGACA GAGGGTCTGC CCTTAGGACT CATTGCTCAT
1751 GGAAAAAACAA CACAGTCTGT CTTTGAGCAC TACGTACAAG ATGCTATGGA
1801 GCTGGTCGCA AGAGCTGTAG CCACAGCCAC CATGATCCAA CCAGAACTTG
1851 CTCTCATTCC CAGCACGATG AACTGCATGG AGGTGGAAAC TACAAATCTC
1901 ACTTCAGGAC AATATTTATC AAGGTTTCTA GCCAATACCA CTTTCAGAGG
1951 CCTCAGTGGT TCCATCAGAG TAAAAGGTTC CACCATCGTC AGCTCAGAAA
2001 ACAACTTTTT CATCTGGAAT CTTCAACATG ACCCCATGGG AAAGCCAATG
2051 TGGACCCGCT TGGGCAGCTG GCAGGGGAGA AAGATTGTCA TGGACTATGG
2101 AATATGGCCA GAGCAGGCCC AGAGACACAA AACCCACTTC CAACATCCAA
2151 GTAAGCTACA CTTGAGAGTG GTTACCCTGA TTGAGCATCC TTTTGTCTTC
2201 ACAAGGGAGG TAGATGATGA AGGCTTGTGC CCTGCTGGCC AACTCTGTCT
2251 AGACCCCATG ACTAATGACT CTTCCACACT GGACAGCCTT TTTAGCAGCC
2301 TCCATAGCAG TAATGATACA GTGCCCATTA AATTCAAGAA GTGCTGCTAT
2351 GGATATTGCA TTGATCTGCT GGAAAAGATA GCAGAAGACA TGAACTTTGA
2401 CTTCGACCTC TATATTGTAG GGGATGGAAA GTATGGAGCC TGGAAAAATG
2451 GGCACTGGAC TGGGCTAGTG GGTGATCTCC TGAGAGGGAC TGCCCACATG
2501 GCAGTCACTT CCTTTAGCAT CAATACTGCA CGGAGCCAGG TGATAGATTT
2551 CACCAGCCCT TTCTTCTCCA CCAGCTTGGG CATCTTAGTG AGGACCCGAG
2601 ATACAGCAGC TCCCATTGGA GCCTTCATGT GGCCACTCCA CTGGACAATG
2651 TGGCTGGGGA TTTTTGTGGC TCTGCACATC ACTGCCGTCT TCCTCACTCT
2701 GTATGAATGG AAGAGTCCAT TTGGTTTGAC TCCCAAGGGG CGAAATAGAA
2751 GTAAAGTCTT CTCCTTTTCT TCAGCCTTGA ACATCTGTTA TGCCCTCTTG
2801 TTTGGCAGAA CAGTGGCCAT CAAACCTCCA AAATGTTGGA CTGGAAGGTT
2851 TCTAATGAAC CTTTGGGCCA TTTTCTGTAT GTTTTGCCTT TCCACATACA
2901 CGGCAAACTT GGCTGCTGTC ATGGTAGGTG AGAAGATCTA TGAAGAGCTT
2951 TCTGGAATAC ATGACCCCAA GTTACATCAT CCTTCCCAAG GATTCCGCTT
3001 TGGAACTGTC CGAGAAAGCA GTGCTGAAGA TTATGTGAGA CAAAGTTTCC
3051 CAGAGATGCA TGAATATATG AGAAGGTACA ATGTTCCAGC CACCCCTGAT
3101 GGAGTGGAGT ATCTGAAGAA CAATCCAGAG AAACTAGACG CCTTCATCAT
```

FIGURE 1, page 1 of 4

```
3151 GGACAAAGCC CTTCTGGATT ATGAAGTGTC AATAGATGCT GACTGCAAAC
3201 TTCTCACTGT GGGGAAGCCA TTTGCCATAG AAGGATACGG CATTGGCCTC
3251 CCACCCAACT CTCCATTGAC CGCCAACATA TCCGAGCTAA TCAGTCAATA
3301 CAAGTCACAT GGGTTTATGG ATATGCTCCA TGACAAGTGG TACAGGGTGG
3351 TTCCCTGTGG CAAGAGAAGT TTTGCTGTCA CGGAGACTTT GCAAATGGGC
3401 ATCAAACACT TCTCTGGGCT CTTTGTGCTG CTGTGCATTG GATTTGGTCT
3451 GTCCATTTTG ACCACCATTG GTGAGCACAT AGTATACAGG CTGCTGCTAC
3501 CACGAATCAA AAACAAATCC AAGCTGCAAT ACTGGCTCCA CACCAGCCAG
3551 AGATTACACA GAGCAATAAA TACATCATTT ATAGAGGAAA AGCAGCAGCA
3601 TTTCAAGACC AAACGTGTGG AAAAGAGGTC TAATGTGGGA CCCCGTCAGC
3651 TTACCGTATG GAATACTTCC AATCTGAGTC ATGACAACCG ACGGAAATAC
3701 ATCTTTAGTG ATGAGGAAGG ACAAAACCAG CTGGGCATCC GGATCCACCA
3751 GGACATCCCC CTCCCTCCAA GGAGAAGAGA GCTCCCTGCC TTGCGGACCA
3801 CCAATGGGAA AGCAGACTCC CTAAATGTAT CTCGGAACTC AGTGATGCAG
3851 GAACTCTCAG AGCTCGAGAA GCAGATTCAG GTGATCCGTC AGGAGCTGCA
3901 GCTGGCTGTG AGCAGGAAAA CGGAGCTGGA GGAGTATCAA AGGACAAGTC
3951 GGACTTGTGA GTCCTAGGTG ACCACACTGC TTCCCTTTCT CAGTTCCTGA
4001 CCTTCCTCTG AGCCCTTGAG ACACTTTGTA ATGCTCTTTT GTAACTATCG
4051 ACAAAGGTGT GGGGAAGCTG AGGTCTAGGT CTTCTTAAAG GTCAAGTCTG
4101 CTCTCCCTCG CCTAAAGTGC AGCAGCAGCT CCTCTCAAGC TCACTCTCTA
4151 GGTCTCCAGG GTAGGAGTGT TTTTCTAGCA AGAATCTTAG TCAGGAGTAA
4201 GCTCTGTGCG AGAGATCTGT GAATAACCAG ATAACCCCAG CTGCCGTTAA
4251 CCTTTTCACC AGGTGCCACA GTAATATTTC TGGTTTTTAG CCCTTTCTCT
4301 GCACTACCAA CAAGAGATAA AATTGTTACT CACACTTATG TCTTACTGGG
4351 TTGCTGGTTT TCATCGTAAC ACAGAACGAG GTTATCTAGG GTTGTAGCTT
4401 TTGATACAAC TCCCCGATCT AGATTTATTC CTACATTCTG AATGGGGAGC
4451 AGGTAAGAGC AGAGCACCTC CCACTGGGGG TGGGGTATTT AAAAATTAAC
4501 TCATTAGTAT CATAAACGTC AAGGATTGAT TGGACCAGGC AAGAGCCATG
4551 TTTTTGAGAA GGTTCTGGAT CTCTGACTCC ATCCTGACTG TTTAGTAAGA
4601 GCATGCTTAC ACCCTACTGT GAAAAGGGGA GGGGATGTGG TAAGCGGAAA
4651 CAGAAGACAG GCAGCAGAGG CATTAAAAAT GCATACCATG CTTTCAGAAC
4701 AAAAGCTCTG GGCCAGAAAG GCAATTTGGC TAAAAAATGA ATAAGACTAC
4751 TTCTAATGTA ACTAAGCATC TCCACTATGG TGTGTGCCTT TTATAAAGGA
4801 AAAGAGAGAA AAAGGCAAAG CAAGGTTGTG GCCTTAGGTT GGACCTGGAA
4851 TATCCCTTAT TGCCTATAAT GGAATATGTG ACACTGTGGG TGAAATGTTC
4901 TACACACCAC ACACTAGGCC ATTTTCAGAT CAGCAGTCAC CCATCGCTTA
4951 GCATAGAAAT CCCAAAACCT CCAGCCCGGG AACACTATAA GCTTCGACCA
5001 TTCAGGAATC TGCCCTGCAC TTTGCATATC TGTATAGAAA ATCAAGTCAA
5051 TCCCCCATCC TCACACCCAC TCATCTCTGA GGAGCTATGA ACTGGTTTTG
5101 GTCCCTCTAA TGATCCTCCA GCCTCATCTA ATGCCCCCCA AAGACTGATA
5151 CAAGTAACCT CCCCTCTGCT TAGGTGTCAC TTTCTCAGCA TATCAAGTTT
5201 AGGCAGCAAG GGAAAGGAAT ATGGGTCAGT TCTCAAATGT CAATGTAGAT
5251 AAGAGTCATC TAGTAGAGAA CTCATCAGAG TGCGGATTGC CAAGACCCTT
5301 CTCCAGAGAT TATGGGGTTG GGGGTGGAGG TCTAGAGGTG AGCTCAGAAA
5351 CCTACTGTTA ACCAACACCC CCAAGTGACT GACACAGGTG GTCTAAAAAT
5401 TACTTTTCTA GAAACACCAT TCTGGAAGTT TGGCTGCCCA CAGGCAGGAG
5451 GAGAAGCATG AAGAGAAAAC CTGTTTGAGA AGTTTTGTTT TGTTTTGTTT
5501 TGCTTTTTAA TAATTTTAGC ACACATCTGC TGACTCTCCT TCAACATCCT
5551 CACCCCCACC CCTGGGCACC ATTTAGGACA AGACTTCCTT ATTTATCAAT
5601 TACTTGATTT ATCTTCTCAG GACTCATTGT TCCACCCCCA ACCAATTTGA
5651 ATGCCTACAA TAAGTTCAGG AGCTGTGCCA AGCACTTTCC TCTTTTACAG
5701 CTGGAGATCA CTGGAAAGGT GTCTCAGTCA CAAAACTTCT CCCTCTACTA
5751 CTGGATGAAA TGTCTGCATT TCCACCAAAA TCTACCCAGT CACCCAGGGA
5801 ATAACAACTT AAGCTGTAGT TAGATAACAC CTAGTGATTA ATTGGCTGAG
5851 AAAACCCTGG AGTGGAGGGA GGCTCAGAGA TACTGATATG GATGTGGGAG
5901 GGCTCTAAAG TTAGAGGTCA CCAACTCCAC AGATGAAACA GTTCAATAAT
5951 GAGGAAACAG GTGAGCCCTG AAAACACAAA AGGACAGTTC TGTGTTGAAA
6001 CACCCCATCC CCTCACGTTC TCACCCCAGG CCCAGAAGTA GGTTGCAACT
6051 GCCTTTGGAA GATTTTGCCC CTTAGCCATC CCCACCCACT TGTACCAGCT
6101 AAGAATGCTG GAGACTCTGC CACCATGCTC TGCGTGCCCC TGAACCTCTG
6151 TGCAGCCCGG AAGGCTGATG TACAGGTGTA CCTCAATCCA CATTACAGCC
6201 ATGCTCCTAA TGTACATGGA CATTTTTGTA ACTCAGCTCA TATTCTGACT
6251 GTATTTGAGA AGCTGGCTGT TTAAGGGAAC CCAGAAGTGA ATTCTTTTGT
```

FIGURE 1, page 2 of 4

```
6301  AAAGTAAAGC ACCCTTTTGT AATGCAATTA ATTATCCCTT AATGTATCTG
6351  TTTTGTAAGT CTGCATTTTT GTATATCGGA TTTACCTTAA GCTTCTCTAG
6401  TGAGGCATTC TGAGCAGTGG TGATCACATG CCAGATCGCC CTGCCTATCC
6451  ACAAAGTAGA TGACCAATGC ACGCTCCTCA AACATCTTTG GAGGAACTAC
6501  CTGGCCAAAA CACTGGCCAG GATGCAGCAA GCAGCAGCAG GGGCTGACAG
6551  CAGGCTTACT GCCATCAACA TTGCTTGAAA TGCCTCTATG TTCTGAATAA
6601  AGAAAAACCA TAATTGCTTG TGGTGAAACG AAGCAGTCTT CATGTTAAGT
6651  AGCAATGGTT ATTTTTATTG GTAGTAACTG AACAGTGTTT TGCAATTTGT
6701  GAAACAGTGT ATTGTGTTTT GTAAAATGAT GTCATGAAAT GGTGGGTCCT
6751  TGGAAACCTC CTTTCCGTTC AGCTCTGCCT CTGTTCTTTC AACTCCTTTG
6801  AGGCTCAAAA AAAACACAAA GATCAGAAGC CTTCAGATAG AGGGTGGTAT
6851  TCTGGTAAAG AAGAAAGAGA TAAGGGACGC TACCTTGCTT TTCTGGCACA
6901  GGAAGCACAT GATAAAGCAT GCTCAGATGA GCTGGAACAG ATATAGCTAC
6951  CTGGTTCGTG TAAATAAGAA TAATCAAGGC CCCAGAGTGT GTATGCTTCC
7001  AGGTGGAGGA GAAAGGGGAA TCTCCCAAAA TTTAAAAACA AATTGGAAGA
7051  ATAACCAGGA CAGCCAAGTG AAGCAGCCAC AGGGACCCAA GCAGTCGAGG
7101  TCTTTAATGT GCCTGGAGAT GACTCTCTGC TATTCATGAA TCTTGCTATT
7151  GCACAAACCC TATCAAGAGC TGCTGCTTCC CTTCCAGCCA GAAAAGTGGT
7201  AAGCGGAGCA AGTGCCAAGC AGAACAGACC TTATCATCTG GGTAACAGAC
7251  TTCTCAGTGT TGGTGCTGTG TCTGTTAGAG CCTTAGAGCA AGTTAAGCAC
7301  TTCCTTGGTG TGGGTAAAGA ATAAAGGGGA AAGAAACTAC TTTAGAGCCT
7351  CTTTTTCTCC CAACTCATAT TTTTGATAGG AAAAACAGAA AACCCATCCA
7401  GTTCTTCAGA AATTGCTTTC TAGGCATTAA TACTACTTTA CTATCTATAC
7451  TGTTTAGTTA TTCCTTTCTT TACCCACCTA AACTATCCAT CTAATCCAGG
7501  ATTCCCTCAC TCTTTTTTTT TAGTTACTAA TCATTTTATG AAAATAATGT
7551  ATTTATAAGT ATTTTCTTAA GGTTTGTGAA GAGTATTTGC ATTGTGTCTT
7601  CATTTTAATG TGTTTGCAAT CGCTCCGCTC CAGGAAGAAC GGAAATGCTG
7651  TCTTGTGAGC ATGAAGTGAA CGGGCTGTTT TGCTCCAGCC ACTTTTCTTG
7701  TACAACCACA TGGATGGATT AGATGTCCTC AGGTCTTTTC CATCTTCAGT
7751  TTCTATGACT GTGGAATAAA TGTTCAGATA GAAACTTCA (SEQ ID NO:1)
```

FEATURES:

5'UTR: 1-619
Start: 620
Stop: 3965
3' UTR: 3968-7789

HOMOLOGOUS PROTEIN:

Top 10 BLAST Hits:

```
gi|7514020|pir||T31068 N-methyl-D-aspartate receptor homolog NM...  1948  0.0
gi|5305435|gb|AAD41650.1|AF073379_1 (AF073379) N-methyl-D-aspar...  1936  0.0
gi|3025446|gb|AAC12680.1| (AC004528) R32184_2 [Homo sapiens]         906  0.0
gi|3822016|gb|AAD11811.1| (AF061945) NMDA receptor-like long va...   456  e-127
gi|286234|dbj|BAA02498.1| (D13211) N-methyl-D-aspartate recepto...   304  2e-81
gi|2155310|gb|AAB58801.1| (AF001423) N-methyl-D-aspartate recep...   302  1e-80
gi|6980982|ref|NP_036705.1|| glutamate receptor, ionotropic, N-...   302  2e-80
gi|6680097|ref|NP_032196.1|| glutamate receptor, ionotropic, NM...   300  4e-80
gi|6680099|ref|NP_032197.1|| glutamate receptor, ionotropic, NM...   299  8e-80
gi|4099613|gb|AAD00659.1| (U88963) N-methyl-D-aspartate recepto...   299  8e-80
gi|228950|prf||1814459A D-MeAsp receptor:SUBUNIT=epsilon2 [Mus ...   299  8e-80
gi|548372|sp|Q00960|NME2_RAT GLUTAMATE [NMDA] RECEPTOR SUBUNIT ...   299  8e-80
gi|6980984|ref|NP_036706.1|| glutamate receptor, ionotropic, N-...   299  8e-80
```

Figure 1:
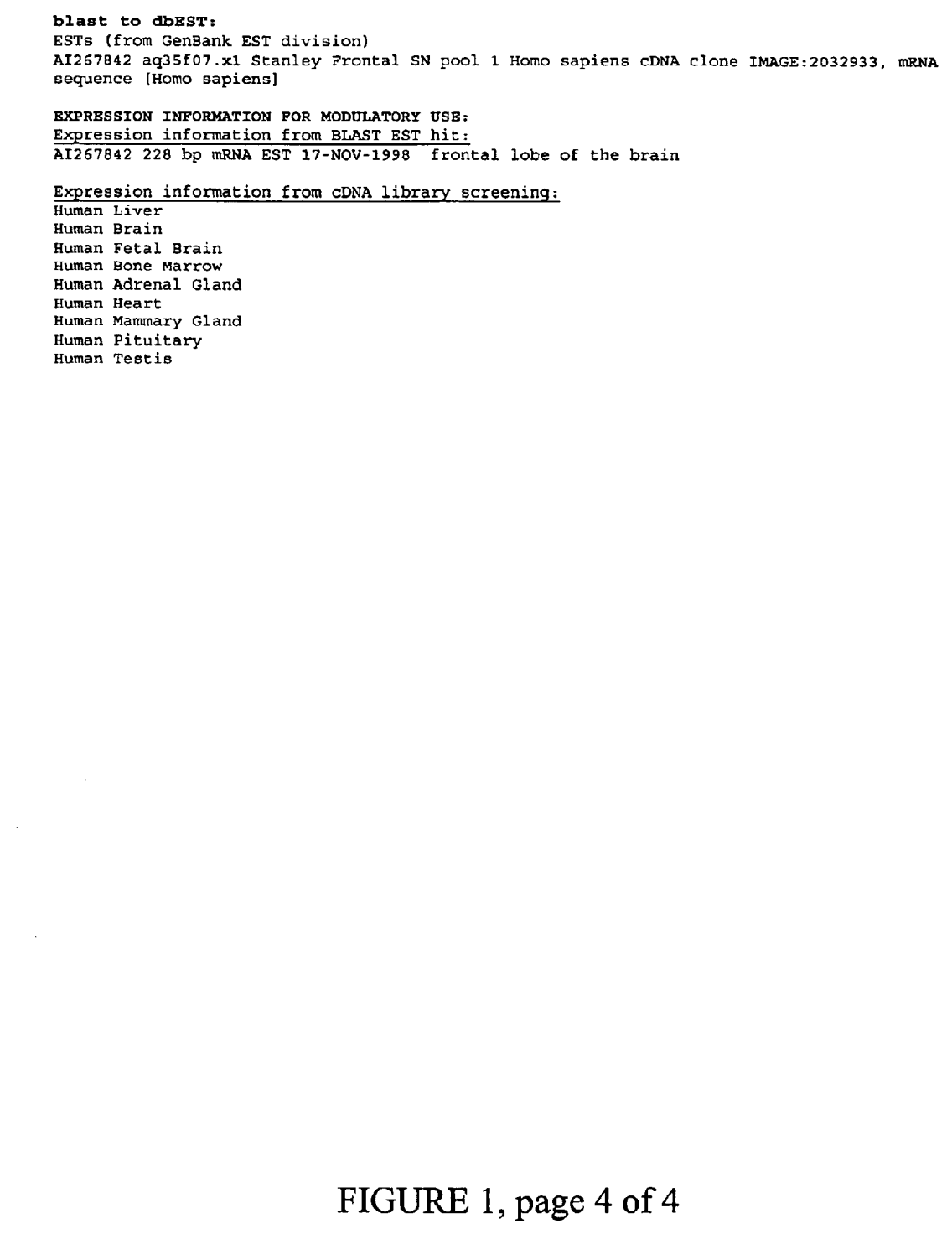

blast to dbEST:
ESTs (from GenBank EST division)
AI267842 aq35f07.x1 Stanley Frontal SN pool 1 Homo sapiens cDNA clone IMAGE:2032933, mRNA sequence [Homo sapiens]

EXPRESSION INFORMATION FOR MODULATORY USE:

Expression information from BLAST EST hit:
AI267842 228 bp mRNA EST 17-NOV-1998 frontal lobe of the brain Expression information from cDNA library screening:
Human Liver
Human Brain
Human Fetal Brain
Human Bone Marrow
Human Adrenal Gland
Human Heart
Human Mammary Gland
Human Pituitary
Human Testis FIGURE 1, page 4 of 4

```
   1 MRRLSLWWLL SRVCLLLPPP CALVLAGVPS SSSHPQPCQI LKRIGHAVRV
  51 GAVHLQPWTT APRAASRAPD DSRAGAQRDE PEPGTRRSPA PSPGARWLGS
 101 TLHGRGPPGS RKPGEGARAE ALWPRDALLF AVDNLNRVEG LLPYNLSLEV
 151 VMAIEAGLGD LPLLPFSSPS SPWSSDPFSF LQSVCHTVVV QGVSALLAFP
 201 QSQGEMMELD LVSLVLHIPV ISIVRHEFPR ESQNPLHLQL SLENSLSSDA
 251 DVTVSILTMN NWYNFSLLLC QEDWNITDFL LLTQNNSKFH LGSIINITAN
 301 LPSTQDLLSF LQIQLESIKN STPTVVMFGC DMESIRRIFE ITTQFGVMPP
 351 ELRWVLGDSQ NMEELRTEGL PLGLIAHGKT TQSVFEHYVQ DAMELVARAV
 401 ATATMIQPEL ALIPSTMNCM EVETTNLTSG QYLSRFLANT TFRGLSGSIR
 451 VKGSTIVSSE NNFFIWNLQH DPMGKPMWTR LGSWQGRKIV MDYGIWPEQA
 501 QRHKTHFQHP SKLHLRVVTL IEHPFVFTRE VDDEGLCPAG QLCLDPMTND
 551 SSTLDSLFSS LHSSNDTVPI KFKKCCYGYC IDLLEKIAED MNFDFDLYIV
 601 GDGKYGAWKN GHWTGLVGDL LRGTAHMAVT SFSINTARSQ VIDFTSPFFS
 651 TSLGILVRTR DTAAPIGAFM WPLHWTMWLG IFVALHITAV FLTLYEWKSP
 701 FGLTPKGRNR SKVFSFSSAL NICYALLFGR TVAIKPPKCW TGRFLMNLWA
 751 IFCMFCLSTY TANLAAVMVG EKIYEELSGI HDPKLHHPSQ GFRFGTVRES
 801 SAEDYVRQSF PEMHEYMRRY NVPATPDGVE YLKNDPEKLD AFIMDKALLD
 851 YEVSIDADCK LLTVGKPFAI EGYGIGLPPN SPLTANISEL ISQYKSHGFM
 901 DMLHDKWYRV VPCGKRSFAV TETLQMGIKH FSGLFVLLCI GFGLSILTTI
 951 GEHIVYRLLL PRIKNKSKLQ YWLHTSQRLH RAINTSFIEE KQQHFKTKRV
1001 EKRSNVGPRQ LTVWNTSNLS HDNRRKYIFS DEEGQNQLGI RIHQDIPLPP
1051 RRRELPALRT TNGKADSLNV SRNSVMQELS ELEKQIQVIR QELQLAVSRK
1101 TELEEYQRTS RTCES (SEQ ID NO:2)
```

FEATURES:

Functional domains and key regions:

```
PDOC00001 PS00001 ASN_GLYCOSYLATIONN-glycosylation site
Number of matches: 16
      1    145-148 NLSL
      2    264-267 NFSL
      3    275-278 NITD
      4    285-288 NNSK
      5    296-299 NITA
      6    426-429 NLTS
      7    439-442 NTTF
      8    549-552 NDSS
      9    565-568 NDTV
     10    709-712 NRSK
     11    886-889 NISE
     12    965-968 NKSK
     13    984-987 NTSF
     14  1015-1018 NTSN
     15  1018-1021 NLSH
     16  1069-1072 NVSR
--------------------------------------------------------------------------------[2]
PDOC00004 PS00004 CAMP_PHOSPHO_SITEcAMP- and cGMP-dependent protein kinase phosphorylation
site
               2-5 RRLS
--------------------------------------------------------------------------------[3]
PDOC00005 PS00005 PKC_PHOSPHO_SITEProtein kinase C phosphorylation site
Number of matches: 14
      1      85-87 TRR
      2    110-112 SRK
      3  1098-1100 SRK
      4    317-319 SIK
      5    334-336 SIR
      6    448-450 SIR
      7    441-443 TFR
      8    334-336 SIR
      9    448-450 SIR
     10    636-638 TAR
     11    704-706 TPK
     12    741-743 TGR
```

FIGURE 2, page 1 of 4

```
     13    796-798 TVR
     14    976-978 SQR
--------------------------------------------------------------------------[4]
PDOC00006 PS00006 CK2_PHOSPHO_SITECasein kinase II phosphorylation site
Number of matches: 17
      1    202-205 SQGE
      2    248-251 SDAD
      3    303-306 STQD
      4    383-386 SVFE
      5    519-522 TLIE
      6    552-555 STLD
      7    563-566 SSND
      8    693-696 TLYE
      9    796-799 TVRE
     10    800-803 SSAE
     11    801-804 SAED
     12    809-812 SFPE
     13    949-952 TIGE
     14    986-989 SFIE
     15  1030-1033 SDEE
     16  1080-1083 SELE
     17  1101-1104 TELE
--------------------------------------------------------------------------[5]
PDOC00007 PS00007 TYR_PHOSPHO_SITETyrosine kinase phosphorylation site
         1099-1106 RKTELEEY
--------------------------------------------------------------------------[6]
PDOC00008 PS00008 MYRISTYLN-myristoylation site
Number of matches: 10
      1      27-32 GVPSSS
      2    292-297 GSIINI
      3    369-374 GLPLGL
      4    430-435 GQYLSR
      5    444-449 GLSGSI
      6    482-487 GSWQGR
      7    535-540 GLCPAG
      8    606-611 GAWKNG
      9    680-685 GIFVAL
     10    876-881 GLPPNS
--------------------------------------------------------------------------[7]
PDOC00009 PS00009 AMIDATIONAmidation site
Number of matches: 2
      1    485-488 QGRK
      2    913-916 CGKR
--------------------------------------------------------------------------[8]
PDOC00017 PS00017 ATP_GTP_AATP/GTP-binding site motif A (P-loop)
           373-380 GLIAHGKT
```

Membrane spanning structure and domains:

| | | | | |
|---|---|---|---|---|
| 1 | 13 | 33 | 1.496 | Certain |
| 2 | 182 | 202 | 1.149 | Certain |
| 3 | 206 | 226 | 0.679 | Putative |
| 4 | 251 | 271 | 0.628 | Putative |
| 5 | 399 | 419 | 0.694 | Putative |
| 6 | 639 | 659 | 0.949 | Putative |
| 7 | 675 | 695 | 2.050 | Certain |
| 8 | 711 | 731 | 1.052 | Certain |
| 9 | 744 | 764 | 1.803 | Certain |
| 10 | 931 | 951 | 2.294 | Certain |

FIGURE 2, page 2 of 4

BLAST Alignment to Top Hit:

```
>gi|7514020|pir||T31068 N-methyl-D-aspartate receptor homolog NMDAR-L
          - rat >gi|1050330|gb|AAA99501.1| (L34938) ionotropic
          glutamate receptor [Rattus norvegicus]
          >gi|2160125|gb|AAB58957.1| (U29873) NMDAR-L [Rattus
          norvegicus]              Length = 1115
 Score = 1948 bits (4990), Expect = 0.0
 Identities = 941/1089 (86%), Positives = 992/1089 (90%)
Query: 27   GVPSSSSHPQPCQILKRIGHAVRVGAVHLQPWTTXXXXXXXXXXXXXXGAQRDEPEPGTR 86
             GVPSSSSHPQPCQILKRIGHAVRVGAVHLQPWTT              GAQRD+PE GT
Sbjct: 27   GVPSSSSHPQPCQILKRIGHAVRVGAVHLQPWTTAPRAASRAQEGGRAGAQRDDPESGTW 86

Query: 87   RSPAPSPGARWFGSTLHGRGPPGSRKPGEGARAEALWPRDALLFAVDNLNRVEGLLPYNL 146
             R PAPS GARW GS LHGRGPPGSRK GEGA AE LWPRDALLFAV+NLNRVEGLLPYNL
Sbjct: 87   RPPAPSQGARWLGSALHGRGPPGSRKLGEGAGAETLWPRDALLFAVENLNRVEGLLPYNL 146

Query: 147  SLEVVMAIEAXXXXXXXXXXXXXXXXXXXXXXXXXQSVCHTVVVQGVSALLAFPQSQGEM 206
             SLEVVMAIEA                         QSVCHTVVVQGVSALLAFPQSQGEM
Sbjct: 147  SLEVVMAIEAGLGDLPLMPFSSPSSPWSSDPFSFLQSVCHTVVVQGVSALLAFPQSQGEM 206

Query: 207  MELDLVSLVLHIPVISIVRHEFPRESQNPLHLQLSLENSLSSDADVTVSILTMNNWYNFS 266
             MELDLVS VLHIPV+SIVRHEFPRESQNPLHLQLSLENSLSSDADVTVSILTMNNWYNFS
Sbjct: 207  MELDLVSSVLHIPVLSIVRHEFPRESQNPLHLQLSLENSLSSDADVTVSILTMNNWYNFS 266

Query: 267  LLLCQEDWNITDFLLLTQNNSKFHLGSIINITANLPSTQDLLSFLQIQLESIKNSTPTVV 326
             LLLCQEDWNITDFLLLT+NNSKFHL S+INITANL ST+DLLSFLQ+Q+++I+NSTPT+V
Sbjct: 267  LLLCQEDWNITDFLLLTENNSKFHLESVINITANLSSTKDLLSFLQVQMDNIRNSTPTMV 326

Query: 327  MFGCDMESIRRIFEITTQFGVMPPELRWVLGDSQNMEELRTEGLPLGLIAHGKTTQSVFE 386
             MFGCDM+SIR+IFE++TQFG+ PPEL WVLGDSQN+EELRTEGLPLGLIAHGKTTQSVFE
Sbjct: 327  MFGCDMDSIRQIFEMSTQFGLSPPELHWVLGDSQNVEELRTEGLPLGLIAHGKTTQSVFE 386

Query: 387  HYVQDAMELVARAVATATMIQPELALIPSTMNCMEVETTNLTSGQYLSRFLANTTFRGLS 446
             +YVQDAMELVARAVATATMIQPELAL+PSTMNCM+V+TTNLTSGQYLSRFLANTTFRGLS
Sbjct: 387  YYVQDAMELVARAVATATMIQPELALLPSTMNCMDVKTTNLTSGQYLSRFLANTTFRGLS 446

Query: 447  GSIRVKGSTIVSSENNFFIWNLQHDPMGKPMWTRLGSWQGRKIVMDYGIWPEQAQRHKTH 506
             GSI+VKGSTI+SSENNFFIWNLQHDPMGKPMWTRLGSWQG +IVMD GIWPEQAQRHKTH
Sbjct: 447  GSIKVKGSTIISSENNFFIWNLQHDPMGKPMWTRLGSWQGGRIVMDSGIWPEQAQRHKTH 506

Query: 507  FQHPSKLHLRVVTLIEHPFVFTREVDDEGLCPAGQLCLDPMXXXXXXXXXXXXXXXXXXX 566
             FQHP+KLHLRVVTLIEHPFVFTREVDDEGLCPAGQLCLDPM
Sbjct: 507  FQHPNKLHLRVVTLIEHPFVFTREVDDEGLCPAGQLCLDPMTNDSSMLDRLFSSLHSSND 566

Query: 567  XVPIKFKKCCYGYCIDLLEKIAEDMNFDFDLYIVGDGKYGAWKNGHWTGLVGDLLRGTAH 626
              VPIKFKKCCYGYCIDLLE++AEDMNFDFDLYIVGDGKYGAWKNGHWTGLVGDLL GTA+
Sbjct: 567  TVPIKFKKCCYGYCIDLLEQLAEDMNFDFDLYIVGDGKYGAWKNGHWTGLVGDLLSGTAN 626

Query: 627  MAVTSFSINTARSQVIDFTSPFFSTSLGILVRTRDTAAPIGAFMWPLHWTMWLGIFVALH 686
             MAVTSFSINTARSQVIDFTSPFFSTSLGILVRTRDTAAPIGAFMWPLHWTMWLGIFVALH
Sbjct: 627  MAVTSFSINTARSQVIDFTSPFFSTSLGILVRTRDTAAPIGAFMWPLHWTMWLGIFVALH 686

Query: 687  ITAVFLTLYEWKSPFGLTPKGRNRSKVFSFSSALNICYALLFGRTVAIKPPKCWTGRFLM 746
             ITA+FLTLYEWKSPFG+TPKGRNR+KVFSFSSALN+CYALLFGRT AIKPPKCWTGRFLM
Sbjct: 687  ITAIFLTLYEWKSPFGMTPKGRNRNKVFSFSSALNVCYALLFGRTAAIKPPKCWTGRFLM 746

Query: 747  NLWAIFCMFCLSTYTANLAAVMVGEKIYEELSGIHDPKLHHPSQGFRFGTVRESSAEDYV 806
             NLWAIFCMFCLSTYTANLAAVMVGEKIYEELSGIHDPKLHHPSQGFRFGTVRESSAEDYV
Sbjct: 747  NLWAIFCMFCLSTYTANLAAVMVGEKIYEELSGIHDPKLHHPSQGFRFGTVRESSAEDYV 806

Query: 807  RQSFPEMHEYMRRYNVPATPDGVEYLKNNPEKLDAFIMDKALLDYEVSIDADCKLLTVGK 866
             RQSFPEMHEYMRRYNVPATPDGV+YLKN+PEKLDAFIMDKALLDYEVSIDADCKLLTVGK
Sbjct: 807  RQSFPEMHEYMRRYNVPATPDGVQYLKNDPEKLDAFIMDKALLDYEVSIDADCKLLTVGK 866
```

FIGURE 2, page 3 of 4

```
Query: 867   PFAIEGYGIGLPPNSPLTANISELISQYKSHGFMDMLHDKWYRVVPCGKRSFAVTETLQM 926
             PFAIEGYGIGLPPNSPLT+NISELISQYKSHGFMD+LHDKWY+VVPCGKRSFAVTETLQM
Sbjct: 867   PFAIEGYGIGLPPNSPLTSNISELISQYKSHGFMDVLHDKWYKVVPCGKRSFAVTETLQM 926

Query: 927   GIKHFSGLFVLLCIGFGLSILTTIGEHIVYRLLLPRIKNKSKLQYWLHTSQRLHRAINTS 986
             GIKHFSGLFVLLCIGFGLSILTTIGEHIV+RLLLPRIKNKSKLQYWLHTSQR HRA+NTS
Sbjct: 927   GIKHFSGLFVLLCIGFGLSILTTIGEHIVHRLLLPRIKNKSKLQYWLHTSQRFHRALNTS 986

Query: 987   FIEEKQQHFKTKRVEKRSNVGPRQLTVWNTSNLSHDNRRKYIFSDEEGQNQLGIRIHQDI 1046
             F+EEKQ   KTKRVEKRSN+GP+QL VWNTSNLSHDN+RKYIF+DEEGQNQLG + HQDI
Sbjct: 987   FVEEKQPRSKTKRVEKRSNLGPQQLMVWNTSNLSHDNQRKYIFNDEEGQNQLGTQAHQDI 1046

Query: 1047 XXXXXXXXXXXXXTTNGKADSLNVSRNSVMQELSELEKQIQVIRQELQLAVSRKTELEEY 1106 (residues 27-1106 of SEQ ID NO:2)
                          TTNGKADSLNV+R+SV+QELSELEKQIQVIRQELQLAVSRKTELEEY
Sbjct: 1047 PLPQRRRELPASLTTNGKADSLNVTRSSVIQELSELEKQIQVIRQELQLAVSRKTELEEY 1106 (SEQ ID NO:4)
```

Hmmer search results (Pfam):

| Model | Seq-from | Seq-to | HMM-from | HMM-to | Score | E-value | Description |
|---|---|---|---|---|---|---|---|
| lig_chan | 674 | 952 | 1 | 304 | 199.6 | 1.7e-57 | Ligand-gated ion channel |

FIGURE 2, page 4 of 4

```
   1 ATGGAAACTT TAGCTCATGA ATCAAAACAA CCCTCCAGAG CTAAAAGCCA
  51 GCTGTATTTG CATAACAATT TAGCAGATCC AAACAGCAGG GCAAGGTCGG
 101 GTGAAATAAG TTGCCAAGGT CATGGTCATG AAGTAGTATT AGACTCAGAA
 151 AGGCTGATCC CCAGTGCTTG CTCCACCCCA TGGATCTCTC CTACCCTCCT
 201 TCTAAACGAT ACTGTGGGAT AAAATAAAAT TAATCTACTG TATATGTGCA
 251 AACCACAGGC CTGCCCTTAA CTCTTTCCTT ACCTTCTAGT TTCAGATTAT
 301 TCAAATCATG GAGGAAAAGA TTAGATCACA ACACGTTGAC TTCACTGTAT
 351 TACCATACAA ATGAAATAAC TTAGTACAAA CTGTGATCTG GGGACTCTTG
 401 ATCTAAACTG GGAACTGCTG TTGACTGCAT TTTAAACTCT AAAAGTATTT
 451 TGAAACTCTT TAATTTCTTG AACTGAAAAA ATTGCTTTGA ATTCACTTTG
 501 TTTTAATTCT GAGAACCTAA AAACAGGGAT TCTTTAAAAA AAAAAATGCA
 551 AAGGCTCACA TGCCAGAAAG AAAGAAGCTG AGGAGATAAA AATGTGTAAA
 601 TAATTCTTAC TTTAATACCC TTAGCTAGAA AAACCTTAAA AGCGACACAT
 651 CCAGAAGCTC GTTAAGTCAC AGCCTCTTTG AACCTATTTC AGTGAACCAC
 701 CGAATTTCAG ATCCCTCAGG TGCGACTCTG AATTCAGAAT TCTCACCGGC
 751 TCATAGTCCT ATTTTCCTTC TTAGGTTTTA GGGAATTTTG CAAACTATGA
 801 CGCCCAGCCT TTGAGGGGAG AGGACTTTCC AGGGGCGCGG GATGTGCCAC
 851 TCGGGAATCT CACCAACAGT GGGCGTTTAG CGCAGCCAAG CGACAGGCAG
 901 GCGCCAGGGC TCAGCAACAG GGAGGCGCCG GCTGAGGCGG GGAGAACTTT
 951 GGCGCTCGGA GCAGAGCCAC CCTTTGCTGG CCAGTCGCGT TGCTCCTCCG
1001 AGGAAGCAAG CGGCGGTGGC GACTCGGTGG AAAAATAACG AAAGAAAGGC
1051 AGAGAGGAAG TAGCGAGAGA AGAGAGAAAA TGAAGTCGGC GCTGGGGGAG
1101 CCTGCAGGAG GGTGGCCAAC AGTGGAGGAA GGTGGATTTG GCTTCTTTTC
1151 CGCACCCCGG GCGTGAAAGC CCTCTCCAAC GCGACCCCAG GAAATAAGTG
1201 GGTCTCGCCT GGGCAGAAAA GGAAAAGAAT CCAGGCGAGA GCGCGTCGCT
1251 CCTCTGTCAC TGCTGCCCCC GAGGAACTCC GGCTGCTTCT CATCCCGGCC
1301 GCCTCGCGGG GCCGGACGCA GTGCCCGAGG CGCCCTGCAG ATGGGGCGGG
1351 CAGGGAACGG GCGCTCCAGC TGCGGGTGAC AGGCGCCGGC CCGCCCGCCT
1401 GCCTGCTCAG CGCAGTGACC GGGCGGGCAG AGGATGCCAG GCGGAGGGAC
1451 CTGGGAGCGG GATCTGAGAC TGCCGGAGGC GCGCTACGCT CCAACTTGCA
1501 TGGCCTAGAG ACCGCTCCAG CTCCTGGGAC CGCTTCACCG AGTGGAGTGA
1551 AGCTGCGCGC GGGACCTGGA GGCGGAGACC TCAGGCAGCG GCTGCAGAGG
1601 GGCGAGCCGG GCGCAGGAGG GGGCGCGCTT TCTCCCTGCG GGTCTCAGTA
1651 ATGAGGAGAC TGAGTTTGTG GTGGCTGCTG AGCAGGGTCT GTCTGCTGTT
1701 GCCGCCGCCC TGCGCACTGG TGCTGGCCGG GGTGCCCAGC TCCTCCTCGC
1751 ACCCGCAGCC CTGCCAGATC CTCAAGCGCA TCGGGCACGC GGTGAGGGTG
1801 GGCGCGGTGC ACTTGCAGCC CTGGACCACC GCCCCCCGCG CGGCCAGCCG
1851 CGCTCCGGAC GACAGCCGAG CAGGAGCCCA GAGGGATGAG CCGGAGCCAG
1901 GGACTAGGCG GTCCCCGGCG CCCTCGCCGG GCGCACGCTG GTTGGGGAGC
1951 ACCCTGCATG GCCGGGGGCC GCCGGGCTCC CGTAAGCCCG GGGAGGGCGC
2001 CAGGGCGGAG GCCCTGTGGC CACGGGACGC CCTCCTATTT GCCGTGGACA
2051 ACCTGAACCG CGTGGAAGGG CTGCTACCCT ACAACCTGTC TTTGGAAGTA
2101 GTGATGGCCA TCGAGGCAGG CCTGGGCGAT CTGCCACTTT TGCCCTTCTC
2151 CTCCCCTAGT TCGCCATGGA GCAGTGACCC TTTCTCCTTC CTGCAAAGTG
2201 TGTGCCATAC CGTGGTGGTG CAAGGGGTGT CGGCGCTGCT CGCCTTCCCC
2251 CAGAGCCAGG GCGAAATGAT GGAGCTCGAC TTGGTCAGCT TAGTCCTGCA
2301 CATTCCAGTG ATCAGCATCG TGCGCCACGA GTTTCCGCGG GAGAGTCAGG
2351 TGAGAGGAGC CTGGTGCGTG GAGTGGAGAT GGGCGCTGCT GGGGGCCGGG
2401 GCCATTGCAT GAGGGGAGAG AAAACGGCTT GGTAAAGTCT GAGGGGAGTT
2451 GTTACTTTAT AACTTTGATA TTGCTTAACG ATTGGGCCAT GTTCGTAGGT
2501 GGTAGGTAGA AGGAGCTTAG TAGAAGTAGA ATAAAATATT TAAAGCGCGG
2551 ATGGAAATAA AACGCGCAGT GAGGTCGCGG CTGGAAGGAA AGAAGTGGGG
2601 AGAATATGAG AGAAAATCAT ATTTGACCG GCTGGGAGAA ATCTAGTAGA
2651 TGCCCGACGG GAAGTAGAAG TCGAGGTTCA GGACCGTGGA GAGCGGTGAA
2701 GGTTCTGAAG AACTACAAGA GCAGGGTATG GGGGTGGGGT ATCCCTGACT
2751 CCTGGCTAGG TGTCACACTC CCAAGAGCAA CTCTGACAGC ATGTGTCGGA
2801 AAAGCAGCAT CTGCTCTCTC TGACTTCTTC AGAAGGTGTG CCTGAGCCTT
2851 AGGCAAAGGT GTAAGGAAGA AAGCACATCG CTCTGAATTC CTCTGGGTAA
2901 ATAGAAAATC TGCACCTAGT ACAGAAGCCA TAGGTAGAGA AGAGTGGTCA
2951 ATTAGTCTCG GATATTGGAA AGCATTAGAA ATATATAAAA GTGTAAAGAT
3001 GGACGGGGAG ATTTATTTGG GGATTGTTTC TTTGTCCCTA CTTTCCTTCT
3051 ATGTAATGTG GACTCAGAGG CTGGTATTCA GTTGCTGTGT TCAGCCCATT
3101 TCTCTCCCCA TCATCTAAGA ATTAAAAAAA AAAAGGAATT AAATGATTTA
3151 GTTTCTTATT GATTAAAAAA GCTAAACATA TTTTCAATGA AAGAGCTATT
```

FIGURE 3, page 1 of 27

```
3201  TGTGAACTTA ACGTTGACAA GTAATAATGA GGAGATGAAT CTTTAAGGAC
3251  AAGACAGAGT CCTTATTTAG TAATGAGTTT TCTGCCTTTT ATATGTTACT
3301  TTTATCATAA TCTCAAGCTG TGTTAAGCCT TGCACAAAGT ATCTATGAAG
3351  CAAATAGGTA ATTGGCATGG GCCCATTTTA ACGACTGAGA AACTGAGAAA
3401  AGTCTGGGGA CTTGATCAAC ATTGGTCAGT GTACTAGTAA AAAAGTCCAC
3451  ATTCTGGAGG ATTTCTGACT CTACATCATT TTCACTCAAC TCTTGCAGCT
3501  GGAAAAATAT GTATTTCCAA TCTTCTTCCA CTTCTGATAT ATGTGCCGAG
3551  ATAAAAACTA AAATGAGTAA GGGCAATGTA CAATGAAAAG TTTGATAGAA
3601  TCTATGCATA AATTGTCAAG GGAGTACTAA AGATTTCTTT TTCTAGAAGA
3651  AAATAAATCT TACATTTTTA ATCTTAGGAA GGTTGAGTAC AAGCCATATT
3701  CAGCAGTTGC CCAGAAGATT CCTAGCCGAA CTACAGAGAT TTGATCTGTA
3751  GAGTGCAGGC TAATTAACTT TTATATAAAA TATTTCTGTC ACCTGAATCT
3801  GAATGGTGTA GGCAGCAGAT GGGAAGGCAT GGAAAACACA GATACACAAT
3851  GCTGCCAATG ACCAAAGTGT TATAAACATG AAATTGCATC CATAGGGTGC
3901  ATCATTATTA ATATACATGC AGAATCAGAT CTAACAAAAT GCAGGAGTCA
3951  GCATCACTTG CTTCTTATCA TTGCTTCTTT ATTACCTAAT ACTTCGTAAG
4001  TGGCCAATAG TGGTCACAGT CTCCAGACTC CTTTTCATTT GTAGATTGTT
4051  TGGCAAGAGT CTTAAGTAGC AAGAATTTTT CACCAAAATT CGTGTTCCTT
4101  AGTTAGAAGG GAAGTTGTGT TCTAGAACGG ATGTGTGCAG CATACAGCAC
4151  ATTACAACAA GGGGACCAGA AAAACCATGA AGCAGAATCC AGAATCTGTA
4201  AACTTCAAAG CTCTAAGACC GGGGTGGGGG GTGGATAAAG TCCTCCAGGG
4251  ACAAGCTGAC AATAAAATAA ATACGCTGTC AAGCACATTT GTTTCTGTAT
4301  TTCAACTCAG AAACATATTT TAAATCACTG TTGTCACTGT TACCTTCATG
4351  GCACACATCT TGAAAGGGAG AGATTATTAT ATTAACTCAG ATCTAGTTTG
4401  TTCAACTGAC TACATTTTCT TTCATCTCCC TTTTTACTTT AAATTCAAAC
4451  ATATCTAATT TGTCTTACTT TTGGTATCTC ATTTAAATGT CATTCTATAA
4501  TATTCTGTAT TAAGAATGTT CTGATCAATG CCAAGTCACT GTAATATATA
4551  ATTTTAAGAT GACCGTAATC TGCTTTCAGT GAAAACAATA ACTGATCTTT
4601  CCCTTGCTTC TCTGGAAAAG TGGACCTTCC TCTAATGCAG TGATGTGATT
4651  TTTAAAAACT TTCTATATAT AAAAGGATGT CAAACTCATT TTACACATTA
4701  AATAAAATTG ACTTAATCTA GCCACCATCC TCGGAGTCTA CTGCCCAGTG
4751  ACCTAATTTG TTGGTTGTGT GCCACTCCCT GAATAAAGGA TTCGAGAAGA
4801  AAGTGGACTT TTTCACACAA CCAAGTAAAA TAAAATTGTG TCTCTTACTT
4851  AAATCAAAAT TGCTTTCATA GCAAGAGCAG CAACAGCTGT TTTCTCTCAC
4901  TTTATTTTGG GCTGCTGATT ACATTCATCT GAAGGTTTTA ATTAATGAGC
4951  AATAGTTTTG GTAACATCCT GCCACAACTC TTAAATGGAA AGAGCTGCCA
5001  CTGAGATGGA CAAACCCCTG AGAAAAGCAT AATAGTTTTA TTTCAATACA
5051  CTATGTATTC AAAATAAGAT AATCACATAA GATCATCACC TTCTAGGGGA
5101  TCAGCTTCTT TCAAGTAGGG AAATTCATTA AAAGTAAGTT AGTTAACTAC
5151  ATACTTTTGG AAAACATATG TATATTATAA CTGCATAATA AAAGCTTAAT
5201  AAAACATTAA ACATAGGATG GGGTCAAAGC AGTTTTCCAT CAAAAGAATT
5251  CTGACTTCAC TACAACACTC AAACCCCACT TGAGGCTAAC CCATTTTATT
5301  AAAATGATTA CTTCTTTGTT CTAAATTCTA TTCTTATAAC CTTCAAATAA
5351  TGATGCTGAA TATGAACCTA ATTCCATTTA CACCTAAATT AAATTCCTGC
5401  AGTTATACTT TCTTTCTCTC TCCTTCCTAC ATGACTTTTT CTTCTACAGG
5451  TTTTGTGTAG TTTCTTCAAA GTTAACTCCC TAAAGTTTAC CTGCTGAAGT
5501  AGTGACAAGT ACACATTTTT TTAAAAAAAT ATACACCTCA CCTTAACTTC
5551  ATATTGGTTC TATTAGGCAG AGTTAATGAT GTAATATAAT TGGCTTAGAT
5601  CCAAATCCAT GCAATTCAAA AGTGACTGCA CAGCCAGGCA TGGTGGCACC
5651  TACATGTAGT CTCAGCTGCT TGGGAGGCTG AGGCAGGAGG ACGGCTTGAG
5701  CCCAAGAGTT CCAGACTACC CTGGGTGACA TAGTAAGACC CTGACTCTTA
5751  AAAAAATTTT TTAATTAAAA AAAAAAGTGA TCCCACTACT ATTTTCAACA
5801  CTCTCGTTGA ATACACCAAC CACAACTTTG CCTGCTTCAT GAGCGATATG
5851  TACTAACAAA TTAATATATG CTTCTTTCAT GGAAATACAA GTGTTTTAAA
5901  TTGTGCATTT TCTCTGACAG TACAGGACTA AGCACTGAAG CCTATTTATT
5951  AGAATTTGGC TAACAAAGCA CTATTTTTGC ATGGCACAGG GGTACCTCAT
6001  GAGGGGACCA GTAAGGGATA TTTATTTTTA AAACATCTGC TCTCAACTGT
6051  GTTGGTTTTC TTTGACTTGC TCTATGCAAA TCACAGCTCT TTCTCCTCTG
6101  GGGGAAATGT ATTCTGCAAT TCATGATGAA TAGCTGATAG TCGCATCTAA
6151  TTGTTGCTGA CTTAAAGATA AACAATTTCA AATTAAATGT CAAGTGATGC
6201  AAAACTTTTT AAAGCAGTGA TCTTTTACAG GTTCCTCTTG AAGAACAGAG
6251  ACCTGGCATT AACTTGGAAG TATTTTTTAA TTTAGTTATT TACTTACAAT
6301  ATGTATTCGC TTTTCTAGAT AAGTAGAGCA AAGGAGACTA GCAGGCACCA
6351  TTTATTGAGC AATTAGTTTG TCTCTCCCGC TTTACTTTGT GCTTGCCAGA
```

FIGURE 3, page 2 of 27

```
6401 AGAGTATCAC TTAATCCATG AAGAATATAT TTGCTCTTGA TTTTGTCTGA
6451 CCATTATATC TTAGAGTTAA TTTATGATCG AATCAGCTGA GGTATCTGAA
6501 GACTGATGCC AATTTCTAAT TCCTCGTGTT TTATCTTCTG GTGCTGCAGA
6551 AGGCACCATG GATTTTGTAC CATTAGATTT TATTTTATAA ATAACCCCCC
6601 AGTCAAATTC CAACCACAAT AGTTAAAAGA GCACAATGTA ATGAAACGCA
6651 TATGAAATAG TGGCCAAAAT GTTCCCAATC TGCCTCTTTC GTTGCAGATG
6701 TTCCCAATCT ATCTCTCACT AGCCATGTAA TTTTGGGCAA GTGACTATCT
6751 CTGAGCATCT ACACTTATCA GAAGTGTAGA TCAAAAGAAG GTACTTTACC
6801 AATCTGACAA AGATGTTGTG AATCAAATGA GAAAGTAAAA GTACTTTGGA
6851 AAAGTTATAG TGTTACCCAA ATAACTAGTG GAGAGGTGTT GGTCATTATC
6901 TGGTAAGAAT CACTTAAGTG TTAAAGTTCA ACTAATTTTC TTTTCGAAAT
6951 TACTAATCAA AATGAGATAT GATTCACATG TAAAATGTTT GCATTCCCCT
7001 TACACCTTCC TCTTTACCCT CTCCCTCATT TTTTTCTCTT AAAAAAAAGT
7051 GGGCTTAGAA ATAAACAAAC AAACAAAAAA CTAGGTTCCT AAGTAGGTTG
7101 CACACTTGCC TGGAAAAAGA AGACATGCCA CAGTACTGTT TCTGTATTAC
7151 CAGCAACTTT TAACCTATGG CACATCTAAC ACAGCTTCTA GAGCCTTAAG
7201 TCCTGCCATA GAAATATCAT TAAGATGCCC AAGATATTTG AGAAATGTTG
7251 GTCCTTCACA TTGCTCATAA GTTTTTTCTA TAGGCAAACT ATCATTCAGG
7301 AAATTATGAC CAAACAGAGT CTACCCCACT CTCACTCCTA TTCCGCCAAC
7351 TACACCACAA AGCAAACATC CAAATTTTTT CATAGCAAAC TTTCTTGATA
7401 AGGAAAGCAG TGTGTTGATT CATACTGACC TAAGCTCCTT ATCTCATCAT
7451 GGATATATAA TTTACAAACC AGCTACTTTG AGTCCCATTG CCCTAGATAA
7501 CTGTATACTC TCTTAGGAAA GTATTGCTCA TTTTAGTGGC AACAGTAAAT
7551 ATAGAGATGA GAAATCTCAT TGTCTTTTTT TCTGCTAGCT CTGGCTATTG
7601 CCACATATAC ACAAGAATAG AGGACCTATG TAGCACCAGA AATATGATGC
7651 CAAATCCATA AAACTAGGCA AGAAGAAAGA ACATCTCTTA GCATCTGCCA
7701 TATTACTTTT TGAGTGAATG TTTGAATGAC AAACTCATAG AAATTTTTAA
7751 CCTCTCAGTT GTCTTTTGCT GATATTTTCT CTATGAGATC ACAGGAGCAA
7801 AGAGCAATGG GGAAGAGGTG AGCTAAGAGT AAGCCAACTC TCTCCATTTC
7851 CTTCTCCTTT CCTCAACCTG ACACCTCAGC CAAATTCTCA GATATTTTAT
7901 TTAATTGTGT AAGATTCATG CACTTTCAGG GAGACTGTCA ACTGTATTTG
7951 ATCTCCTGCC TTGAAAAAGT GGGTTGATCC CTGACCTGGC TGGCATTATG
8001 TCATGAGGAG TAAACTTTGA CATTGAAAGG CTGGTGTCTG ATTGGCCAGG
8051 GCTGGTTTGT TAATGGAGAT GAGCCTGCAA GGGTTCATGT GGTAGAGAAT
8101 TAAGCAGGAT GACTCCTTTT TCAGTCAGGA TGAATTACAC CTCATCGTTA
8151 TTCATTTGAA GCATAGATTT AGGAAGAATT TTAATCATAT TATATTTTTG
8201 CAGCATTTAT GTTTTCAAGG CTTTTTCCCC AAATATGTTT AAATAATCTC
8251 CTAACAGCCC CTGTAAAGCA AATGACTATG TATAGACAAA ATATGGAGAA
8301 ATAGAAAGAA CTATGCATTG TAGAAGTGAG AAGCCATCCA GAAGAAAAAC
8351 AGACTAATAG CACCTTCTTA ACTTCGTCTA TTTGTCAGCC TTCAACCAAA
8401 GAACAGATTG GATCCATCAC AGCTTTTGTA ATATCCCATA AGAAAAGGCA
8451 TAAAAGAGAG AAGTATCTAC TTCCAGGTTG GACTATTAAA AGCATATTAT
8501 ATAATAATGT TCAAAATGAT GGAAATGTAA TTAATTGAAT CATTTTTTAA
8551 CGGAGTACAA TGTACTCATT CAAAATGAGG ATATATTTAT TGACACAGAA
8601 AGATAGAAAA ATTTTACAAA AATGTATGTA AAGTGTGACC TTGTTCCTGT
8651 AAAATATGAA GTCTAGAACT TTGTTTATAA AAATCTTAAC AGGGATTATA
8701 GAGGGTGAAA ATCTACATTT TTCTCTATTC ATGCATCTAT TTTTCTAAAA
8751 ATAATCATTT TTACCTACAG AATTAAAAAA TAATAAGAGA AAAAAGATAA
8801 GTTGTCTTTA TACTTTCTCA TCTAGACTTT CAATACTTCA GTATGAAAAT
8851 ACATATTTTA GAAAGAATAA ATTGTAGTGT ATGTTTAAAT GTATCAAAGC
8901 CCTCTCTCAT CTCTTTTATA ATTTTTTCCT CACAGTTACT TTGTGAGGAG
8951 AGCCAGAAAA ATATTATTAC CATTATAATG TAAATGAGAT AATTATAACA
9001 TATGATGGAG GAAATATAAG GTGGGAGTTA AGAGATTACA TTTTTGAGAA
9051 GTTCAGAGCT ATGTTAGAAT CTTGGCTGTA CAACTTTTTA GACATCCTAC
9101 CTTGGAAAAC ATACCTGATG TCTCCATGTT TCAATTTATT AAGTCATAAA
9151 ATGTGATTAT CTTATAAGTT TATGGTGAGG ACTGCACCAT ATGTACCTAG
9201 AGCAGTGTGT TCTTATGATG TTGATAATTG TTCTTTTAGC ATAAAGTGTT
9251 GACGTGGCAA GATTCATAAA AACTAATCAG AAAAAGAACT CAAATATTCT
9301 ACCTTATTAT GCATTCGCAA TGTGTCTATA ATATTCAGGC TTAGGACTTC
9351 CAGCTCCAGC AAAATAACCC TGAGAAAAAT GAAGAAATCT GCTGTTTTGA
9401 AGTCCCACTT AGAGTTCTGG TTCACTGAAG TGTACCCGCA ATTTAAGTGT
9451 GTGCAAAGTA GGTCAGCAAA GAAGTGAACT TTGAAGTCCA GTTTTACCTA
9501 GTTGCTCCTT TATATGGGTT CAGGGTGGTT GGAGTTTTGC AGCAGTTACA
9551 TCAAGGTTAA GAAGAAGCAT GTTTTGGTCT ATTAGGTGGT CTTAGTGAGG
```

FIGURE 3, page 3 of 27

```
9601  AACTCATAAG TCTTTCCTAA CTATTGCTAT AACTTCTCAT AGGAGGCTCT
9651  GAGGAACTAA ACTCAGGGAA CAATAGAACA GAAATGACAG TTTCATTTTA
9701  TTAATAAATG CATTAATGCC CAGTGCCCTG CTGCATAGGT CTTTAGAAAA
9751  AATTGAGTTG GGACATACGA CTTGGGCTTC AGGTTTGTGT GGCATTTCTT
9801  AATTCTAAAT CTTGATCTTC CATCTAAGCA AACAAAAGAA AGAAGTGGCA
9851  GAAGAGATGG AGGACAACAG ATATGAGCTT ATGAAACAGG AGTGAGCTTA
9901  TTTTGGTGTG GTAGGGCTGA GTACCTGGAA GAGTTCCAAA TCTGAATCCT
9951  CAAAACTTGT GAATATGTTA TTTTTTATGG CCAAAAGGAC TTTGAAGATG
10001 TGGTTATGTT AAGCATCTTG AGATAGAAAG GGTATCTTGG ATTATCCAGG
10051 TGTACTCAAT GTCATCACAA GGATTCTTAT AAGAAGGAGG CAGAAGAAGT
10101 CAAGGTCAGA GGACAAGGCG ATGTGACAAT GTGATAAAGG AAGCGGAGAC
10151 TGGAGTGACA CACATTGAAG ATGGAGAAGA GGCCATAAGT CAACAAATAC
10201 AGGCAGTCAC TAGAAACTCA AAGGCAAGAA AATGGGTTTT CCCCTCAGAG
10251 GCTCCAGAAA GAATGCCACC CTTGACTTTA GCCCAGCAAA ACATATTTCA
10301 GACTATGACC TCTAGTCACA AGTAATAAGA GAATAAGTGT GTGTTGTTTT
10351 AAATCACTAA GTTCTTGGTA GTTTGTTACA GCAACAACAA GAAATGAATA
10401 CAATTGCCCA CACAGACTTA TGCAGGGAGG AGGTGACAAA AAGATAGAAA
10451 GGGATCTGGC CCACCTTATC CTTGGAAGGC AGGTTCCATT TCAGCTTATA
10501 CACTTTGCAT CTGGAGAAAA ATGTCGAGAA AGGTTAAGCT TGGTGATTCC
10551 ACTCACTGCT AAGTACAACC CAGTTGGTAT TTGGGGATTC TTGTTAGAAA
10601 GGGCAGAGTC TACCTGGACG TGGATTCAAG GTTCAGCAGT CTCCCCTTTT
10651 TCATACGGGC TTCATCTGTA TCACAGTAAC AATATGGCTT ACATTAACCC
10701 AAAGATTAAG GGAAAGTAGC ACTGCTATAG GCCAGGGCTT TCAGAAATGG
10751 GACACCTCAT GAAGCAAAAT CTCCATATTT TACTGGATGC GGACTATATC
10801 AAAATTGATG CACACAACTT CATGGGACTT TCTAGATGCA TATTGCTTTT
10851 CTGATTATAA AAGCAGTGCC CATGCACTAC TACCTGTGCA TTTACACAGA
10901 TTAACCCTGA GTCGCATTTA ATGCTTTTTA TTCTTTCAAG GATAATGGTT
10951 GAAATTTTAG TAACAGTGGA GTACAATTAA GAAAAACCCT GTTATCACTC
11001 TAACTGGGCA CTGGCATCAA AGAACAGGAG AAATAAAGAA AAAAGTAATT
11051 TTTAAAAATT TTTCTGAAAA TGCAGATTTG ACATGGCTTT TGAAACTTGA
11101 GCATTATGCT ATTTCTATTT AAAAGGTGAG ATTTTCCTTT GTGTTTGCAG
11151 TCTATATTTT CATCACACTG CAAGTGGCTG AGTCTCTACG GTTCCAAACA
11201 ATAGCTCAAC TTGTACCTTT CAAAAACATT CTTAGGAATA ACTTAGAAAT
11251 GGGTTGTCAC TCCTCTCCTC ACCGCCAGGG GTGGTCATTA GCTGAACTTA
11301 CTGAACATTT GGGGCAGTAG CAAGCACTTT GATGGCAGTA CAACCTGCAT
11351 GCAATCTATG GGTGTTTTTG GACAGAAGGC CTCAACTAGA AGCCAAACAG
11401 AAGTTGTGTT AATACTCCCC AGATTAAAAA GAAAAGTTTT TGTTTTCGTA
11451 AAGTTCAACA TTCAGCATGT CTTTGTCTAA CAGAATCACA ATCTGGCTTA
11501 GTTGTGGAGT GCTATTTTTT CAGTCCCAAC CAGACATTCT TAAACAGAGA
11551 TTCCTTTAAA CAAATAATTT GCTTCTACAT ATTGTAAATG TAATAATGGG
11601 AGCAAATATA TACACAGATC CACACACAGA GAGATGTTAT TGTGTTGCTG
11651 ATACAGGAGG AGTTAATTTG AGTCTTTTCA CACATTGTGT TATACACATA
11701 AAGAAATGCT TCAATGTGAC CTGAACATGA ATGATAAATC TAGATCCGAA
11751 TTTATCTAGT GTGCCTTCAC CTGGCCACAG ACACAGAGAG CCATCTAGTG
11801 GTCTCCAAAA TACAGCTTTA GGCTGAAGCA TCCTAGGAAT CCAGTCTCAC
11851 AAGACAAGAA AGGATTCCAA GCAGCTATTA CTTCATTCCT GGTCTTTTGA
11901 CTGTGGAAAA TGTAGATTAA TTCACCAAAA AGATCTTCTT CTGCCTTCTA
11951 CTAAGAAGTT TCATCAACTT CTGCTGTACT GCCAGCCTAT CTATAATTGC
12001 AGTTAACAAC TATAAAGTAA GATATCTCAA AATGTGTCCA GTGGGGTTGG
12051 GAGAAAAATG AGATAAAGTC TTACTAACTT TAGAAATGTA GAGTCATTAA
12101 TTCTTAGTAG CTGTATTTGC TGTCACTTTC ATTCATAAGG AAAGATAAAG
12151 AGATGCAGCC ATTTTATTGT GCTAAGCACA TCATTTATTC CTTTATTTCT
12201 GATTATAAAA AAATCTATGC TCTTTGTGGA TAATTCTAAG ATTTAATAAA
12251 ATGCCAAAGA ATCCAAATCA CCTATAAATA CACAACCAAA AGATCTACTC
12301 ATATATGTGT GTTATAAAAT TGGGGCCATC CTACTTTATG GATTTCCCTA
12351 ACATATTCAT ACATTATAAA CCGCTTCTCA TATCGCAAAT ATTTTTCTCC
12401 ATTATTTGTA ATGGCTAGAT AGTTTGCCTT TGAATGGGTT ATTTCTTGGT
12451 TTGTTTACCT AGCCCTTGCT GTTTAAAATC AGATTTGCTT CCATTAAAAA
12501 AGAAAAAACA CTGTTACCGA AGGGATTTTA CTACACTCAT CTTAGCATTT
12551 TTGTAGTTAC TTGTGCTGCA GAACACCCTC TACTTGAGTT TTGTGACACC
12601 GTCATTGTTT TCCTTGTTTT TTTCCCCTGT CCTTTCATTG TCTTTTACTG
12651 ATTATGCTTC TTGTCCTTGA TCCCTTATAA TAATCACCAT TGTACTGTGC
12701 TGTCTAATAT TATAGCCTCT ACCCAAATAT GGATACTTGA ATTTAAATTA
12751 AGATTACATA AAATTTGAGT CAGTTTCTCA AGCACATGAA TCACATTTCA
```

FIGURE 3, page 4 of 27

```
12801  AGTGTTTAAA ACATCTTATG TACCCCATAA ATATATATGC CTACTATGTA
12851  CCCACAAAAA TAAAAAACTT TTTAAAAATT TAAATTTAAA TTTAAAATAA
12901  ATAAATTTTA AAAATATAAA TTTTAAAAAT TTTTAAATAA AATATTTTTT
12951  TAATTTTAAA TAAAAATTTT TAAATGGGAA CATATGGGTA GTGACTTCTA
13001  TATTGGACAA CATAGATATA GAACATTTTC ATTTCCATAG GAAGTTCTAT
13051  TGGATTGTTA TGTCAAAGGA TGTTCTGTTG CAAAGGAAGA GAAACTCCCA
13101  CCATGAAGCT CAAAAGCAGG GAATTTGTGC TGAAATCTTA CAGGAAAATG
13151  ACATGAAATA GAAATGCATG AAGTATAGCT GAGCTGTACC ACCAGAAGGT
13201  GTTTGGGTAG CACCTCTCTT TTTCCCTTGC TCTGGGGCCC AATGGCTCTT
13251  CTCTCAGTTT CTCACTTCAC ATCTGCTACA AACTCCTCTC GGGATACCAG
13301  CTGATTCTTC TGCCTTGCCA TAGCTTCTCC ATGGATGTGG TTCTTATGAT
13351  AGGACTTAGC CTGACTCTAT ATGACTTTAC AACTCTAATC AATTTATCTG
13401  ACTACATTTC TTATATCTCT TAGTTCAAAT TATCCAGATA TCTGATTGGT
13451  TTAACCCACA TTGGTTTCCC CTCACCCCAA ATTATATGTC CTCCCTTAAT
13501  CCAATCAGAA AGGCCCAGAT TCTTAGGTTG CATGCTCAAT ATGAGACTGA
13551  CTGAAAATAC AGCAGTAAAT AAAATAGCAA AGCCCAGGCT CTCAAAGAAC
13601  TCCCATTCTA GCAGGGAAGA TAGAAAATAA GACATGCAAA CAAATAAATA
13651  CGTAATATAT TATTATTAGA CAGAGACAAG TGCAATGGAG AAAAATACAG
13701  CAGAATATAA GATTAGAGAC TGACTACAGA TGGTAAAGTA AGGTCTGTCT
13751  GACCATGGCA TTTGAGCAGA GAATGAAGTA AGGAGTGACC CATAAAATCT
13801  TCCAAGGAAG GAGCATTGCA AGCCAGGCCA ACATAAAATA AAAAGACCCT
13851  GAGATAGGAA TGAGCACAGT AATAAATAAT TGTTGAATAA GGGGACTATT
13901  CTTAGTACTA TCCATAACAC AATTTTTAGT GGGCACTGTT TCAAAGGAGG
13951  TATCAATAGT GAACCAATAA CCAGATCTAG TACACCCTTT CATACAGGCC
14001  TTTTCCATAG TGTCAACTAC TGAATTTATC TCTTTGTGTG TGGCAAGGCC
14051  AGGAATTTCT AACTTGAAAT TGTGGTTATA TCTCCAATTC TCACCTTAAG
14101  TTAAAAATAC TTAAAGATGT CTTGAAAAAG TGTTTTTCTC TTACCTATAA
14151  CAAGACTTTT CATAACATCT TTGACTTCTC CCTTTTCTTG TTACCAGGTT
14201  CTGTTGCTTT CCTTCATATA TTTCTCATAG CCCCATTCTT CCTTCTTATT
14251  GTCACATTAC CTTCTTGCAT CAATTCTTTT GAATAGCCTT TTAATATCTA
14301  GCTTCTTTCC ACCAGACCAT TCTGCACACT GCTGCTAGAT AAATTTTCTT
14351  AAAGCAATTT TTATTCTTTC ATTCATTCAA GAAATACTTA TCAAATATAA
14401  TGCCCTGAGC TTCATGCCAT TCCCTTGCTC AAAAACTATT TTACTATAAT
14451  AATATTCCCT TTCTTTTTCC ATGACCCAAC ACTTCTGTGG GGTGAAATAC
14501  ACACCTTAAT AACAATGACT CACTACAGCA TTAATTCACA AAATTGGAGT
14551  GGGGTGTGCC ACACTCAAGA AACTGTATTA AATTATCTAG ATTTTGAGAG
14601  TATAATTCAA TAAAGCATTC CATCTCCTAC TGACATGCCG AGATTCAGAC
14651  ATGTTCCCCA TAAAGCCAGA GAAATATAGG TTAATAATCA TCAGCAAGTT
14701  ATAGAATCTG GCCCTCAAGG CCATCCACAA ACATGTACTG TATTAGTTCA
14751  TTTTCACATG CTGATGAAGA CATACCCAAG ACTGGGAAGA AAAGGAGATT
14801  TAATTGGACT TACAGTTCTA CATGGCTGGG GAGGCCTCAG AATCACAGCC
14851  GGAGGTGAAA GGCACTTCTT ACATGGTGGC AACTAGAGAA AATGAGGAAG
14901  AAGCAAAAGC GGAAAACCCC TGATAAACTC ATCACATCTT GTAAGACTCA
14951  TTCACTATCA CTAGAATAGA ATGGGAAAAC TGGCCCCCAT GATTCAATTA
15001  CCTCCCTCTG GGTCCCTCCC ACAACACATG GGAATCCAGG CAGATACAAT
15051  TCAAGTTGAG ATTTGGGTGG AGACACAGCC AAACCATATC ATGTACTCTT
15101  TCCAATTCAT GGCATTCTGT TGAGATATAG GTACACAGAA AGCACAGAAT
15151  TTCTTTTGTT TTACTTCTAT TTTAAGTTCA GAGGTACACA CGCAGGTTTG
15201  TTACATAGGT AAACTTGTGT CACAGGAGTC TGTTGTACAG ATTATTTCAT
15251  CACCCATGTA TTGAGCCTAG TTTTCATTAT TTTTTCTGAT CCTCTCCCTC
15301  CTCCCACTCT TCACCCTCTA GTAGGCTCCA GAGTCTATTG TTCCCCTCTA
15351  TGTTTCCATG AGAAAGCACA AAATTTCTAG AAACAGAAAT GTGTGTATGA
15401  TTTTTTAATC AATACATATA AATCATTATA TTAAAAAGCA TTTTTCTATT
15451  ATATATCTAT ATGGAAAGAC GGATATATAC CCAAGTTGTC ACAATTTGCA
15501  GATGAATTAT GCTCTAATTC AAAATTGATT TTTCCATTGA AACAATGTTA
15551  TCTGTTCTTG TTAAGACCTC AGGCCAGGCC TCAAAAGCCT ATTTGACCCA
15601  TTGTATAGCA GAGTTCTGGT ATTAATAATT CTATAGACAC TAAACATCAT
15651  CTGTAACAGA CTCTTTCTGT TTGAGACCAA GGGGATATGG AGTCGGGAGG
15701  AGAACCAGAG ACCTGATTTC AAGTTTGGTT TTAGAATCAT CTGTAGAGCT
15751  TTGGGAAACT TCTCTGAGCC TCAGTTTATA AATAGTCATT CATTAAACTG
15801  GTTTTTATTG AGAGCCTACT GTGCCATTTA AAAAACTTAA TACAGACTTC
15851  AGTGAATTAA TACACATAAA AGCACTTTAT AAATTCAAAT TTTAAAAATA
15901  GATGAGAGGC ATTGTTATTG AAACATCTTC AGGAAAACAT ACTCCTAGCT
15951  TCAATTCTGG AAAGTTAGGA CCTATCTTCC TTGGTACTAA TTTGGCAACA
```

FIGURE 3, page 5 of 27

```
16001  GGAACAACCC ACCCTTGTTT CATCCTCCTG CAATGGACCA ACACAGTCAA
16051  ACTGTAACTT CTAAATGGTC AGCAGCAGCT GGAAGGGGAG GAAAAAAGAG
16101  CAGGGTTTCA TAATTCCCAA ACGGGGACTT AAAAAGTGTG TTTATCTTGG
16151  ATGCTCCCAT GGTCAGGGAG AAGAACCCAG GGTGCTCGGC TGTTCACCTT
16201  AGGCCTGAGG AGGAAGAAGG GAAGTTGGGG AGCCATCAGG ATAGGAGGAC
16251  TACAGCCAGA ACACAGATGA GAATAAGAGA CACTTGGGAA GTCAAGTATT
16301  AAAGCTAGGA TTGCTAGTTT ATATTCATAA AAATATATTA GTTAAGATTT
16351  AAGATTGCAT CAGTTTCTAA ATAGTACTGG GTAGTGGGTT GAAATACTGG
16401  AAATGATCAT ATCCTATTCA TAACCTATGA AGCTTACTTC ATTCCAACTC
16451  TGTCTTTAAC ACTTGCAGGG CAGCAGCCAC TTAAAGTCCT TTGCATCTCC
16501  AGCTTTCAGA ACTACTTCAG GATTTAGCCC TGAGCTCAAG CCAGGGGAAC
16551  CATTAGGTTC TCCTTGCAGA ATGAGAGGGG GAAGTAACTC TAGGAGAGAT
16601  CAGTAATAAA TCAGTAAGCT TAACCATGGC CATACCATCT CTGCCTACAG
16651  TATTTCAATG GCTCCTAACT GACTTAAGAG GCCATTGAAA CACTGAAATT
16701  TAAATGGCCT CCTAACCCAT CCTTTACCAC CTTTTTTTTT TTTTTTTTAA
16751  GATGGAGTCT CACACTGTTG CCTGGGCTGG AGTGCAGTGG TGCAATCTCA
16801  GCTCACTGCA ACTTCTGCCT CCCAGGTTCA AACGATTCTC CTCTCTCAGC
16851  CTCCTGAGTA GCTGGAATTA CAGGCGCATG CCACCACACC CGGCGAATTT
16901  TGTCGTATTT TTATTAGAGA AGGGGTTTGA CTATGTTGGC CAGGCTGGTC
16951  TCAAACTCCT GACCTTGTGA TCCGCCCGCT TCGGCCTCCC AAAGTGCTGG
17001  GATTTCAGGC ATGAGCCACT GCGCCCGGCC CACCACTTCT ATTCTCTTGT
17051  CCCAGCTTCT GTCAGAAAAA GAATCGGTGT ACTAACCTGC TTAAACCCCT
17101  AAATGGCAGC AGTATGTCCC AAACTTCAGG CATTCAGTTA CTGCCCTCAT
17151  AATTTTTGCC ATATCTCTGC ATCATCTACT GCTATTAATG TTTTAAATTA
17201  ACTTGTTGTT TTACCTAAAT AAATTCACTT TTAAAAATCT TTTCATGACA
17251  ACATTAATGA AATACCAGTA CCATTTGCCA TAAATAGAAA TTAACTATAA
17301  AAATAAATAC ACAATAAAAA CTAAACAGTT CTAGCTAGGT ACCCTTGCCT
17351  GCCTGAGGTC TGAATCTGAG TACTTTTTTA AAAGAGGAAA TTTCTAGGTG
17401  CTATAAAAGT GTTAAAGACA CGCTGACACC AAACTGAGGC TTTCTGCTTA
17451  AGTAAACAGA TGGATTAAAT GCTAATTGAA AAGGAATTAA GTTTCTCACT
17501  ATGTGATTCA GTGTTATATT AATGTAAAGT TTCTGAACAA CCTAAAATCA
17551  TCTCATGAAT CACCTACACT CTGCCAAACA GTAACCTATA AGGTGAATTC
17601  TAAGCAGCTT AGCGTAGCAT TCAAGACCCT TCATTATCTG ATCCTCACAT
17651  CACTCCTCTC CTCATTTATT CTTCATACTA ACACTTGCCC TTTGTACTTT
17701  GTGCTCCAGT AATGCCTAAA TGTGGAATAC TATTCCAAGC ATATGCACAT
17751  GTTGTTCTCA CTGCTTGGCA TACCATTTTC CCTTGTGTCT GCCTGAAATT
17801  CAATCTTCAT CCTTTGCTCT TCTGTGCATG GTACACTGGC CACTCTCTCC
17851  CTACCATGAT TGACAACTTT CACTTCTATG TGACTTTTCT ACGGTCATCT
17901  TTCTAGATCT GTCATACAGT TATGTAATTA TTTGTTAACA TGTGTCTCTC
17951  TCCTCCTCTC TCACTAGACC AAACCCTGTG CTCCTCACAC AATGTCTGGC
18001  TCATAATAGA TGCTCAATGA CTATTGGTTA AACTGAATTA ATGGTCCACT
18051  TTCATTCATT CTAGTGTAAC TGCTAAATCA CACCTGTGGA AAACCCACCA
18101  TATGTCAAGG TATGGTGATG GGAACCTAAA AGAGTGCAAG GCCCTGTGAA
18151  AGAGGGTCCT CATTCACTGC GGTGGACAGA ACTCCTGACC ACCTAGAATT
18201  TACCATGTTA TAAGATGTAG AACAAAGCTG GAAAAGTAAG GCCTTGGGGA
18251  AATTGATTTT GTAATAAATA GAAAACCTGT TTCTACTACC CTATTAAACT
18301  TTTCCTACTT CCTTCATTCT CCCTAAATCA TTTCCAATTT GCCACAGACC
18351  ACAAATGACA GAAAGTGACA TTGTTCTCAC ATCTTTGAAC CACTGCTTTC
18401  CCAACTCCTC ATTCACCTCT TCTGCGAATT TCTCTATATT TTGTAGCCAA
18451  AGATTCTTGA CATTTAAAAT TAGAGAAAGT CAAAGTTGAT GAAAAGTAAA
18501  TTTACTGGAA ATAATCATCA GTGAGAAAGG AAAAGCCTGG AACTGTATTT
18551  TACCTTGTTA TCTCCTGTCA AACAAAGTAT CGGGAAATCA GACAAGAGTT
18601  CAGATCTTGG TAAGATTAGC CAAGTCTATT CCTAACTTCC TGTTTTACTC
18651  ACTGCTCATC CGTCATTAAG TACGACTCTT TAGGTTTCAG CCGCCGGGTG
18701  TGGTAGCCAT CTGTTTGTTA GCAGCACCCA GATAATTTCA AAATGTAGAT
18751  TCCCAGATTT ATCAAATCAG AACTCCTGAG GTTGGAGCAC AGAAATCTAT
18801  TTAAAAAGCA AACAAACAAC TTCACACACG ATCTGAGTAT CATTTGTTTT
18851  TTGTTTTTTG GACCACATTA TCCTAAGAGT GTCATCCAAC GTGATTTTCA
18901  AAATGTGACC AGGAACCACC TGGGAAAAAA AAATCACATT TGGTAGTTTT
18951  TAAAGTATAG AATTTTAACC TCACTGAATT CCACTATATT ATATGCTATG
19001  ACCTCATATA TCTGTTTTCT TTTTAACAAA CTCCTCCAGA TTATTCATAT
19051  ATGCACAGTA CAGTTTGAGA ATCAATGACC TGGGGCAGAG GTCTCCAACT
19101  CAGATGCCTT CTAGAGGCCA TGAAGGTAAT GGAAATGTCC AAAACAGTCC
19151  CAAATAATAC AGTAGGGAGT AGTGATATCG TATGTCACTG AAGAGTGCCT
```

FIGURE 3, page 6 of 27

```
19201 GGCCTTTCTA CAGCAGCCAG CCAGCTACTA CTCAGCTGCA ACCAGCTGTT
19251 ACTCACAGGG AACATTGCCA GATATTCTGA CTTTTCAAGG GAAGCCAGAC
19301 TGGATTTTTT TAATGTAAAA ATCCCCTTAA ATGTTGACAA CTTACTCACT
19351 TTTTAAAAAA CAAACTGCAT GCCTGCTAGT GCTGGAGGGT CACCAGTTCA
19401 ACACCTTCTG GACTAGGAAA TATCAAGGGA TTTGTAAAGC AGACAAGTAT
19451 TAGCCAGAAA CGCCTCACTG CCTGGCTGAG TAATGGAAGA TGGCATAGGA
19501 TAGGCCTGTA ATCATAACAA GTACAGTTCC TTTAAGGTAC AGCTAGAAAG
19551 AGCTAGAATA AGTATATAAT GTAAAGGACA GGTGGATACC CTCATGTGAA
19601 AGCAAGAGAC AAGAAAGAAA AAAGGCTCTA AAAGATAATG AATATAATCC
19651 ATTCTATTCA TAACATGCCC ATAAATGAAG TTTAGAAAAC CTTACTCATA
19701 AAATAGAAAT AATGAGATAA TGATAACTAC TCATAGTGTT TGAGGTATTA
19751 ATTAAATAGA ATAGCTTATA TCAAGTGGAT TAATGACAGC AACTGACATG
19801 TAATATGTAT TCAATTTTTT TAAATGTGAG TTCTTTATTT TCTGTTTCCT
19851 CAGGCTTCTG TTCCCTCACA CTAAAATTCA AGAGGCACTA AAGAAAAGCA
19901 ATCTCATGGC AAAAAGCTAA CACACTTTCT TAATTTCCAT GTGTGTGTTT
19951 AAAAAAAAAC TGACATTTCT ATGTGATAAT TAACAAGATT GTGATGACAA
20001 AGCCATTCAG TCCCCTCATT GTCCTTTCCT CTAATTCTGC TCTTCCTTCC
20051 ACTCTTTAGT GTTTCCAAAT TCCATGCGAA AAAAGTTGCT AAATAAATGG
20101 ACTTGAGAAT TCTTCTGGAT GATTTGGAAA AAGTGGATAA AGTCTGGGCT
20151 ACATTGCTCT AGAAAGATTG CTTTCATTTT ATTGCATTCT TGATATATCT
20201 ACTTTTTTAA AATATAATAA TTTGTATATA AAAACAATGT AATGGTGATG
20251 TTTAAAAATG TATTTACAAG GCAAAAGATT CACAGTTTCA CCACCTTAAC
20301 ATATATTTCC TTCCAATTTT TGTTTTTCTG GGAGGTTATT GTTTTCTGTT
20351 TTATTTGCCA TTGTAATTCA AGGGTCTATT ACACTGTTTT GCTCATAGTA
20401 ATCACTCAGA TATTTGTTAA GGAATGAATG AATGAACTCC TGAAATTGTC
20451 ATGTACAACT GACTTTGTTT TCTACTTGCT CACTTTCATT ATGTCATGAA
20501 ACTTTTATGA GTCTCCACAG ACTTCAAATG AATCATATCT CTCTACCTGT
20551 TTTGCTGATT TTTTTTCTAA TGATAAAAAT CAAAAAAATG TGAAACTTTA
20601 GAAAAGAAAT TTTAATCCCA CTATCCAGAG ACAATCACTC TTAATTTGTT
20651 GAGATATTTT ATCCTAGCAT TTGTTACATA AAACTTTTTC TTTAAACATG
20701 GAGAATTTTG AACTCCTAGC CTTAAGATGC TCCCATTTTC AGCCTCCCAA
20751 AGTGCTAGGA TTATAGGCAT GAGCCACCAT GCCCAGCCTT AAACATGGAG
20801 AATTTCTATT TAGATTATTT CATTTAATAT GGCATTGCCA GTATTTCCCA
20851 TGTAATGGGA CGCCCATGGT CCACCCACAC CATTATTTTA TTAACTGCTT
20901 ATTATTCCAG GCTCTTGGAT ATGCATAGAA TGTTCACATT TTCTTTTTTT
20951 TTTTTTTTTT TTTTACCATT TTTGTCACAA AATGTCCCAT GATAAAGGTC
21001 TTTATTCACA GGCTCTTATT TCCTTATCAT ACATTCCTGG AAGAGGAAAA
21051 TAATACTAGT TGATTGAAGA ATGTCCAAGG ATCCTTTTCA TATTGAGTAT
21101 ATGAATGGCA TATTTTCCAC ATCCTTATGT ATTCCAGCCT GTCTTTGTTA
21151 TTTTTCTTAA AAATAAAAGA CAGATTGACA GGGCATAAAA TTCTTTCCCA
21201 AATAAACTCA CTTAGATATC ACTTTATGAT CATTGGACAT TTAATGTAGC
21251 AGAACTGAGA AGCCCATGAT ATTTACATTT ATCCCTTTGA AGATCACCTT
21301 TTTAGTTTTC TTTCTTCCAA AATATTTGAC AGTTTTTCTA ATTAAAACAT
21351 TTTGTCAGAC ATGTCTATGA ATAGTTCATT TGCATTGATT TTGTCAAGAT
21401 TAATTTGGGT CCATCAAATT GACATTTTTT TTAATCCCAG AAAAAAATTT
21451 ATCTTGATGT ATTTTTCACT AGCACTTCTG TTTTTGTAAT GGCTTCTTTC
21501 TTAGGGGCAT AATTCTTAGG TTGGGGTTCT CTTGTTTATC CCCTATACAT
21551 CAGGTGGCCA AATAGTTTAT ATCCAACCAG AAAAATTTGA AAATGAAAAG
21601 GGAGAAGTGC TAATAACTAC AGGGGACAAT AGGAATAAAA GAGGAGCTGT
21651 CTGAGTTCTA ACTGACACAC ACAGCCACTT TCCCCTCTTT TCTCTCACTA
21701 TTTATAGTTG TTGATCCTTT TGTTCTATAT CCTGTAAGAT TTTCTTAATT
21751 TTGTCTTCCA CTTCACTAAT TCAATGTTTG CAATATTTGC CAAGCTTTTT
21801 ATGTTTCCAA AGCATAATTT GAAATCTATT ATTGGATTTA CTTTTCCTGT
21851 TTCTTTCCAT ATCACACTTT CTTTTCATTC CATCCTATTA TTGTCTATCT
21901 CAGCATGTTC TCTAGTGAAT TTTTCATGTT TCATAAAAAT CAAATTATCC
21951 TGCTTGTTAT GTAAATGTCA GGGTTTTTCT TTTCCAATTT TCTTTTGGCT
22001 TCTAAAGTAA ATCGTTTTCA TAATGCGTCC TTTATTTTCT TTGCCTTGTT
22051 CTACAGCGTT TAGTTTCTTT GCCTTTTTCT ATACCATTTG TAAGGGCCCA
22101 TGTTGCTTCC TTGTTTTGTT TTTAATTTTT ATTTTTCAGA AACAGGATCT
22151 TACTCTGTTG CACAGACTGG AGTGCAGTGC CACAGTCAGA ATTCACTGAA
22201 ACTCCTGGGC TCAAGGGCTA ATTTTTTGTT TTTACTTTTT ATTTTTGTTT
22251 TGTAGAGATG GGGGCTCCAC TCTGTTGCCC AGTCTGGTCT TGAACTCCTG
22301 GCATCAAGCA ATCCTCCCAC CTCTGCCTCC CAAAGTGCTG GGATTACAGG
22351 TGTGAGGCAC CATACCCAGT CTTGGTTTTG GTTTTAATTG GCGGGAAGAA
```

FIGURE 3, page 7 of 27

```
22401  TTCTTATTCT AAAAACAATA AGGAACCCAT CCATACCCTC TGTTTACCAA
22451  CCAATAGGCT ACTTGGACTG CACCGTCTAA CTTAGGATTC ACTTATGTGC
22501  TAGCTAAATC CCCTTCTAAT AAATGCAGAT AGACACTAAG TTACCAAGCA
22551  CATTGCCTAA ACCAAATCCC AGTTGTCAGC AGCCATCAGG CATGTGGTGT
22601  GATTCTGGGT AACCCAAGCT GGAATTTATT TATCCTCTGC TGCATTGCTT
22651  TCTGATACAC AGTTCCTCTA CCTAGTCATC TTTTACTGAA TACATACCTA
22701  GGCTCTATCC TAGACTTCCT GGTTCAAAAT CTTAGAAGGC ATCAGCTTGT
22751  GTATGTAACA AATTTCCCAG GTGTTTCTGA TATGCCCTTT TTGCTGGGAA
22801  TCACTGATCT GAACCAATCA AGTACATTTA AAAATAACAC AGCTGTCAGT
22851  TCCATGTCTG CTGGGGTGAA TGTCTAATTC TTCTACCTCC TATGGTGTTT
22901  TTCCTGTGGG AATTAAACCT CTCCCAAACA CGTTCTTCTT GGAGATGCCT
22951  ATATTAAATA ATAAAAATGT TCATCAGGGC GGAGAAGTGA TTGAATGTCA
23001  TTCTGACTGC CCCAGAAAGC AGAGCCCATG CAGTAGAGGA GCTCTAGTGA
23051  CTTTTCCAAT TGAACTAAAT GGCCGAAGGA AAGGGATGGA AGTCTTTAAA
23101  GGAATTAAGA GCCAGAAGAC CCAGATTACC TGGGTTTGAA TCCCATCTCT
23151  GCCAATTACT AGTGGAATGC AATGATTAAG TCACCTAAGC TCTCTATGCC
23201  TTAGTTTCCT CATTCACAAA GATAGGAATC TTAATCTTAA TCTTTTCTCA
23251  TCCCATAAGA TAGAAATAAT AGGATCTGTC TCATTGAGTT TTAATAAGGA
23301  TTAAATGAAA TAATTTCTAT GAAGTGTTAA GAATTGCCTT GTCCATAATA
23351  AGTGTTTCCA GGAATATTAG TTATATCATT GTTACATGGA ATAACGATCT
23401  CATATTTTTT ATTCTGTTTC CACTAGCTGG TAGTTTGTGC AATATCCTTC
23451  TGTTCTAGCA ATAAGCTGAT TATTAGTAGA TGTTTTTAGA GTGGTGAGCT
23501  TTCATATTTT TGTGTCTTAT TTGATATTTT ACTGGGAAGT TGAGAGGCAC
23551  TTCATCAGAT CAGTTCCTGC ATTTTATTGG AATCTTATGG ATGAGTTCTA
23601  GAATGGTGAT CCATCACTGT AATTTGGGGT TGAACAAGAA GTCAGTCATT
23651  TCATTTCCAT CCAGGCTTTC CCACCATTTC CTACTCACTG CCTTGTCTAC
23701  CTCATTTGTT CTTCCACTTA GTTCTGTAAC TTTGAAGCAG CTCTGAAGTA
23751  CAGTGAAACC CATGACCTGG TTTGAAGCTA GTGAAGTCCA GGAAGAATTG
23801  CACTCTGTAG TTCAAAAGGC TCTTCTGGGT GATAGTCATT AAGAGAGAAA
23851  TTTAGTGCAA AATCAAGATC TTTCTAGGTT TTCCAAGTAA TTAATTAAAC
23901  CATCAGATAG TAAGTGTATT GGTGAGACTT AGTCAGTTAT TTGAAGAGTG
23951  AAATTTTAAT GAAAAGAATT GTTAATTAAG TACAAACTTG TCAATTAGGT
24001  AGTTGGAAGG ATAATAGGAG AACTTTATGA TATCGTGAAT TTAAATTCTC
24051  CAAGCAGTTG CCATTCATTG AGCTGAGGAA AGAACAAGAG ACTGGAAATA
24101  GAAATATTTA GAGGCTTAGA GGGGTAGCCC CATAAAGCTG AAATTCAGGC
24151  ATCTGAGGAA AAGGGGTGTT GCTCAGCTGG TGATGGAATC GTTGAGCTCC
24201  AAGGAGGGAA CCTAAAGAGC TCAGGTTCAG ACCTTTACCC TGCTGGTTGA
24251  TGGTATCTCC GAGGGCACGG AATAAAGTGG TTCTACAAAT ATTGAAAAAT
24301  AGCTACTGTC TCTCATTAAA GATTTTTTGA AAGTCGAGAC TTGGAGCCTT
24351  AATTATCTTA GCTCTCTAGT TTCCATTCAC CCACCCCTAC TCTGTCCAGC
24401  TTTCCAATGC TCATTTCGCT ATCAATTATC TCCAGTTTTG AAAGACAGCA
24451  CTAGATTCCG CCACTGCCCT GGAAAAGAAC CACTAACAAG TTGAAGAAGT
24501  ATTGCTGGGG TGATGCTTAC AGGAACCTAG AGCAGTCAGG TAACCCACAG
24551  AAAGCAAATC AAAGACAGAA AAGACAGACA AGAAGCAGCA AACCCTTTCT
24601  CTTCCTTCAG TCTTGCAGTC TCCCCCTAGT GGCCTCTACT GGCAAAGCCC
24651  ACCAGAACCA GAAACGTAAT GGGTGGAATA CAGTAGTCTC CCCTCTTCAA
24701  GGTTTTGCTT TCCAAGGTTT CAGTTACCCA TAGTCAACCG AAAATAAACA
24751  ATTCATAAGT TTTCCATTGG ACGCTATTCT GAGTATCATG ATGAAATCTC
24801  CCACCGTCCC ACCCTGACCT ATCGGGATGT GTGAATCATC CCTTCGGTCA
24851  GTGAATCCGG GCTGTATGCA CTACCCGCCT GTTGGTTATC AGCATCATCT
24901  GCCCCTGACA TCCAACCATA GATGTCATCA TGGCTCGATG ATCCAGGATC
24951  TCCCAAAGCA GATGGTCCTC CTGACATATG GTCAGAAGTT CAGTAGTAGC
25001  CTAATGCTCT GTGACAATGC CAATGCCATT CACCTCACTT CATCTCATCA
25051  CATAGGGATC TTATCATCTT ACATTATCAC AAGAAGGACG AGGGTGAGTA
25101  CAGTACAGTA AGATATTTTA AGAGAGAGAG GCCACATTCA CAAAACTTTT
25151  ATTACAGTAT ATTGTTATAT TGTCCTATTT TGTTATTAGT TATTGTTATT
25201  AATCTCTTCA ATTAATTTAT AAATTGAATT TTATTATATG TATGTATATG
25251  AGAAAACATA GCATAACTGC TCAGAGCTGT GGAGACTGCA ATTTTCCAAT
25301  TCATCTGAAC TAAACAGTCA AAATCAGACA ATTCAAACTT TAGAAGAAAT
25351  CTATTAATGT GAATGATTTG CTTTAGCCAT CTGCTTTGTC ATTCAGAGTG
25401  CCTAAAACCA TGTCTGGTTG CCAGTCAACT CTGTACCACA TAATGTTACC
25451  ATAATTGTTT GGCAAAATTT CTACCTGGGA TACCTCATCA CCAGAGGTTG
25501  ACTTTTCTCA GTCGTCCCTC CCTTAGGAAA GCAACTTGAG TAAACTGATT
25551  ATATAATTTT GCCATAAATA GAAATCCCTG AGTTACAACA TGAATCCACA
```

FIGURE 3, page 8 of 27

25601 GAACAGGGTG GAAATTGGAA GGTATCAGCC TATTGCAGAT CTCTAAACTA
25651 GAGGAGATCT CCATCCAAAC ACTAAATTCT TACCCTTGAA TATGGACTTG
25701 GGGCATCAGT CATCTGCCAA ATCTTAATAT ATACATTGAT GCCACTGATG
25751 TCTGCAAAAG ATTACCAGTA TTTGCATATA CTTGACATTC TCTATACAAC
25801 AAGTGAATTT TTATGTTAAT TTGTATGTAT GCATGAGACT CAGTAAGAAT
25851 TCTCCAAAAT AGAAAGATTT GTTGGAATAC CAAATAGCTA CTATCTGTCA
25901 TTTAAGATTT TTTGATAGTT GAGACTTAGA GCCTTAATTA TCTTAGCTCC
25951 CCAGTTTCCA CCCACCCATC TCTACCCTGC CTAGACTCCC AGTGATCATT
26001 TACCTATAAT TACCTCTCCT GTTCTTAAAG ACTGAACTGA TACTGTCCAT
26051 ACTTCAAATC TAATCTCTGT ATTTTCTTCT CCCGGACCCC AAAATCACTG
26101 AGATTCACCC GGAGTTCTCT AAAACAGGAT TTCCAGGAAA AACAATTTAG
26151 AGAATAACAG TAAAAGAGAC CAATTTTATG TAGAATAGGT TTACGTTCAA
26201 GGCATCCAAG CAACACTTTT TGAAATGTTC TTTAAGCCAT CATGTTGATA
26251 GATCATAAAA TGACATCTAT CATTCTCTGA GACTTTCATA ACTGAAAAAG
26301 GAATAAATGC AGTGTAGAGT CAGGCTAGAG TGTTTCACTT CCTTGGGGCC
26351 TTGGGTACTT GTATAATAAT TTTTAAAACA TTTTTGTACT TGTGTAATAA
26401 AAATAATCAC TCACCTTGAT ATGCATTTTA CAATTTGCAA AGTAATTTCA
26451 GTCACTTAAC CTTGCATATA CGTAAAAACC TAAAACAACT TTGAGAGGAA
26501 GGTATTATTC TCCCAAATTA CAAATGAACA AACTGAGCGT TGGGTAATTT
26551 ATTTTACCGA GCAAGTAAAA AAATAAAATT TTCTGATTTT AAGTCCAGTT
26601 CTCTCTCCTC TAAATCACTA CAGATGCAGA GGTCCTTCTG AGAACTTAGA
26651 CGGCAGCGTG AGCTGCTACA ACATCAACTA TGGAATTCGT AGGTCCTAAC
26701 TTCCCTCCTG ACACATTAAT AACCAGGCTC TGCTGCCTCC ACAAAACCAA
26751 GTGTATTCTA CCAAAGGTCC CATAAGCAGA AAATTGTACT CTGTTTCAAT
26801 AAATGGTATA TTTTTTAAAG CTGCCTTTAG ATTACCCCCT TAGCACCTTG
26851 AAACTGTATT TATTATCATC TGAAGCTGGT GACATAGATA AATAATGAAT
26901 CTTATTTCTT ACCAGAAAAG GTCATTTGAA TTTTCTGAGA CCTATTTGAC
26951 CTCAAATACA CATTAACATA TTTATCATTA GCTTCCTTTA TCATGTCCGG
27001 CCTCTAGAAA TGGGTAAGCA TCTCATCTTC CTAGAAAAAT TCAATTTCAA
27051 AAGAGAAGAA AAAAAAAACA AAGAGTTAGA ATACAGGTTA TGGCTAGGAA
27101 AATGTGAGCA GGCTGTTTAA AGAGTGAGTC CATTGCCAAG GGTCATAGGA
27151 ATATTTTGAA ATTGCCTGTG TGTTACTATC ATTTAGAATC CTTTCCAAAG
27201 GTTTCTGAAA ACATTTACAA GAGTTAAAGA TTCAATCTTG AGCTTTCTAC
27251 TATTGTGTGG GATTTATAAA ATATGTCCTA TGACATATTC ATATGTTGGA
27301 GGTTTACTGC GAAATTTTAT GTGACAGTCT GCAAAGTTAC TTTGAGGACT
27351 TTTGATAAAC ATCTGGGAGA TGTTAGCATA GACCTTATAA TGTGAAAGGT
27401 AGATGCTCAC TCATCTAGCA TAAAAATGTC AGGCTAGCCA TAGAAACGCA
27451 TAAGACAAAT CACTACTCCA TTATTTCTGA AGATTTATGC TTTGAACAAA
27501 GATGATAAAT TTAATTCTGG ATCTCTTAGC CAAAATGACC CATTACCATA
27551 CTTCTATTAT TTCTATAATA TAAAACAGGA ACCCCTATCA TGGGTAGGGG
27601 GATCATATAC CGTATTTTCC TAGACCACAT TTAATATNNN NNNNNNNNNN
27651 NNNNNNNNNN NNNNNNNNNN NNNNNNNNNN NNNNNNNCTG GAGTCCAGGC
27701 CCAAGCCCCG GGCCGGCCAT CCTTTTATTT TAAAAGACCC TTTTTCATAC
27751 CTCCCCTCCC AGGACAGCAG TAGACCCTTA GCATGTAATC AAGTTCTTGA
27801 AGGGGCTTCT AATTCCCCAT CCCCTGTTGA ATGCTTCCCC AGTGATGATT
27851 TTTCCCAACG CTCTGTTTTT TATCATTACA AGCTTTCCCT CAAAAGCTTA
27901 ATTTGGAAAG ACAAAAAGAC AAATTCTCAG AACAAATTTT AAGAATAAAT
27951 TTTAAGACTC CATCCTACCT ACCATCATGA GTAGCTACAG TCATAGTTTT
28001 CCTCCTGTAA ACCTCTGTGG AGTCCTCACT TTTTATTCTA CATGTATCAA
28051 AGTCATTTAA ATCCTCAGA GAGTTTAAAG TGCAGCATAA ATTCTATTTC
28101 CTATTACACA TTTTTTGGTA CGTAGGGACA GGCCACACTT CTTTGTTTCA
28151 TACAAGGGCT TGAGATTTTA CTGAGAAAGG CTTCCTCATT TCTTAATGCA
28201 TATTATTGAA TGTTCAGCAA GCTCTTAAAA GCAATCCAAT AGTTCCCAAA
28251 ATAAACATAG TTAATTCCAT CAATATTTAT TGTGCCCCTA ACGTATATAA
28301 GACATTGTGC TAAACATTGT CAGGATGTCA GATGCTTGCT CTTGAGGACA
28351 ACAATTAACA AATGTATTCA TTGGAAGACT ATTTCCACTT CAATTATATG
28401 ACTGCTAATT TGTGACTTTT CAAATAAGTT TCTCTTCTTC CATGAAGTTT
28451 GTGAATTCCA CAAGTAGATA AAATTGTGAT ACAAGTTACA TAAGTGTGTT
28501 TAATGGCACA GATTTCACTT TTCACAGCAA GAATCCAGGT TCAGAAGATA
28551 CAGAAAAGTA ATCAAGCCTT TAACATTGCA CTACACACTT AGTCTTGATG
28601 TATGTATTGA AAATTATTCT TTACTTATTA GAAGTGTCTT CCTCAAGGGG
28651 CTGGAAGTTT AGGAAACTAT GATGCATCCA TCTTTCACAT CATCCTTATA
28701 AAAATACCTG CATTTTGCTA AGATTTCCTG CCATTAATTT TAAAAAGAAA
28751 CAAAAGTAAT TTCTTCTCCT TATTGCGTAT GAGATCAAAG TTTAACAAAT

FIGURE 3, page 9 of 27

```
28801  GAGGTCTTAA TAGCGATACC AAGAAATGGG AAGCCATAAA TGAGACTGCC
28851  TATATGGCAG TAGACAAGCT TGACAAAACT CCTCAACCAA ATGTATGATT
28901  GTGTTACTTC TGATATTCAC ACCAAGAACC ATCCACCCTC TGGTACTCTT
28951  AGCAAAAATT ATTAGGAAAT CAGTTGTTAG GAATCAATAG TTCCATTAGA
29001  CAGGAAGCAT AGTTTTCCAA ACTATGGGAA TTTTATCCCA GAACTATGTA
29051  TCACAGTGAA ATTAAAGGAT TAAGCCTCAT AAGAAAGCAA AAGTACCCTA
29101  TGTTAAAGTC TTTGGCCAAT GCTTTCTAAT TCTTCTTTTT CATATCTTTA
29151  AATACAGAAT CCCCTTCACC TACAACTGAG TTTAGAAAAT TCATTAAGTT
29201  CTGATGCTGA TGTCACTGTC TCAATCCTGA CCATGAACAA CTGGTACAAT
29251  TTTAGCTTGT TGCTGTGCCA GGAAGACTGG AACATCACCG ACTTCCTCCT
29301  CCTTACCCAG AATAATTCCA AGTTCCACCT TGGTTCTATC ATCAACATCA
29351  CCGCTAACCT CCCCTCCACC CAGGACCTCT TGAGCTTCCT ACAGATCCAG
29401  CTTGAGAGTA TTAAGAACAG CACACCCACA GTGGTGATGT TTGGCTGCGA
29451  CATGGAAAGT ATCCGGCGGA TTTTCGAAAT TACAACCCAG TTTGGGGTCA
29501  TGCCCCCTGA ACTTCGTTGG GTGCTGGGAG ATTCCCAGAA TATGGAGGAA
29551  CTGAGGACAG AGGGTCTGCC CTTAGGACTC ATTGCTCATG GAAAAACAAC
29601  ACAGTCTGTC TTTGAGCACT ACGTACAAGA TGCTATGGAG CTGGTCGCAA
29651  GAGCTGTAGC CACAGCCACC ATGATCCAAC CAGAACTTGC TCTCATTCCC
29701  AGCACGATGA ACTGCATGGA GGTGGAAACT ACAAATCTCA CTTCAGGACA
29751  ATATTTATCA AGGTAGGATG CAAGGTCTCG GTTATATCCC CATTCATAGG
29801  GCCATGACAG AGAGTAAAAT TCCCCTATCT GTCCGCTTTG CAGAAATCTT
29851  GACTCTGAGT AGCTTTAAAC TTTAATAATA TTTCTTAGAG GATTTCTGGT
29901  TATATAGGCT AGTATTTCAT GATCTGCTAT CTGTAATTTG ATCTATAAAC
29951  TTGTAAGTAC ATGGTATAGT GGGAGTGCTC AATCCTGCCT TTAAACCTTG
30001  GTTTAGCTTC TTACTAGCTG TTGTGTTCTT GGAAAGTTAT TTAAAAGCTC
30051  CAAGCCTCAG TTTTCCAACT AGCAAAATAG AATAATGAAT AGCTTGGTAT
30101  AGTATAATAA AGATACCATG AAATTTATAT ATGAAAAGTA CCTAATACCA
30151  TGCTTAGCTT ATAGTAGATG CAAAATAAAT GTTTCTTTTC CTACCCACTC
30201  TTTTCCATAT CAATAAAATT AATCAAGTTT CTCTAAATCT ATACAAAGAA
30251  AAAATTAGTC AAGCAAGAAA TGGACTTTTC TCCCTCCTCC CTGGCCTTGA
30301  TGCTTAAGAC AGTATAGAGT AGTAAAGGCA AAGACTCTTG AACTCAAGTT
30351  CAGACCGTCT GAACTTGAAG TTTAGCACTG CCACTTACTA CTTGAGTGAC
30401  TTAATCAAGT TACTTAACTT CTCTGAGCCT TAATTTCCTT TGTTCTATAT
30451  TCATTTATGT AAAATGGATA TAAGAGTAGA TCCTATTACC CATAGAATCA
30501  TTGTGATTGA TGATTGATAG ATAGATAGAG ATAATAGATG ATAGATTGGT
30551  AGTAGACAAA CAGGATACAT TAATAGAACT AAGAGTTCCA TAAGAGTATT
30601  ATATATATAT AAAATATTAT TTATTTGTTT ATACATTCAT AATTATATTT
30651  GTTTATTTTT AAATTAAATA CATTTTCTGC TCCGGTTCCT CAATATGATT
30701  CAGAAACTAG AACGAAAATG TCCATTTAAA ATAGAGAACA ACACATCATA
30751  TGGAAATGGT TTTGGTGATT CCCGGGAAAG GGGGAATATC CCTTAAAGGA
30801  TATTTCATTA GGGCTTAGAC TTTCTTCTGA AAAAGGACCA CCTGTAGTCA
30851  GAGAGGCCAA GTCAGAAGAT TATTATTTCT TCAAAGACGA ATGTTTCCCT
30901  GTAGACTAGG CCCTGTTTTT AGGCCATCCT GGAACAGTGG TATCTGACTA
30951  TGTTGAGGAC TACAAGGCAA ACTCATAACT TCTTACCTTT AAAAAAGACA
31001  TGATAATGGG CAACACAGCG AGACTCCGTC TCAAAAAAAA AAAAAAAAAA
31051  AAGACATGAT AAAAGGTCAA GGGGTGCAAA TAGTTGTACA TTTAATTTTA
31101  CATATATATA TATATGTATG TATAAATTGA GCACCTACTA TGTACAAGGC
31151  AATATGCCAA ATGCCATATG TAAGGGAAAA GTGAAAGACT GAACACAACC
31201  TGTAAACTCC TTAAAGAATG TTGTTAATAA AATTTTTCAA ATATATTTAC
31251  TACAAATCTA TTAGTAATAA AATTAGATGT TCTATCATCC TCTGAACTTT
31301  CCCTTTTTCC CATATTATAA TTTCCATAAG ATTAAAATCC ATGCATATTT
31351  TATTTTATAG CCACTCTCCA GATTTAATCT ACTGTTGGCA AGCTCGCACA
31401  TAATTAAGGT TCAGAATTTT ATCTAAGACA AGAAACATTC TCCTTTACAA
31451  CAAAAATACA AGCAAAGTTT TGATTTATAA TTTCAAATAG TCATTGTTTT
31501  GGAAGGACAG TCATAAACAG CAGCCAGGAA AAACCACTTA TGAAAACTAC
31551  ATTGAGTTCC TTAGCATCTT TTTGTCTCAT GTAAAAAGGA GAATGCAAGA
31601  AAAGTGATTC TGTTTGAATC CTAAAAACGT TTAGAAACTA CAGAGAAGAA
31651  TATTTGTTGA CTTAAGTTGT ATATACCTTA GGGTCTCATT TTACCAAGAT
31701  CAGACTGATC TTTCTGGCTC CTCAAGATTT AATTTATATT AAAATTATGT
31751  TCTTCCTTCC ACAAGGATCC CATGGCATTT TGTATATAAA ATTATATAGT
31801  GGTACTTGGC CCATTCTATC CTCATTATTT GTCTGTGAAT CTGAGTTCTG
31851  AGCTAGAATA TAAATTCTGT TAAGTGGAGA CGCTATTATT GAGCCTTATC
31901  CAATGCCTAG CCTATAGTAG GCACTTAATA GGTATTTATT GAAATTGACA
31951  TAGAGGCCAG GGGCGGTGGC TCACGCCTGT AATCCCAGCA CTTTGGGAGG
```

FIGURE 3, page 10 of 27

```
32001 CCCGAGGTGG GCGGATCACG AGGTCAAGAG ATCAGACCAT CCTGGCCAAC
32051 ATGGTGAAAC CCCGTCTGCT CAAAAAAAAA AAAAAAAAAA AATTAGCTAA
32101 GCATGCTGGC ACCGCGACTG TAGTCCCAGC TACGCGGGAG GCTGATGCAG
32151 GAGAATCGCT TGAACCTGGG AGGCAGAGGT TGCAGTGAGC CGAGATCGTG
32201 CCACTGCACT CCAGCCTGGC GAGACTCCGT CACAAAAAAA AAAAGAAAGA
32251 AAGAAAGAAA GAAAGAAAAA GACAGGAAGA AGGAAAGGAA GGGGGAGGGA
32301 AGGGAAGGGG AGGGCAGGGG ATTGACATAG AAAGAAAGAA AAGTAACTTT
32351 CTGTTTTATT TACATCCTAC ATTATCTGTT GCTGTAGAAG AAATGGATAG
32401 ATGGTAGATA TTGTCTAAAT TAAGTACTTT TTAAATTTAC ATAAATACTG
32451 GATGATTTCT GTTTGGTTTT CTTTCTCTCT CGCTCTCTCT CTCTCTCTCT
32501 CTCTCTCTCT CTCACTGTCT CTCTCTCTCT CTCCTTATGG TGGGATGTTA
32551 GGTTAGTATA TAACCTCTGC CCTCGTGGCT ATTTATTCCA CAAACTTTGA
32601 AGCTGTAAAA GAAGATTGTG AGGTTTGAAG CCCAGCAGTA ATTTACACCG
32651 GGTCAGTGAC AATATTTTCA TCATGATGAA TGTGTTTGAG AAATGAACCC
32701 AAAGAACTTC AGGAAGTATA CCTGAGACTT TTTAAACTCC TGAGGGATAC
32751 AGGAAAAGAG AAAGTTTGAA AAGTATTCAG GAACAAGTCA AGGGAAATGA
32801 GCAAAACCCA GGAAGGAGAC TTTATAATGA ATAACTGAAA AGCTGCCTTA
32851 AGCCATAAAA CATCTGTGGA TTTTCCATCA TCCTTATTTA TTTTGTTTAA
32901 TACAGTCTTT CAGAAAGTAA GTTATTCTCA GTCCATAAGT CACATCTGCA
32951 TACAGTAATT TTCTTAATTG TTCTTAAATT TTGTAAGGCT GCCCCCACTT
33001 CTTCACTGCA TAATGAAAGT CGGGAGGATA ATGAGCCATG AATAGTGGAT
33051 GTCAGAGTTA CGCAAGTTTT CATTTCTCAC ACAGTCATTT TCAGTTTGGG
33101 CTGACAGAAC TGTTAACATC TTAAAATGTT AATGAAATCA CCAAAAACAG
33151 GGCATTTTCA GCTAGGCTTT CAGATTAGAA AAGTCATTTC TCATGGCAGA
33201 CTACACACAC ATAATTACAG GTATTAGAGA TTTTATTCTT CCTAGGTCCC
33251 CACATGCCAG AGCAAATGTC CATAATAACT AAATGTAGAC AAAACATTCA
33301 GGGACCAAGT TCATAGCATG ATCTTCAACA ATCTTCAACA ATATATTTAC
33351 AAGTTTTGTT TTGTTTTGTT TTTGTTTTTG AGACGGAGTC TTTCTCTGTC
33401 GCCCAGGCTG GAGTGCGGTG GCGCAATCTC GGCTCACTGC AAGCTCCGCC
33451 TCCCTGGTTC ACGCCATTCT CCTGCCTCAG CCTCCCGAGT AGCTGGGACT
33501 ACAGGCGCCC GCCACCACGC CTGGCTAATT TTTTGTATTT TTAGTAGAGA
33551 CGGGGTTTCA CCGTGTTAGC CAGGATGGTC TCGATCTCCT GACCTCATGA
33601 TCCGCCCGCC TCGGCCTCCC GAAGTGCTGG GATTACAGGC GTGAGCCACC
33651 ACGCCCAGCT ACAAGTTGTT TTTTTAAATG TTAGTTAATT GGAGCAATTA
33701 TTGGTGGAAT ATTATTTTGA GAATACCTTT ATAAGCGCAT TTGAATGGAT
33751 GTTTTTGCCT AGCCAATGAC CATGTGTTGA ACTATGGTCG GGTAGACAAA
33801 ATGAAGACTT GAATTCTGAC ATTTAGGAGC TGACAGTCTA GTGAATGAGG
33851 TCGAAATGTA AGTAAATGGT TATAAAACAA TGGGATGTGT GATTTATAAG
33901 AATAGGGATA TATTCAGATA TACAGAGGGA AATAATGAAC TCTTCTCAGA
33951 TATTTGGTGA TGAGGGAAAA ACACTGGACT TGGATCCTGT AAATGAAAAG
34001 GGGTTTTAGG TTTGGAACAA ATTCACAGAC AAAGGAAATG ACATATGCAA
34051 ATTCACCAAG ACCTGAAAGA TAAATTTAGT ATGGCTGGAG CATTAATTGC
34101 ATATGAAAAG GATTTGAGAT GATTCTGGAA AAGTAGTCAA CTTGATAACA
34151 TACCACACAG AGTTTGTATG CCAAGCTAAG GCATTTGCAT TTTATATGCA
34201 GAGCGGATGT CAACTGAATG GCAGAACATT AGCCCTGACA TATTTATAAA
34251 AATCATAATC CTGTAACAAA TTAACCAAAT AAAGTAATAC AGTATAAAAG
34301 CTTTGCAAGT AATTTTTTTT AAACATTAGG ATATAAACAT TGTTTTTATT
34351 TCTCAAAATT GCTTTTAGCN NNNNNNNNNN NNNNNNNNNN NNNNNNNNNN
34401 NNNNNNNNNN NNNNNNNNNG GATTTATTTG CCCATGCTTG CCTAAAGGCC
34451 CTAAGTGCTA ATAAATTCAT TGTTCCTGCA GAGAAAGCTC CATGGGTTGG
34501 TCATAATCTG GTCATCAACA CTTATCTTTT CTTTAAGAAT CCCAAGAGTC
34551 TGGACACTGA CAGACACATT GTTGTTCTTG GCCTAAGCAA GTCCCTAACC
34601 CTTTGACTAA TTAGCCATAG TTCTGATCGT TTATTCTAGC TTCTAATTGG
34651 GATGTAGAAT CCTCCTTTTC TTCTTTGAAC AGCTTCTGCA GTTCTGTTCT
34701 GTATCCCTTG AGAATTGAAT CAAGTAGTCA GTGATTAATT CGTTCCTTTG
34751 TTCACATGTA TTTGCTGAAA TTAACTAATA TAAGGTCAAG CCCTTGTCTG
34801 GAGACAGAAG GAATAGAAGG TAAGAGGCCG TGCTGTCAGG AAGCTAGCAA
34851 CCCCCTTCTG TTCTTCCACC AGGAGAAGAC ATGCTCATCT AATTATTCAT
34901 AGTTTTATCC ATTTTCCTTG ACCTGGCTGT TTGGTTATTA TTCTTCACTG
34951 GGATAACACC CTTTATACCA GTGATTATAC TCTGCTGGTG CTAGCATTTC
35001 TAGGCCTCCC TCCTCAGTTG ACCCTGAATT ATGATTCAAC ACACTAGAGA
35051 CTCTTTTCTC TTCAAACTAT GTTTATCTTT ATGCTTACAC AGTCAAGCAA
35101 TATCAATACT CACTGGCCTT TTATTAATAA TAAATGTTTT CATTATTGAT
35151 TCTGCATATA TTCTTAAGAA CCTATTATGT GCCAGGCATT GTGAAGAATT
```

FIGURE 3, page 11 of 27

```
35201  AGAAAATCTT CAAAAAAATG AATCAAACAA ATGTCCATTC AAAAAACCCA
35251  ACATATAAAT TGATAATCAT CACAATTTAT TCCTGAACAT TAGCAGAGTT
35301  CCAGAAGAAC TTGAGGCTGA ATGCTATAAT TCTAATTTTG GATATTCTGT
35351  CCACTGTCAC CATAACTTAG TGGCATTGTG ACCATGTTAA AGTTATTTAA
35401  ATGTCATAAA CTTTAATTTC CTTAACTATA AGGATACCTG TCTCAAAAAG
35451  TTAAGTAGTA TGTCTAAGGT CATTCAGCTA CTACTTTGCA GGGGAAGATT
35501  TAAACCAGTT TATCTAAATT CATATTCCAG GCTCTTTCAG AATTAGTATA
35551  AGCCTTCCTT AATTGGGATC CTATTACTTT TTAATTTATA TTCTTTCAGC
35601  CTGAAGCTAT ACAAATCGCA TCTGCATACA GTAATTTTCT TAATTGTTCT
35651  TAAATTTTAT AAGCATTCTT GTCCTAAGGA CCTCTACCAA CACAAACTGG
35701  TTAACCCACG TATTTCAACA TGTACTTAAA AGAAATGCAG TTGCATTAAA
35751  CATGGAAGCC AGGGGTTGGA GGCTGCTTAG CACTAGCTCC CTGGAGTCCC
35801  GAGAAGAACA CATTGCTTAT GGCTGATCCA GTATACCTAA CTCTTACTCC
35851  TAGGTTAACT TTCTCTGCTA GGGCTACTAA GGTGTTGATA CTTCTAGAAA
35901  AGACATGTTT GGGTTCATGA ATCTCAGGGA TCAACACTTA AGGTCTGTGT
35951  GTTCAGATGT TTTCAGTAGG AACCCTTGTC AGCCGAATGA TCTGGCTGGA
36001  ATTCTTTGAA ATTACCTCTA CTCCAGGTCA CTTAAGTCAT GCCAAGAGAT
36051  GAGTCTAAAA TTTTCTCTAA GTCACTGCGG GGCGGGGTCG GGGGGACTCA
36101  CATAAGGTAC ACTGGAAAAT GTATATTCCC TCAAGACTCT ATTTTGATGA
36151  ATACAGCTCA AATTTACTTA ATCTAGGATT CAGCAGATTT TAAACTGTGG
36201  AATATTTCCC AATTAGGAGA GCTTCCAAGC TTTTATGTGC CCGAGAAGGA
36251  ACTGTATTCT TGGTTGACTT TTTCACTTTA TATGCATCTA CTGTAAAATC
36301  TGGAAATCTG CCAAAAAGTA TGAAACTATG CAGAGTAATA CTGAAGCTCT
36351  ACTCTGATTT TCAGATTTAT CTCTCAAGAC CACTTCAATC TGCATACCCT
36401  ACAACCCTTA GGATAGATGT TTGACTGGTA AATACTGCAT AATGTCTTAT
36451  TGCCAGGGCT ATGCCAAGGC AATACTTGAA GGGACATCAA CACCTTGGCT
36501  AGCACTGGGG CCAGATCCAA AGAGCCAGAA TGAATTGAGT TGTGATGTTT
36551  CACAGTGTGA CCAGGAACAG TTCAAGGGCT AGGCAGAGAT CATAATTGTA
36601  TAGAAGAGTC AAGGTTCATA CCAAAAAGCA AAAGGTAAGG ACAATGATAT
36651  AGGGGTATGG AATAAATCAA ACTGTTTTAG GTAACATATC AGAGAAGAAA
36701  ACACAGAGAG AAAAAAGTGC CAGCTTGCCA GTTACAACAC ATGGAAGCAA
36751  GAAAAAGAGA TTACCATGTC TGTGTGTATG ACTTCTTGAT GTAGCAAGCC
36801  CCTCATACAC ACCAATAGTA ACACAGCACA AGACATGTAT TAAATTATGA
36851  CCCCACCACA TAGATTAGTA TTGTTCTCTT CTTGGTGAAA ACTTCAAGAA
36901  AGGTAGGAGC TCTCCTTCCA CCCTACAGTT TCACCTATAA GTAATTGAAT
36951  TTTGCAGATA TTGACAAAAC ATAGACCCAA ATGATTCATA TATGTGTACA
37001  TATATGTTTA ATATATTACT AAATTGCTGT TGACCATTAA CTGATAGAAA
37051  TATTTTTTAA AAGATGAGCC TTGTATGCAA TTTTAAAAGA TGACATAATC
37101  AGGGATTATA GCGTGCAGGG CCTTCTGTTC TGAGGATGGA AATTTAGCAA
37151  TTTCCAAACC CTATTAAACT CCTTCTCATC AGAGAGGTTC CCCATTGAAC
37201  TAACTTCAAT TTTTTATACT CTCCATTATT CAGGAGGAAA ATGTATTGAA
37251  AGTTTAATCC TTCAAACAAT TTGCAAATTA CAAATGCAAA TGTTTCCTGA
37301  CTTAATGAGC CCCATTCTTC TGGCAAAGTG ATGAAGATCA CTGTAAGAGA
37351  TACATGTCTG ATTTGAGCAG AAGACATGTG TTTAATTGCA TTTACCCCAA
37401  AACATTACTG AGCAGTTACC CTGGCCAAGC ACTGTGTTGT GCCTAAGAGT
37451  CAAAGATGAC TCAGTGAGAT AGGTACTTAG ATAAATGCTG AAGCCTCTTT
37501  CAGCTTGACA GCCTGCAGTG TTATGAAGCA GAGCAGTGGG GAAGGGAGAA
37551  CAGCAATTCT GTGGAAGATG CTGCTCTCCA AATCTGGAGT AGGTCCAAAC
37601  CCATGCCTTT GAGGGCCTTA TAGTCTAAAA AGTCAAAGAT GAGATAAATA
37651  AACTGCCAAA TTCTTCTACT TTAGGATAGT AAGAGGAGAG TCAAGGAGTC
37701  ATTTCACATG TAAGCTCAAG AAATCACGCA CATTTAATGT TTAATTTGGA
37751  GAACTGTCCC ATATGTGGAG AAGAAAATCA AACAGAATTG GACCACAGGT
37801  AAGCTCTGTG GCTAAAATGG ACAAATTCAT GTTATCATAA AAGGAAGGCA
37851  GATACCACAG GGCTCGGCTT TGGTGAAACA AGCCACAAAA TGAAAGCTGA
37901  ACTAGTAACA ACTCGCCATC AAGTACAGAA AGGTTCCCTA GGGCCGTAAG
37951  AAAAGGGAAA AATGGTAAAA GAGACATAAA AAAATAAAGG GAAGTAAATA
38001  GATGGATCTC AGAAGGCAGT GGGAAGGGAG CTGGAATGGC GACAAATAGT
38051  AAATTAACTA ACGATGGTCA AAGAGCTGCT TTAAGACAAG ATCTCCCACT
38101  AACAAGACAG AATATTGGCA TTTCTGCTAT ACAAAAACCA CTAAAAAGAA
38151  AAGGGGGAGA GGGAGGGAGA GAGAAAAACA AAAAATTCAG AAAAAATAAA
38201  ATAAAATAAA GAGTATTAAA GAAACAATGA GCCAACTGTA GATTAACCCA
38251  CATGCCAGAA ACAGTGAGAA TACTGGAGGG AAGGGAGCCA GAGGAAGAGG
38301  TGTAAAATGA GAATAATTTA GGAAATCAGA GAGTTTAGGG GAAAGCCCTG
38351  AAAAAATAAG AAATATACAC ATGGAAAAAT ACAAATGTAA ACTATGTATA
```

FIGURE 3, page 12 of 27

```
38401  GTAAATAATT CAGATAACTG GAGGTCTATG GACATTGTGA AATATCAAAA
38451  TTGGCTGTAA GAGTTCTGAA AGACAATCCA AAGAGAGAAT AGCTTAGGGC
38501  TCTTGAATGA AAAAGAGCAG AAAAAAAAAA AAGACTACGT AAGTGTGAAC
38551  TTGTGACAAA TGCAAAAGTG TAGAACTCTG GAGAATGTGA GTTTTTAATT
38601  AGAAGATTCG TCGTAGATAT GAATCACATT AAGAAAAGAT AGGATTACTG
38651  AACATCTATG TCAAGTTTCT CTTTCTCACA GAAAAAAAAA AAAGGAAAAG
38701  GGGAAGGTTT AAGAATATTC CTTTGTCTCA AATGATAAGG ACTTTATTGA
38751  GCTGGGTTTT CTACTACATG CCAATAGTTG GTAGATCGCA AGCTAAATTA
38801  AAAGTAACCA AGAAGCAAAT ATTTAAATTC CATGTATAGG AGCAAGTAAT
38851  CCTGACAAGT AAACTCAGTA AACCTAACAA GAATTAGGTG ATCCTGGTAG
38901  GAAGGGAGTT TGAGGGAATG TTACTAGTAA TAATATTCTT AAAGATTCCT
38951  AATCAGGCAA AAGCAAAAAA TCAAAATGAA GTTCTCACAG AAAAAAAAAA
39001  TTGATAGAGC TTTATGCAGC ATGAGTAAAT CCCTCATTCC TCGGGGGAAA
39051  TATCAAATAT GATGAGATGA TCATGGGAAA AGAACTTCAG CTTAGTTTTC
39101  AAGATATAAG AGAAAGAGGA TATTGATATG TTTAATGATA CAAAGACAGT
39151  TCCCAGGGGG AAAAATTAAT TTTAAGGCCT TGTAGTACAA AATAGATATT
39201  CACATAGACA GATATGATTA ATGGAAGGCA ATAAATAGGG GGAAAAAGAA
39251  AAGGTAATAG GGCAATTTAA AAGAAAAAAA AGAGAGGTAG ATATACAAAG
39301  AGACAAATTG ATGAGTGAAA AATGATTGAA GTAGAAATAA ATATATGGTC
39351  TATAAATAAC TAGGTCATGA AAGAAGACAC TTGAGGATGG TGATGCATTT
39401  AAACAACACA AAAGTGATAA TATGTAGACA GAAATGAAGG CTGAAAACAA
39451  TGGAGTTATT TCAGAGCTAT TTCCACAGCC AGAAAAAATA CAAATTCATA
39501  ATAAACATAA AAACATAATA CTAATAAAAC TTGATGTGTC AAATAAGACA
39551  AGAAAAATCA GGGGGGCAAC AATTCTTAAA ATCTCTAAGA AAAGGGCAAC
39601  ATTATTTGTA GTGGAAGATT TTTATTTAAC TTTAGCAAAT TTTAGGCAAG
39651  TTACAAAAAG TAAAAATAGC ACATGACTAA TGTAATTAAT ACATTAAGAT
39701  AATCAATGTA TTAACTGCAG TTAACATTTC ACAGAGAATG TACACCCATT
39751  TTGATTAGCA CATAGAATAT TTACCCAAAA TGACAGTATT TCAGCATCCA
39801  AAACAGGCTA TAAACTTAAG CAGCAGATTT TTATATGTGA AAAATACAAT
39851  AAATCAAAGC TCAAACCTTT TAAAATTACA AAAAAAAAAC CCCTCCTATG
39901  TCAACATTGT GCCAGGTCTA AATCCTACAC GTATTACCTA TTTATCATAT
39951  GTATTCTGTC TCCTTCAATA GAATATAAGC TGCATAGATT GTGGTCTTAC
40001  TTCACTACTA CACCCCCAGC ACCTAGGACA GTGCCTGGCA CATAGTGAGT
40051  ATTGTGGAAT AAATAGATGA TTGAATGTGT GATGTGTTGC TCATTTTATG
40101  ATGAATAAAT AAGAAAATAC TTTAATTAGG ATGTCAACAT TTTGCATGCA
40151  AATATGGCTT CTAAAATATA TATTAAATAT ATTAAATATT GATCTTGCTT
40201  ATACTGTGAA CTGTCTCAAA AACATTTTCT AAGTAATTTG CAAAGTGCAG
40251  ATTTTATCTC AGCTGTTATG CAAATTACGT ATTCTTAATT AGTGACATAT
40301  TGGGAGATTT TAATAAAGAA AAATTCATTA GTAAGCCTCA TTCTTTTAAG
40351  GAGAATGGTA TCTTGGGAGG TTTGTTGATA AAAAAGATGA ATACCTGAAC
40401  TACTTTGTTA AACACTCACT AAACAAGGTT CTCACTCATG GAGTTAGATC
40451  CACGCCCTTA TCAAACCATG ACAAAGATAT TGTAAGTGGT CTCTTAGTCA
40501  CCATTTTTCT TTCCTATATG TGCATTTTAC TTGCCTCCAG ACCAATATTA
40551  ACTAATGTAG ATCTCTGTTA AAGTCATTAT GCTACTCAGT AATCTTCATG
40601  GTTCCCCTTT TCCTACTAAA ATAAAATCCA ATGTCATAAA ACAGGTACAT
40651  GAGGCCTCCA TAGTCTAGTT TCAACCTGCT TTCCCTATGT TATTTTCTAA
40701  TATTTTTCTA CCCTGCTCTC CAATCCGATT ATTATGCTTA CTACCTCCTC
40751  TTACATTTTC CACCTTCTTA CCTTTCTTCA TAACATTCCT GACTCTGGAA
40801  GATTTGTTTA GAGTTCATAT CCAGGCTGGA GCAGTTATCT GATCAGCACA
40851  GAGAATGGTA GTATTACTGT TCCCTTTGAT CCAGGCTCTA AATTTTTATT
40901  AAAGGAACTT AAGGTTACTT TTTTATACCC ACATTGCTAT ATGGGCTTAC
40951  ATTGAGTTTA TATTCAACTA AATACTAACA GGTCTTATTT ATATGACCTT
41001  CTGTCAAGCT GAGTTCCACA CATTCTTAGT AAAGTTTGCA ACCCTGTACA
41051  TTTGGCCCCT TAAATCACTG CTTTCCTTTT TGAAAACAAA ATATCTCTTG
41101  ATTATACCAT CTCCTCTCCA TTTCTGCTAC TGCCTTAGCC CTTACCACCT
41151  TAAGCCCTTT ATGAGACTAG CAGAGAGAGA GTAAAAGAGG AAGCGAAAGA
41201  AAGAAGGAAG AAGCATTGTT CCTCACATGT GGACTTATGT TCAGTCCCCT
41251  CCTCCTTCCA AACTATGTCC TATATAACTA GCAAGGAAAA AAATCATTGT
41301  AAAATTAAAT CGAATGATCA TGACTCCCCC CAGACAAATT CCCCTCAATG
41351  CCTCCTTGTT GTCTTCACTG TAGCCTCAGA TCTGATGTAA TTCATTTCCT
41401  ATCCTCATCT CCCTCCTTAT TTTTCATCTC TTATCGTCAA ACAGCTCACA
41451  CTCTCTGTCT CTGGCCTTTG TATTTGTATT TCCTTGAGAT GACAACATCA
41501  TTTCCCAGCT TCTCTTCCTG GCTTACTGTA ATTCCTTCTT CAAGACTCAG
41551  CTCTGGCACT TCCTCCTCTA CGAAACTTTC CTTGGCACCC TATAGTAGAA
```

FIGURE 3, page 13 of 27

```
41601 TGTGCAGGTG CTCTTGCTCT CTGTTCCAGT GACACCAGAT TTACCTCTAT
41651 CATGATGCTC ATTATGCGGG TCTGAATTGC CTGCTCACTT TCTCTCTCCC
41701 CAGAATTAGA CTTTGAGCTT CTTGAGCTCC TTGAGACCAA TGAGTTTGTC
41751 TTTCATCCCT GTAACTCTAG AGTTGGAAGA GTGCCCAGGA GTTTGTCAGT
41801 TTATGGTGCC AGTAAAACTA TTCCTGATTT TTCTCCTTGT TTATCCAAGA
41851 AGAGTAAAGG GCAAGATAAA AAAGGAATGT GATGGAATTC AATTTAAGCA
41901 AAATCAGGAT TTCAGCCTTT TGATATTTTA ACTAATTTAG TGAGCATTTA
41951 TATTTTGCTA TGCATTGTCA TTCCATTAGT ACAGGTGACT ATAATTAAAG
42001 CTTTCATGAG ATTATTTTGA TTCACCCTTA TCGTAAGACT AAAAATGAAA
42051 CAGACACAAA TAATCTGTCA TAAATGGTGA TTCTCTGGGA CCCAATTTTT
42101 TGGAGCCAGT AGTGAAACAA GCATTGGATT TTCTGGGCTG GGAAAACTGG
42151 AGATATTCAG GTCCCTATTG ATTTGCCTTC TTTGGAAAAT GACTGGCTCA
42201 AAGACAACTG GGCCTTGTCC CTCTATCATG GCCATCTTAA ATGTTATTTA
42251 ATACCAATAA TCAGTAATAG GTTTTACTGG AATGACGGAG TTGTGTAATC
42301 TCTGGAAATT TTCTGAAGAT TTCTAGTGCC TATTTCTGAT ATGGTTTAAG
42351 CATATATCTG GTCAAAGCTA GTCTCTCAAG GGTCCATCCA GTTAAGAATC
42401 TATCATCATT AAGCCTCAAA CATTCTTAAA ATAATGAAGG GTTCCTCTTT
42451 CCACAACTTC CTCTTTACTT TCCTGATCAG TAAATTGACC AGAAGAAATT
42501 AACCTACTTA CTACTAACTG TTTATTTCTT ATATCAGCAA GTATGTATAT
42551 GTGTGTGTTT TAACAAATCT AAAAGTAGAT TTCTTATAAA CAAGTGTATC
42601 AGCTTTCCCT TATAGTACCT AGGTAATTAT CAATTGATTA ATCTGTATAT
42651 TTTAATGATT TGGCTCCTTC TCTAAAGAAG CAGAAAACTA CTTCAAAATC
42701 TAAGATAGCT GAGACTTCAT TACTTGTTGC AAAATAGAAT TTAAGTGGTA
42751 GAATCCCACT GGGGAGTACT AACATGAATA ATTACCATTA CAAACAATCT
42801 TCCAAAATGA ACAGTTTCAC TGCATTGATT GATAGTAGCA TCTTCAAATG
42851 TGATTTACAT TTATATCTCT AATGAAAATT AGTACGTACT TCACACTTTC
42901 TGATTTTTCT ATGTCCCTTC TGTGGCAACA TAATGTCTTA TTTCTTCTAT
42951 TTGTATTTGT AAATTATAGA GTAATATTTG TGACAGGCAA TGGGTGAATA
43001 TGTTTTGCTA AGAGCCTACA CTTACATCAT CTGATTTTTC AAAATACCTA
43051 CTGCATTCCA CTCTACATTT CAATTTAATT TCTTTTAATT TGAAATGTGT
43101 CTTGAGTAAC TGCCATGGAT TTATCATAAT GCAATACTTT GTGTTTCCCA
43151 CTTTTAAAAT TGTATTAAAA TTACTGGAAA AAGTAACCTG GAGACAGCCT
43201 TGACTGAAAA AAACTTGAAT GACATTAAGT CAGAGTTACC ATATCTGGAA
43251 TATTTGTTCC ATGTTAGATG TAGCATGTGC TTTACATAAA TTATTTCCAA
43301 CTCTTGTAAT GAAGGAAGTA TTTTCTCTAT TTTGCTGGTG ACAAAACTAA
43351 AGCATAGAGT TAAGTAAATT GTTCAAGGGC CATGTTAGCA GGTGGCTAGA
43401 CCAATATTCA AATGGGGGTG GATCTGATGC CAAAGCCTGG GCTTTTATTC
43451 TAACACAAGG CCACAAGCCA CATTAATCTT TATTATTGCC ATTAATATGC
43501 CACAAGCTTA TATGTTACCT CTTACTGTCT AATCTTCCCA GACTCAAAAA
43551 AGACATAGGC TAAGACCAAG CCATATTAGT CTAGTTTTTC TGTCTAGTCC
43601 ATATCAGAAC ATATACTGTA AGTGCCCTAG TTCACAGGGT TAGGAATCAC
43651 TATATTATTT AGTTGGTAAT TTTCCTTTTT GTGGCTTCTG GCATAAGCTC
43701 TCTCTAGAAC CAGGGCCAAT TGTTTCTCTC TAATGACTTG GAGGGAGGCT
43751 AGCCTGAGGC TATCCTTAAA AGTGCAAGTT GATTTATCAT CTTTTCCTTT
43801 GTTCCATGGA TGAGATCCAA CATGCAGCTT CAACTAGCCT CACGGGGACA
43851 GATATGTTAA CTGATTTCAT TCCACAAGAA GAAACATTGG TAACAAGATT
43901 TGGCTATTTT CTAATGTTAT GAATGCAGTG TTTAAGCAAT TATTAAAGTA
43951 TATGCATACT TTTTAATCTC ATTCCCTGTG CCAAATATCT AGATAGATCG
44001 ATAGATACAT AGATAAATAG AAGGTGTAGT TACAATTGAA CATAGTCAAC
44051 AATAGAAATA GGATATGTTA AAGATGCTGA AAACCTCCAT AGCTTGAAAA
44101 GTTGTGAGAA TATGCAATTA ACAGTTTACA ACAGAAAATG GTTAACACAT
44151 CTCTTAACTA GGAATTAAAA CATTTGGAGT AAGACTAAGA GTCAAGCACC
44201 TGGCTAGAAT ATTAGAACCT GAGAGTGAAA TCTCATTTGC TTAGTGCAAT
44251 AGGACTTTAC TCCTATAATA GAGAATGAGT CCAGCTTATT AACATTTGAA
44301 GAAATTATAG GCACTGTCTT TTTAAATAAA AATTCGAATT TATTTTTATT
44351 AAGACAAGGA AGCAAAGCTG AACACTGCTT CCTATCTTTG GCCTCACTGC
44401 TTTTCTTACT TTTTGCCTTT GCTCCTCTTT CCCAGGTTTC TAGCCAATAC
44451 CACTTTCAGA GGCCTCAGTG GTTCCATTAG AGTAAAAGGT TCCACCATCG
44501 TCAGCTCAGA AAACAACTTT TTCATCTGGA ATCTTCAACA TGACCCCATG
44551 GGAAAGCCAA TGTGGACCCG CTTGGGCAGC TGGCAGGGGA GAAAGATTGT
44601 CATGGACTAT GGAATATGGC CAGAGCAGGC CCAGAGACAC AAAACCCACT
44651 TCCAACATCC AAGTAAGCTA CACTTGAGAG TGGTTACCCT GATTGAGCAT
44701 CCTTTTGTCT TCACAAGGGA GGTAGATGAT GAAGGCTTGT GCCCTGCTGG
44751 CCAACTCTGT CTAGACCCCA TGACTAATGA CTCTTCCACA CTGGACAGCC
```

FIGURE 3, page 14 of 27

```
44801  TTTTTAGCAG CCTCCATAGC AGTAATGATA CAGTGCCCAT TAAATTCAAG
44851  AAGTGCTGCT ATGGATATTG CATTGATCTG CTGGAAAAGA TAGCAGAAGA
44901  CATGAACTTT GACTTCGACC TCTATATTGT AGGGGATGGA AAGTATGGAG
44951  CCTGGAAAAA TGGGCACTGG ACTGGGCTAG TGGGTGATCT CCTGAGAGGG
45001  ACTGCCCACA TGGCAGTCAC TTCCTTTAGC ATCAATACTG CACGGAGCCA
45051  GGTGATAGAT TTCACCAGCC CTTTCTTCTC CACCAGCTTG GGCATCTTAG
45101  TGAGGACCCG AGATACAGCA GCTCCCATTG GAGCCTTCAT GTGGCCACTC
45151  CACTGGACAA TGTGGCTGGG GATTTTTGTG GCTCTGCACA TCACTGCCGT
45201  CTTCCTCACT CTGTATGAAT GGAAGAGTCC ATTTGGTTTG ACTCCCAAGG
45251  GGCGAAATAG AAGTAAAGTC TTCTCCTTTT CTTCAGCCTT GAACATCTGT
45301  TATGCCCTCT TGTTTGGCAG AACAGTGGCC ATCAAACCTC CAAAATGTTG
45351  GACTGGAAGG TTTCTAATGA ACCTTTGGGC CATTTTCTGT ATGTTTTGCC
45401  TTTCCACATA CACGGCAAAC TTGGCTGCTG TCATGGTAGG TGAGAAGATC
45451  TATGAAGAGC TTTCTGGAAT ACATGACCCC AAGGTAATAC TTCATTTTAC
45501  TTTAGCTTTC TTGATTGTCC ATTATAATTC CATATGTTGT ATCTTCTGCT
45551  GTAGTATGCT CATGTTCTTC CATCTAACAC AGGAATATTC TCTCAGCCAA
45601  GTATAGAGAC TAGTCCAAAA GTCTGTTGCC TGGTTTAACT AAATATTTCA
45651  TTGTTTGTTT CATAAATGAA ACAAAAAGAC TGAGAAGTTT TGGGGAGTGT
45701  CTTTTCTAGA GTAGGTCTTT CTGATAGAAA TATCTATTAA TGCATCTTTT
45751  CCTTGTATTA TTTGACCATC TGATAGCACA CCTATCAGGG AATGGTCTTA
45801  TAAGGTATTT TCACCCAAAG CACACCTTAA AAACTGATGA ATTACTTATC
45851  TTGGGAATTA ATAAAAATAA ATTGGAAGAT CCATATTTTA AATAGCAAAG
45901  AATCTTTTTC ATCACTAAAA AGTGATACAA TGGAAAGAAT TAAATTTTAT
45951  TATAAGCACC AAAGTCAACT GCTAGGGAAC TCACTGAGTG TAGAACAAGG
46001  AGTATCAGAC TAACTGAGAT GGCAGAATTA GCTAAGGCCT ATAAAGTAAG
46051  GGGAGCTGCT CAGCTGACTA CCTTGCATAG AAGGGAGAGT GCCAGCAGTC
46101  CAAGGACATT CAAGAAGATT TTGTCTATCC AGGGTACCCT TGATATCCTA
46151  GACATCTGAC CCTAAGGGAA GAAGGAAGAG GAAGTGTAGA GTGCAGGTAA
46201  ACAGCCAAAG CAGGTAATAC TTAGGTAAGG ACAGCCATTC CATGTTCTCT
46251  CTGGATTGAA CCAGGGCCCC TCTAAGTGAG CTGGGGTACA GAAAATTAGT
46301  CCAGCCCAAT AGGACTAGAG AGAGGGGACT GTCAAGGACC AAGGCAATTA
46351  GAACAGAGCT CAGGGGAGTA CTGCAGTCCT GATGGGAAAC AGAGTGCAGA
46401  TCTGAAGCTG CAGTGCATTC CAACATGTAG GATACATTAA GTAGAGATTG
46451  GAGAAAGGTT CAATTCAGCA GGCACACTCA GGACATACCA TGTCTAAAGC
46501  AACTTAAGCT AAGCTGAGCC TTTCATATTA TAAAACATTC ACAGGCTTTT
46551  CCAAATGCCC CTTGTCACAC CAAGTCTCAA TGTATTGATC TATTTACTAT
46601  AAGTTACTAT TAAACATTTA AAATTAATTT CATAGACCAT CAACAAGTAG
46651  GACATTTGTA GCTATCTTTA CTAAATGATA GAATGCCCCA GAGGGCTGGT
46701  GGCAGCTTTA AAGATTTTTC ATAGATGGTT TCAATTGGAT GTAAGTTCTG
46751  TTTTGCAACC AAAAGAATGT AAGAAATTTG ACCCATATAT TGCAAACCTT
46801  CTGATAAGTG ACATGAACCT CATGAGAGGA TTCAGCCAAC AATGCCTCAT
46851  TGACTAGGCA AGAAATTTTG TAACTTCTCA ATGAATACTC AGGGCTTTAT
46901  GTTAGGAGCT GGAATTCAGT GAACACAAAT AAAATCATTA GCATAAATAA
46951  ACGCATCACC CTAAAGGGAG ATGTTGGTGA TGCTTCTGCA TTCACATTCT
47001  GCACTGGCAT CAGCAGCCTT TGTTTATTCT TTGCCCCAGG AGTCCTGTAA
47051  ATCTTCTGAA GGTTTTCAGC CTCACTAGAA ACTTAGATTA TTTGTGAGAA
47101  TCTCAACAAA GTGACTCCTA AATTATTAGC TCAAAATTAA AAGTATTTAG
47151  TCTGATCTAG TAAAAAAAAA AATCTAATAT ATGCCTGTTG TGGAGATTTC
47201  AGGCCATTAT CTTATGTAAA AAGATGAACA CAATACTAAC TAGAGCTTTA
47251  TTTATCAGAA CGAGTGATTG CCAAAATTAA GCCAGGGATG CTATGCATGA
47301  AAAAGCTCTA AGAGTGATTA TGCTAAAGTA TTAAAAATAA AATTATAAAG
47351  ACAAGCTATA CGCAGCAGTG AAATTATTTT TAAGCAAAAA GAAATAATCA
47401  TTTCATCTCT GACTCTACCA GAATAAAGAG TGAAATTTTT TAATAAGTCT
47451  AACCCAGTCC ACAACACAAA GCCAGCAGAA CTGGACAAAG TCAACTTTGC
47501  ATTACAACTA GTGAGTTCTT AATGAAATGG GACAAACCTA AATCTAAACT
47551  ATTTTCAATT TGAGATAATA AATGAATTTC CACTAAGTTT CCTAAAAATG
47601  TGCATGTGTG TACTAGCGTT GTTTCTACGG TAAAATATCT CTTTTGTAGG
47651  TTCACTTCTT TCCATAAAAA GACACCCAGA TTACTTAGCT AAGCAATGCT
47701  TGACCCCGGG ATTTAGGAGG AATAATTGTT GTGATAGAAT TTTTTAGTTT
47751  TCATCCAAAT ATGTCATATT ATGTGGACTA CATAATGTCC TCACTCTCAA
47801  ACAGAGATAC AAGATAAAAA TTATTTCCAC ATCCCTCAGT CACTCAGAAT
47851  GTACTCTTAT TATACCGTAG TTACTCACAT GAGTGTTTTC TCTCCTGTTA
47901  ATGCTAAATT CCTTGAGGAG GGCCTATACC ATTTCTTATA CTAAATAAGG
47951  TAGAGCAATT CAGAGGTAAA TGAGTCAAAT TGTTTGACTT CAATCAATTA
```

FIGURE 3, page 15 of 27

```
48001  GGGAAGAAAA GACATAAACA AAAGGAGAAG CAACTTAGAA GGTTACAAAT
48051  ACGCCAAAGT TTAGCAACAG ATGAAGTACT GTCCAAGTTC AAGGAAAGAA
48101  TGATCACCTT CAACTCATTA CAATGGAAGA AAGTTTAATT AATAAGGTAA
48151  TATTTGTGCC TATTCTTAAA GAATAGTAAG AATTCAGAAT GTGTGTCCAG
48201  GGAGGAGAAA TGGACATCCT AGGAAAAGGG AACCACAATG GAATTGCTTG
48251  GGAGGTAATA CTTTATATTA CCTATAGAGA ATACCGATTT TGCTTTATCA
48301  CGAACTTCCT ACTTGCTTTC ACTTGCGACC ATGCTTGTGA GCTGCATGCT
48351  AATTCTCTGG GTTGTTCTGG GCTGATCTGC CTCTTTTTTT TCTGTAACCC
48401  CTGCAGAAGG TAGGCCTTTG ATTCCTAGTC TCCTGAGAAA ATAGAATTCA
48451  AGTATAAAGT GGCTTTGTGG AACTGCTGAT TTTGAGTCCC TGCCTCTTCA
48501  TTTTCACCTC GTCTCTCCCA AACCTTTCCC CAACTCCTGG GCCCCTTTTC
48551  AGGGGCTTCC TTAAACAGAA TTTTTCTCCC TATCCCTTTT CCCTGGGAAC
48601  GATTCTCCCT AGGCTTTAAA AACAGTTGGG CTCCTCTGCG GAATTTACTA
48651  GTTGAACTTT TTTGGACTCT GCTCCTGTTT CAAATTTGGG GGTTTACCTA
48701  ATGTCAAACA ATTAAAATGC CCGTTGCTTA AGCTGGGGCC TTCTTTTGCA
48751  ACTACCCGGA GGGAACCAAC CCCTGTTTTT TTAAGTGGCC TAGGGGAAAC
48801  CTGGCCTTGG GGGACCCCTG GCCTTGGGGG GNNNNNNNNN NNNNNNNNNN
48851  NNNNNNNNNN NNNNNNNNNN NNNNNNNNNN NAACTGGCCA AAGCCTTGGA
48901  AGGCCAGGGG GAAGAGCAGG ACGACAAGGG TTAGGAAAAG GAAGGCAGGA
48951  GCCAAACATG TTGAACCCTT AGAGGCCATG TGAGGAGTTT GGACTTCATC
49001  CCCAAGGGCC CATGGGGGGA GCCATTGATG GGCATTAAGC AAGTGAGGGA
49051  CATGATCAGA TCTGAATTCT AAAATTTCTC TGAGTGGATC AGAAAGGAAG
49101  AAAGGGAATA TGTGGATGAC AGAAATGATG GTGACTCAAA TAAGAGCAGT
49151  GGCAGTGTTT GCAAAACATC TCCATGTTAG AGTGAGGTCC CTGTCAGGCT
49201  AATAAGATGC TTTCTCTCCT GGAGTCTGCT TATTTGCTAA TCCTTGAAGG
49251  AACTTTCAAT TCTCAGAACC TCAGAACCTT TGCCTTCACA GAGCCAATAA
49301  GACAGATATG GGAGCTGATG AGCAAATACA ACAGAAAGTC ATGCAAAGGA
49351  AAAACACAAA GAGACAGTCC TCCAGCAGAA TTCTGAGCCT GGGTCTGCTG
49401  GTTCCCTGAT TCCTTCCATG CTTTGGAAAG GAACGATGTG CTGGTGCATT
49451  CAGAAAAGAA AATGAGACCC AGAAAAGCAG GATTTCCCTA AAAATCCTGG
49501  TCATAGACCA TAAAAGTATT ATCACAACAT AATGTAAAGA ATGTATTTCT
49551  GGAAGGAATT CTGTTTCTAT ATGAGAGAAA GGTATTTTAA TTAATGATTC
49601  TACAGCCCTT TTACCTTAAA GAGAGGGTTT GTTTAGAAAG CTTGAGTTGT
49651  AAGCTATACT GTTAGCTTAG TTTGTGCTAA GTGAGATGAC AAAGCTGTCA
49701  CCTTCCTCTA AGTTCAAAGA ACAGTTATCA ATTAATTACT CATCAAGTAT
49751  TTTCTTGAGC AACTACAAAA TGAAAGGCAT TAGAAATACA AGGATAAATT
49801  AAAATTAACA TTATTCTTGT TTACATGGAG CTTCCAGTTA GTGAAGAAAC
49851  TGAGAGTCTA GACGCTAATC ACATGATTAC ATAATTAAAT TTAAAACTGC
49901  AACTGTGATA GATTCTACAA AAGATAGGTA TATGTACTGT AAGGGCTTAC
49951  GAAAAAGAAT CTGGCCTACA CAATAAGTTA GGGAAGTAAT TACTGAACTG
50001  AGAGCAGAAG AATGCATATA AGTTAAATGG ATAAAGCAGG ATAGAAAAAT
50051  AGACTAGATA AAATGAATTA ACTTGACAAA CAGATATAGA CTACCTGCAA
50101  GGTGCCAAAG GTCGTGATAG GTAACTGTAT TACACAAACA AATGAAAGTT
50151  GGTCTGCAAG TTACAGAAAA TAGGATGGGC TGAAGCTTGT TAATTCCTAG
50201  TTGTGAGAAG TTGGTGTTAC TTTAACTATC CAAGCCTCAG TGTTTTAATC
50251  TGCAAAATAA GAAAATAACA TCTATCTTGT AAGATTATTG TGAAAATTTT
50301  AAAAGCCCTT AGCTTACCGT CTGGCATACA AGTAGCAAAT CCAGACAGAG
50351  GGAGTCAGTA TGATATAGTA TCAGAAGCAA TGTTACACAG TTGTCAAAAG
50401  CTGAATGTCT TTGATCAGGC TGAATTCCAA TCCCAGGTAC AATTACTAGC
50451  TCTGTGACCT TGGACAAATG ACACACTTTC TAATCTTCAG TTTCTTTATG
50501  TAAAAAGATG ATAGACATAT CTACCTCACA TTTCTTGGTA GGATCAAAGG
50551  AGATAATGCA CGGAAAGGTC AAAGATTACT TAAATAAATA TTTGCCTACA
50601  TATTTTATAT GTACAAGCTA CTATATCAGC ACAGATAAAT AAGTAGTTAT
50651  GTTTCTCTAT TGTTGTTGTT TTGGGTAGGA GGGTGAAGCT AGACAAGACC
50701  AAAGGCTTCA CATAGAAAAT TTTCACCTAG GTCTTTGCCT ACATATTTTA
50751  TATGTACAAG ATACTATATC AGCACAGATA AATAAGTAGT TTTTTCATTG
50801  TTGTTGTTCT GGGTAGGAGG GTGAAGCTAC ACAAGACAAA AGACTTTACA
50851  TAGAAAAATT TGACCTAGGT CTTGAAAAAT TAATAGATGT TGGACAGACA
50901  ATGCTGATAA ATGTGCCTTG CGCAAGCCAT ACGACTGCAA TTTGCTACTA
50951  TGAGAACAGC CCCGGGGGTT CAAGGCATAA GGATAATATT TTTAAAAGCC
51001  TGGTGAGTTC CTCCTAATAA ACATCATCGC TTCAGTTGTT GTCATGAGCT
51051  AGAATGCAAG ATGATGTAGT AGATAATAGC ACATGCTTTG AAATAAGATA
51101  GACATGGGTT CTGAGCCAGT CCCTACTACT TACAACTGCA TGACCTTATG
51151  CCCATTACTT CACTTCTCTG AGCTTCAGTT TACTCATCCC TAAGAGGAAG
```

FIGURE 3, page 16 of 27

```
51201 TAACAACAGT GCCCTCTTCA CGAAGCTATT ATGAGGATTC AGCACGATAA
51251 TGTATGTAAA GCTCTAAGTA TCTTGTTTGG CGCATAATAA GTGTTTAATA
51301 AATGTTAAGT ATTGTTATTA TTGTTGATGT GGCATTAAGG TTATGCTGGC
51351 ATAAAACATT AGAATTTGTT CAGTGCATGG AACAATTACA TTAAACTTAG
51401 AGCAAGCTAT ATTACTTACT TAACAGTGGA ATACCAAAGA AATACAATGA
51451 ACAACAGGTT TTAAGAGTTC CTATATGGCA GTGGTTGCAG GTATTTATCT
51501 TTGTCACCCT AGTAACTTTG AGAACTCTAC AGAGTAGGCC TTCAATAAGT
51551 GTTGAATAAA TGAACGATTT TGCTGATTTT AAAATATTTT TTATACTTGT
51601 AAACATGGTA AGTGTTTCTG CAGATAATCT GTAAATAAAA AATACATCTG
51651 TAAATTCAAC ACCAATGTGT TTTCTTCCAA GGTGTGTGTG CATGTGCGTA
51701 TGTGTGTGTG TGTATAATAT ATATGGGAAA TCATGGCATT TAAATAAATG
51751 TATACATGTT TTGTTTTGAT CATACCATAT GAAAGCTTTT TTCCACTTGC
51801 CATATGAGCA TTTGCCTTGT TTTATGAAAC ATACTTTACA AACATGATTT
51851 ATATGTTGCA TTACACTCTA TAAGAATATA CCATATAATT TATTTAACTA
51901 TTACCTTATT GTTACACCTT TACTGTGTGT CAAAACTAAT TCATCTTCAA
51951 ATATATGTTA TTTGTCACCA TATTCAGTGA GTTCTTAATC ATTTTTAGGG
52001 TAAACAACTT AAAAACCTAA TTATTAAAAA AAATACTCTG TATTATCTCC
52051 CTCCTAGATG AGAACATTTT ATGAAAACAC TAAAAATAAA TTCAATAAAC
52101 AAAATGTAAT ATAGCCTAAA GGTGGCTAAA CACAAAAGTG ATGTAGTCAC
52151 AGCATTAGCG CAGGTTTATT GTAATCTCAG GATGTAAGGT TTTAACTTGG
52201 CCTTTATGTT ATTCTAACCA AGGAGTATCA TAATCTTTAT TATGAATGTA
52251 CACTTTGTCT AATATGCAGT TTACAATAAT GAGACTAATT CTACATGCCA
52301 ATTTGCATGG CTTCTAAAGA ATTCTAATAG GTTCCAATAT AAAGCAAAAA
52351 AAATTGTTTT GTATTTTTTG TTTGTCGTTT CCATCTGTTT GCTTCTAAAG
52401 ATAGAGCAAT TTCTGATGTA AAAAGCATGT AGCCATGTCT GCACATTTCT
52451 ATGTACATGT TTCTGCCTGT GGGGGTTAGA AAAGTTCCGA ATTATTATTA
52501 AGTTTCAAAG AATTATGAAA AAAATGTTAA AAAACACTTC TAAGAATAAT
52551 TTTTATTTAA GCCATTTCTT TTTCTCCCCC ATAGTTACAT CATCCTTCCC
52601 AAGGATTCCG CTTTGGAACT GTCCGAGAAA GCAGTGCTGA AGATTATGTG
52651 AGACAAAGTT TCCCAGAGAT GCATGAATAT ATGAGAAGGT ACAATGTTCC
52701 AGCCACCCCT GATGGAGTGG AGTATCTGAA GTGAGTGTCA ACCTCTTGGA
52751 TCCAAAGAAA AATTCTCACT GAAGAGAAGT AATTTAGCTA CTGACGCAGT
52801 ATATGTTAGT TTCTGAAAAT GACAGATGAA TATACCCACG TTGTGTTAAG
52851 TAATACTTTA CACTGTGTGA GATCCCAGGA GATGGTGTGA AATAGTGTGT
52901 ATTTAATTAT GTGACCTAGA TTACTTGTGA CCTGCATAGT CTCAAGTTGG
52951 TAGTAGCTTT GTTCAAAGAG TCAGTGGGGC CATTAGCATA GCAGATGGTG
53001 GAGGAAGTAA ATGTTGGCTT TACATCACTT GAGAATACAA TGGTGCTGAA
53051 ATAGTCAAAC ACACAGGGAA TATGGCCAGA GGATAAAGTG TCCCAAGGCA
53101 ACGTTTTCCT TCCCAGTGAA TATATCTCTA AACCCATGGA ATGCCTCCTC
53151 TTGCCATGAG GAAATGGAGT TTATCTTAGA GATTTCCTGT AGAAAGGAAA
53201 TAAGATAGAA GACAATGATT CCCATGCCTG CATTCTTCTC ATCAGAATTT
53251 ATGAGAAGCA ATCATGAGAA ATCACACTGC CATGGCAGAT TATCAGAGCC
53301 TGTAATTCAA TGAAGTTGAA TACAAAGGCA GACAGTGCAG TGATGGGTCT
53351 GTTCTGTCTA GTCTTCCTGA GAAAAGGGAA AGAATGGTTC CTGAAAAACA
53401 GGAAGACATG AGGGTGAGTA GTCCTCTCCC TCCTGCTCGA TGGAATCAAG
53451 ATAATAACAG ACATCCACAC CTCCAATTCC TAGAATTGTG CAGCATCAGG
53501 AAACTGGTTT CTCCATGGTC AGCATCAATA ATCTCCCCAA TGGACAGCAG
53551 GATCTGCCAC CTCAAATTCT TTTTTAAGAA AGAATAGAAA TAAATAAATA
53601 ATTTCATGGA ACATAAGGGT TTTGTCTTTC TCAACAACTT TAGAAACATG
53651 CCACTTAAAA AATTTTATGG ACTTTTAACT ATAGCTTAGA GAAAAAGCCT
53701 TGTTCTCTCA TATTTGCAAA ATTATACATG ATGTGTAAGT ATTATGAAAT
53751 GCCACTTTTA ATTTTGCAAG AACATCAACA CATTACAGTC TCTCTCTGAC
53801 ATGAAGTTTA GAGTCCCTTT ACCTCCCAGA TCTTCTTGTG TATTCTCTTC
53851 TTCAGGCGAA TTTATGGTTG AGAGAAAGAA TAAGATGTCA GGGTAGCAAT
53901 GGCTTCCAGC TCAATAGAAA TAGCAGACAA ACTAGGCTCT GCTGACAGTG
53951 TGAAAAAGGA TGAGATGAGC TACTGCTGCA GTCCCCAGCA GTTCCACTCC
54001 ACTCAGGGCA TTCACGTATC TCAGGAGCTT TACCTGAGAA GGCCCACGTG
54051 CCCAGCACTG GCCCTGCCCT AGCCTGAAGG GAAGCAATCT TCAGGAAAGC
54101 GGCCACAGAT GAAGGCCCAA GACAAGTCAA TTTTCCTTGG TAATAAACTA
54151 GCAAGTGGCA GAGTCAGGAC TAGGACCAGG TCTCTGGAAT CCAACTGCTG
54201 CTTCAGACTA GTCTGGGAAC GATGATGAAA GAGTAGGTCC TTGATGTTTG
54251 CAGAATAGTC CATGTTCCAG CAACATCTAT GTTGCAGTTA GTATCTGAAA
54301 GCTAGTTAGA AATGCAGCAA CTCCAGCCTC ATCCCAAACT TACTGCATCA
54351 GAATCTTCAT TTTAACAAGC TCCCCAGGCA ATTCACTGAT TGAGGTGAAA
```

```
54401  TTGGCATCTA GGCAGAGCTT ATCATTAATG CCCTCTCACC ACTTCTCTCT
54451  GGGCCTTAAC TCTCCACTTT CAGCCTAGTC ATTTCCTGTG CCCTCAGCCA
54501  CCACTTCCCG CAACCACAGT CTTCATGTTA CCTCCCTGGC ATCCCAGAGC
54551  TCTGACCTAC AAGGCACAAC CCCTAGCATT GCCTGTGCAA GGAACTTTTC
54601  TACATATTGA ACCTGTCCTT TCCCTCTCCC ATCAAAATTC TCCTGGACTT
54651  AATTCTGCTC TCTCAGGGCC CTGCTTTCTC ATTAACAGTT TTCCAAAAAA
54701  TTAACTCCTA CTAAAATGCT TATTCCTTTT ATTATGTTAA TATGTGACTG
54751  GTTTTCTTGT GATGTGTGAT ATGTATTTTT AAATAATGCT TAAGAAAAGA
54801  CAGGGCATGA TTCTATAATA GAAATAACCA TTGGGGGCCC TGTGAACCAC
54851  AACAGTGATT CAGCCAATCT AGAAGCTACT TGTAACTGGA TCCCACTTGG
54901  CCATTTCCTC ACCAGTGACT CAGGGTCCCA ATGGAGTCTG AGAGCTGACT
54951  GCTTTTCGCC TTTTCACGTA ACTGAAATTT ATCATAGCTA TCTGCACTTT
55001  GCAGTCTAAA ATCAAGAGTA GTTATTTAAG GAAGGATCCC AGAGACATTA
55051  GGCTTCATGA ATTACTGGTT TTAAAAAACT GAAATGAACC TCATCTTTTT
55101  TATTGTCATA TTGCTACCAC AAATATTTGT GGAATATTGG CAAGTGATAA
55151  CTTGTTGCTA CGTAGCTGTC AAGGTACATT ATGGTACTGT GGCAGTCGAA
55201  CTTTGATTGG AGAAACAGCT TTCAGCTCAA TTTTTATTTT ATTGCCAGGA
55251  TTCCATTAAG ATTCCTTATC AACTTCTAGG AGACAATCCA CATCCCCAAC
55301  ACTTTCTAAA GCTTCCCATT ACTGTAGAGC TGGGAGATGC TTCATTTTGG
55351  TTAAAGTTAA ATTTGGGCCT CATTGTAACT TAAATCTGAT ACCCCTTTGA
55401  AAAGGGGATG CATTTTAAAT TGGTTATTTC ACTTATTTGA AGAGTAGGAT
55451  AAGAAAGCAA CGGTCATTGG TACCAAAAAG GGAAGCTGAC CTGCCAACTA
55501  TGTGTCTATA CATGACCCAG ACAAAGCCAT TCGTGTAAGG ATGTGTTTCC
55551  TGCCCTGATG AATCTTCTGG GTGTCTAGGG ATATCTTTCT CTTTTTGATT
55601  TTCTATGAAT TCTAGTCATA TTCTCCTCTG TTTAGAAGCC ACACTGTGTT
55651  AAATTAGAAC AGCCTCACCA CTGGATCTAA GAGAGGAAGG ACTGAGCCCA
55701  GAAGGGATAG AAAAGAGTTA TTCTTTTTGC AAAGCTGTTT GGACAACTCT
55751  AAGGGTAGAA AATCCTTTCT TTTTTTTCAA ATTAATAAAT ATTTTTATTT
55801  TTAAAAAATA AATACCTACA CCTACACAAT AAAAAGGAAC TGAGGTAGTC
55851  ATCGCATGAG ATAGAAAGAA GTGTAATACA GAGTTCTGGT TCCCAAGAAA
55901  CTTACACTTT AACTGGGGAG ATAATATAGT GCACAAAATG GTTGCTTTTC
55951  TGATCTTCAC AGAATCCATT CCCTCTTTTT GGTCACAGCA TCCTGCATTT
56001  CTTCATCCCT CTTCTACTCT CACTGATTTA TATGAGGTGA ACCCCACCCC
56051  TGGCTCCAGG TGACACCACC TAGCCAATAA GAATGATAGT CCAGACTTTT
56101  TAATGATTGC CATTCTAACT GCTGTGAGAT GGTATCTCAT TGTGGTTTTG
56151  ATTTGCATTA CTAGTCCAAC CATTGTGGAA GTCAGTGTGG CCATTCCTCA
56201  GGGATCTAGA ACTAGAAATA CCATTTGACC CAGCCATCCC ATTACTGGGT
56251  ATATACCCAA AGAACTATAA ATCATGCTGC TATAAAGACA CATGCACATG
56301  TATGTTTATT GTGGCACTAT TCACAATAGC AAAGACTTGG AACCAACCCA
56351  AATGTCCAAC AACGATAGAC TGGATTAAGA AAATGTGGCA CATATACACC
56401  ATGGAATACT ATGCAGCCAT AAAAAATGAT GAGTTCATGT CCTCTGTAGG
56451  GACATGGATG AAATTGGAAA TCATCATTCT CAGTAAACTA TCGCAAGGAC
56501  AAAAAACCAA ACACCACATC TTCTCACTCA TAGGTGGGAA CTGAACAATG
56551  AGAACACATG GACACAGGAA GGGGAACATC ACACTCTGGG GACTGTTGTG
56601  GGGTGGGGGG AGGGGGGAAG GATAGCATTA GGAGATATAC CTAATGCTAA
56651  ATGACGAGTT AATGGGTGCA GCACACCAGC ATGGCACATG TATACATATG
56701  TAACTAACCT GCACATTGTG CACATGTACC CTAAAACTTA AAGTATAATA
56751  ATAATAAAAT AAAAAAATAA AAAAAATTTT TAAAAAAGGA ATGATAGTCC
56801  ATTTCCATGG TAACAATATC CAGGGATGGG CTCAGGACAT AGTCACAATA
56851  AAAGCAAATT AGACTAAGAG CTTTTCTGAA ACTGTTCCTC ATAGAAAATC
56901  CTTTCTTAAA TGGATGTATG TCTTTCACCT TTCCAAAAAG AATTGGGAAG
56951  TGGCTGAAAA CAAAGAAATC GTTGCATGTA TTTTAGACAG TTATTTCCTT
57001  TTAAAACTTC TCCTTCCTTG CCCTCTTTGT AGGTGGAAGC TCAGCCTATG
57051  CTGAGACTCA CCCTTCATCT GAACCTAGTC CCAACACTTA CTAGCTGTGT
57101  AACCTGGTTT AAGTTACTTC AATCCTCTGA GCCTCAATTT CCTCATCTGT
57151  TATATCACAG TCATTTCTGA GTGATAAAAG GTATAGAGAA CAATGAATGC
57201  AATGCCTAAC AACAAGAAGT CCCTCTAACA GTGTAATAAG AATAAACGTT
57251  CTCTATGCGC TTCCTATTCA ATTCAGAGTG GCTCTGGCTT TACTGATGGA
57301  TTTAGAAGTA ATTAAAGGAG CTGGTAGATA AACTCATTGG AAAGATGTCA
57351  TGCTGTCTTA TAAGAGTGCC TGTCTCCCCT GGTCTGTAGT CTAGACATCA
57401  GTGAGAAGCC AAGACAGCTA AGTCAGCACC TAGGTAGCTT GTGCGGCCCT
57451  TAGTGTTCGG GTTCTGTCCC CTAAACAAAA GCCGGCTGTC AGCCTTCATG
57501  CTTCCTTCCC ATTAATGAAT CATTTTCACT TTTCTCCTCT GGTCTTAAAT
57551  ATAGGAATGA TCCAGAGAAA CTAGACGCCT TCATCATGGA CAAAGCCCTT
```

FIGURE 3, page 18 of 27

```
57601  CTGGATTATG AAGTGTCAAT AGATGCTGAC TGCAAACTTC TCACTGTGGG
57651  GAAGCCATTT GCCATAGAAG GTATTAATCA GTCACTCTTG ATTCACTTTT
57701  ACTCAGGATG TGCTCAGTTT GCCAACCTAG AAAGTCACAA ATGCCAAAGT
57751  CAGAAGCAAA GAGCTATTCA TCTTCCCTCG TTTTCATTTT CAACTCATAA
57801  GCACTTAGCT ATTAAGTTGC TGAAGTTAGG AATTTATTTT TCACCTATTC
57851  AACAAATATT TACTTATCCA ATTTTTAGGG GGAAAAATCA TTGTTACCCA
57901  TATGATGTTG TTTCAGATAT CTGGGAGTGG TGGCACAGTG TAATAAATTT
57951  TAATTTAATC TGTATTGTGT GTGTGTGTGT GTGTGTGTGT GTGTGTGTGT
58001  GTGTGTTTAG TGGCAGGGTG TTGCTATGTG CTATGTTGCC CAAGCTTGTC
58051  TCCAACTCCT GGCCTCAAGT GATCCTCCTG CCTCAGCCTT CCAAAATTCA
58101  GGGAAATCTG TATTTTCTAA CAGCCAAATA CTCTAGCAAA TCTGACAGAA
58151  AAACTAGGAT GATTACATTT TACAACTGGG AGGGCCCCAA TATTGATCTA
58201  ATGCAATCTA CTCNNNNNNN NNNNNNNNNN NNNNNNNNNN NNNNNNNNNN
58251  NNNNNNNNNN NNNTGCCTGC CTTTTCATTC ATGGCATATT ACTAAGGATC
58301  ATCCATATTG TTGCCTCTAG TTCTAGTTCA TATAGTTTTG ATTATGTAAT
58351  ATTCCATCTG TGCAAATAGT CCACAGTTTC ATTACTCATT CTCTTGTCAA
58401  AGAACATTTG GGTTGTTTCC AATTTTTGCT ATTATGAACA GTTCCTCTAA
58451  GAACATTTTT GTACGTATCT CCTGATATGC TTGTGGCGGA GATCTTTGGG
58501  AATGGACTCA GGAACAGAAT TGCTGGTCTT AAAATATGTC AATATTCAAC
58551  CATATAAAAT AATACCAAAC TGCTTTCCAA AATGTTTGTA TCAATTTTCA
58601  GTTTATATTA CAGCAAGCAA TATATAAATA ATCTTATTGA TCCTCATCTT
58651  CTTTAACACT TAGTATTACT TCTTATTTAT TTATTTTTGG ACAATTTAAG
58701  TTGATTTTTA TAAGTTCCTG TTTATATTTT AGTTCTCATA CTGTATTGTT
58751  TATTCACATG GTTTTATTAT ATTATTCAAA AATTAAAAAT AAATTTAAAA
58801  AGTAAGAGAG GGTCATGCAT TAACACCGAT AAGAGAATGT CATCAACCAC
58851  AGACTAAGAT TAATCTGATT TTGTATATTT AAGGTTCAGA AGAGGGGTTC
58901  TGGAAGAGGT AGATAGGAAA TCCTAGCCCT GATAAAGACC TCAAAGATTG
58951  CCTCTAAGGA ATGTCTTAAT GGGAAAGGCA GAAGATCTTA AAATTTTTCA
59001  CTAATGCACT GTGCACAGCC CATTCCTCTC CTTTTCCAAC TCAATTCATC
59051  TACTCAGAGA TGCAGCTGAT TTAAGGGTAA TCATGACTAG GAATGTCTTT
59101  GAGTGCTTTG AAAGAAAGTT GATGAAAACT CATCACGCCC TTTTTTTGGT
59151  CTGATGGCAG TATCACACAA ATATGTACTG TGGTGGCAAT CTCTCAGGAA
59201  GGGTGTAAAA AACTCATCTG AGATTGTATT TTCTTCTAGG ATACGGCATT
59251  GGCCTCCCAC CCAACTCTCC ATTGACCGCC AACATATCCG AGCTAATCAG
59301  TCAATACAAG TCACATGGGT TTATGGATAT GCTCCATGAC AAGTGGTACA
59351  GGGTGGTTCC CTGTGGCAAG AGAAGTTTTG CTGTCACGGA GGTATGGAAA
59401  GACTGTTGAA AATGGTGACA CGTTGTATAG CTGTACCTCA GAGAACATAA
59451  GGAAATGCTA TTACTTGTGC CTCATCATCT AGGTTATTGC ATTTACTAGA
59501  CTCTTGCATA ATATTTGGAT TATTTTTTAC TTTGTCCAAA AAGCGTCCAT
59551  TCCTATAGGA ATTTACAGGG ATGTGGGTTT GTCTTAGATT TAAATGTGAT
59601  GCTATTTTGA TGAGTAAATA TCTAAATTTC TACTTTTCCC CATAACCTCT
59651  ATCCACAAGT GCAGAAGAAA TGCTGTTCTG AATTACAGCA ATAGTATCTG
59701  AGATTGACAT GAACAGTGTT TGATTTAATC GTTAATTGAT GGACATGATG
59751  TGTACTTCAA AATATCCTGC AAAATCTAAT CAAAACATTG CTAACTTACC
59801  AGTGGTTACC ACCTAAAGAT AAAGCCTTTG TGGATGTAGA AAAATAGACA
59851  TACCTTAGCG AGTACTTCTT AGATTACAGA GTCATGGATT TTTGAAACTG
59901  AAAACAATCA ATTCCCTTCT TTTATAGTTA GGAAAAGAAT ACCCAGAGAT
59951  AATCAGTGGT TTCCCTAAGG CACACAAATA ATCAGAATCT CTTTCTATTG
60001  CAGTACACTG ACTTTACAAT GTAATTAGAA AGAAACCTAT AAAATAAGGC
60051  AGAAATTGGA TGATTAAAAT TGGAGACTGG AAGGTATAAC CAGAGTCACA
60101  GGCTCAGATA TTTAAAAGAG GAGCCAAATA TACCTGAACA AGGTCAGCCT
60151  GACAATTTAA AAAAAAAACA AACCCACCTA AAGTGAATAA TAATGGTTTC
60201  AAGTAGTCTC TATTTGCCAA GAACTCCCAA AGTTGTATTT CAACACAGAC
60251  CCTTCTTCTG AGCTCCAGGC CATGTATCCA CCTTCCTATT TGACATCTCC
60301  ACTTGAATAT TCTCCAGGCA TCTGAAATTT AAGTTGTCAA AAGCTGAACC
60351  TTGATCTTCC CTCCTAAATC TATTTTTCCT CCTGTGCCTC ACATCTTGGT
60401  AATGGCTCCT CTGGCCATCT AGTTACTCAT TCTGGAAACT GGCAAGGATC
60451  CTTAATGCCT CCCACATCTC ATCTTCCACA TTCATCAACA AGCCATGTCT
60501  TTTCCTTCTA TAAAATATGC CTCGAATATG CCCATTTATT GTCATCTCCA
60551  CTGTTGTCAC TCGAGTCCAA GCCATCATTC TTCACCTGGA CCACTATAAA
60601  AGTCTCCTAA CTAGTTCTCT GCTATCACTC CTGCCTCCTC AAATTTGTTT
60651  TCCATGTGGC AGATCATTCT TCTGCTTAGA AGCCTGCAGT GGCCTCCCAT
60701  GTTAATGGGA CAAAAATCTG AAACATTGGC ATAGCCCACA ATGCCCTGTG
60751  GGACCTGGCC CTGCCCACCT CCCAGCCTCA TCCCAGCCAC TTTCCTCTTG
```

FIGURE 3, page 19 of 27

```
60801  GCTTCCTGCA CAAGCTGGTG CCTCCTCTTC CTCAAAACTC CATCCTCTGA
60851  CACTTGCTAA GTGAATCCTT ATATTATAAA CTTCCACTGA AAACTCCCTT
60901  TTTTAAACCT GGTAATCCAA CCAAATGAAT ATATTCNNNN NNNNNNNNNN
60951  NNNNNNNNNN NNNNNNNNNN NNNNNNNNNN NNNNNNGTGC AAAAACTTCT
61001  GGCCTTCCCT GAGGACAGTC AGGGTGGGTC TCTGTCGATT TTTGTTAAGA
61051  ACCGTTCTAA TTAAAAAGAG TTCTAAGCAA TGCTCCATTA GTAATAAATA
61101  ATAGCAAGTC ACAAGGAACC CAGGTCTTAG TCGCATTAGA TTGCTAGTGG
61151  GCCTTGTTTC TCTCTCACTG CATATCTTTG TCCATGTGTG CCATTATACC
61201  AAAATACCCG AGACTGGGTA CTTTATAAAG AAGAGAAGTG TATTCCCCAC
61251  AGTTCTGGAG GCTGGAAGTT CAAGATCAAA GCACCACCAA GTTTATTGTC
61301  TTAGTAAGGG CCCAGTCTCT GCTTCCAAGA TGGCATCTTG TTGCTTGTCC
61351  TCCACAGGGG ACAAATGATG TGTCCTCCCA TGGTGAAAGG CTGGAAGGGC
61401  AACAAAAGGG ACTAGCTAGC TTCCTCAAGC CCTTTTATAA GGGCACTCAT
61451  CCCTTCATAA GGGCTCTTAA TACCAACCCT TGGAGTTTAG GTTTAAACAT
61501  ATGAGTTTGA GAGGGACATA TACATTCAAA CTATGGCACT ATTCATGCCT
61551  TGTATACTTT TCCTTCAGCC ACAGCAGTCA GTTTCACAAC ACTATACCAC
61601  TGTCCAGGAA AGTCATGTCT TTTTTCCTTT GTTTATGCTA CCCTCAGGTT
61651  AGTATGTTCA CTTTCCCCAC CCAACCTCCC CATCCTGCCT GTCTTATTCA
61701  AATGTTATCT CATGAACCAG CTTCCCCACA AATCCCAGGA AGCATGGATC
61751  AAATGTATCA TGGAGGTATA TGTTTGTTTT CTCCCTAGAC TCAAGCTGTT
61801  TAAAAGGAAA GATATAACTT CCTTCTATCT CTATCCCATG ATACGCAGAA
61851  GAGTGCCTGG CACCTAGTAT TAACTCAATA TATTATGTAT TTTTACTTCT
61901  ACGGGATTGA CTCTTGTCAT TGATGTCAAT GGCTAAATAA TGGCTGTTTT
61951  AGAGTACATG TGAGGGTTTT CTTAATCTAC ACAAATCACT TAGCAAAGTG
62001  CTGGCCACAG ATATTTATTG TAACTACTAT TGTTGCTATA ACTGCTGCTG
62051  TTTTGGTATA TAGCAGTAGA GCAGAAAGAG CCCAGGCTTT GGAGCTGAAC
62101  AGAAATGGAC TGAAAGACCA ACTTTGCCAC TTAAAAGTTG CAGTAACTCC
62151  ACTTTCCTTA GTTATAAAAT AGACGTTATA TATCTATTTT AATGTAAAAC
62201  ACTTGGCAGA AAGTAAGCAA CCAATAAATA TCATTAAGTT CCTTCTCTTT
62251  CTCTTCTATG CCTTTTTTGT GGCTTGGCTC GGTTTACTAC ACTTCTCTGG
62301  TCTCACTTTC CTCCTCTGTA AATGAACTAG ATGATTTCCA TGTTCCCTAC
62351  CAGATCCAAA TTCCAAAGTT ACTGAACTCA CCATCTTTTT CCCCTTAAAT
62401  CTACTCATTC TCTTCCCTGA GGGACGTTCT TTCCTTGACA GCTACCAGGT
62451  ATATTAAATT GTTTCAATTC TCTATCTCTA TCTCTCTCAA TCTCTAAGAG
62501  ACCATAAGGT GGTCCAGACC CAGGGCCTTG GCACAACTCC AGGGGCCATT
62551  TGCACAGTGG ATTAACATAC GAATAGCGCC TGTCAACTGA AGAATCATGA
62601  GCTTCATAAA TTTGGCCAGG AGATCTTTAG TTCTCATAAA GGGTTGCAGC
62651  CAGCAGGCCA GCCATCCTGC AGAATGGGAA GCATAGCCTC AGCAGAAGCT
62701  GAGAGCAAGC ACTTCAAGGG AGGGGTAAAA GGGAACAGGA ATTTATGCTG
62751  AGTGGGGTGG CTGAGTATAC GTATTGAGTA AGCTATAGGA GGAGTCATAA
62801  ATATTTATGA AAAGAGATAC ATGCACATGT GCAGTTGAGC TTCATGCCTC
62851  TTCCTGGGCC CATGTTCAAA AAATGGTGGT GTTAGCATGA CCCGAGGGTG
62901  GAGATTTTGG TCTTCTGATG TCCAAATGTG AAGCAGAGGA CATGAAAACC
62951  CTCACTATGC ATCCCCCACA AGTTGGCCAA AACCATCTGG AGATTGTGGT
63001  CATTTTTTAG GAAGGGTGCA TTGGGAAACT GGTGAGCTGT CACACTGAAA
63051  CTGCAAAGAG GGAGGGAGAA TCTGGTTATG GCCTTAGATG ATTAGCTAAA
63101  GGTGATAAAG CAATGAGTTA TCGGTTTCTT GTTTTCCAGA GCTAGCTTTT
63151  GCTTACTTCT TAAGAATGAA TTATGGCTAA AGGTTAATAA GGAAGGGACA
63201  ACTGAGGCAT GACAGACCTC CCATCCAATC AAGGCCAGGA ACTCAGTTTT
63251  TAAGGTTTCT TCGGGGTCCC CATGGACAAG AGAAAGTTCG TTCAGTCGGT
63301  TGGAGAGCTT TTAATTTTAT TTTTATTTCT CACCCTCTAG GCATTGGGTG
63351  CTCCTCGGCA GCCCTCAGTC CAACCCTGGC TGAATTTCTT TCATGATGTA
63401  TAATGAAGGT CACAGAACAC ACAGGGAGAA ATAGTCTCCA GCTGTCCTTA
63451  AGTCCAGAAA AAATGAATAT CCATCTGAAA ACCAAAGAGT ACACAAGCAT
63501  TGGGCCAGGT ATATCATTGT ATTCATGGCC TTTTCTTTCC TATTCTGTCA
63551  CAGACTTTGC AAATGGGCAT CAAACACTTC TCTGGGCTCT TTGTGCTGCT
63601  GTGCATTGGA TTTGGTCTGT CCATTTTGAC CACCATTGGT GAGCACATAG
63651  TATACAGGCT GCTGCTACCA CGAATCAAAA ACAAATCCAA GCTGCAATAC
63701  TGGCTCCACA CCAGCCAGGT GAGTGCCACA GGTGTCTTGC TCCAATATTC
63751  TTAAACTGTA CAATTCCTAG GGATGGGAGG ATCCAGAGCC CTATGTCAGA
63801  CTACTAAGTT ATGTTACCAC AATAACGAGG GTGGGGTAGG CACTCTCATT
63851  AGAGCAGAAG GAATTCTCTC TATCCCATTA ATTCACTTTT CCCTTAAATT
63901  AAGGCATCCC ACAGTGCTCC TTCCTTTCCT ATAACCCTCC ACTGTTGTTC
63951  ATAATAGAAG AAATAGAACT TTTTTAACCA GGTTTCACTT AATAGTGACA
```

FIGURE 3, page 20 of 27

```
64001  GTCTGAAAAG ATGGTGTGAA AGATTTATTT CCTAGGTTCT TTTCTTGCCA
64051  AAATTGAAAC CTATTACGTG AGTTTAAAGT CCCTGGTCCC CTTTAAGTGA
64101  CCCCACTTGC CCCTGTTCTC TCTGCTTTTT CCCTGGTCCA GAGGGGTTTG
64151  AGACCCATTG GGGCCAAGGC CAAGCTTCAC AAGGCCGCAG TTCTCTCCTG
64201  TTACCTAGAC ATCAACGCAC TGATTTACAG GGAGAACTGA AACTGTCAAG
64251  CAGACTGGTG ACTCAAGCAC ACTCGTTTGC ATATCTCTCC CTGAATGAAA
64301  TTGGCATGGA GACCCAAAAT ATAGTCAGAA GGCTTCATAA TGATGGAAGA
64351  ACTCTAACAA AGGGAGTGGT TTCACTTGAC CACAGCAAGG CTGGATGAGC
64401  CATCCTGGCC TCTCCTGTGG TGAGACCACC TCCTGCCCTC CAGTGTACCA
64451  TGGATTACCT CCCAGCAGGG AGGCTGTCAC TTCTGCATTT ACCCTATTCA
64501  TGTATTCATA TACCCTCATA CTAAACTCCT CACTTTGGTA ACACTTTTTT
64551  TTTTTCTAGA TAGGTTACTA TCATTGGTTT GGTTACAGTT GAACCCTGTT
64601  CTTCCTACTT TTATCCTGGG AAGTATTTGG TCTTCTAGGA GAACTCCACA
64651  GATCTTCCTT ATTGTATGCT AATATGATTA ACTTAATTCT CAAGAGTCCT
64701  CCTTCCCTTC TTTGTTTTGG TTGTCAATTA ATTATATACT TTTTACTCAT
64751  CTTTAGCAAT TATGGAAGGC CTTTTGCTAC ACATTAGTTA TGATTGTGCC
64801  TCCTTATATC ACATACCGTT TTATAATACT GAGCTTTCCA TCAGAACACT
64851  TTTTTGTTTC TCCAGGTGGA ATAATAACCT CTAATTAGAA TTTTTGTTCT
64901  GTTGAGATTT GAGGCTGAAT GTTGATCTAT TTTTAGGCAT TTCTGGAATT
64951  TGTTTAAAGA GGCCAAGGTT TGTAACGACT ACATATACTG TTACATCTCA
65001  AGTGGTTCTT TGTTCCCTGA CCTATGTGTT TCTCATAATT TCTACCTGTG
65051  AATCTGTTTT CTCCATCAGA GATTACACAG AGCAATAAAT ACATCATTTA
65101  TAGAGGAAAA GCAGCAGCAT TTCAAGACCA AACGTGTGGA AAAGAGGTAA
65151  GAAGGGGCCA ATGGCAACTG TCTTTATATT TGTAAAATAA TCTTTAGAGA
65201  TCTAACTGTA TAATTATTCA GATCAAATCA GGGCAATTTA TCAAAAGAAT
65251  CAGTATAAAT AGAGGGAAAT AAAACATAAA ATAAAAAATG TATATGGACA
65301  CTAAAATGCA GTGTACACAA TATACTGTCA TGGTTAGAAG TGTAGTCATG
65351  GACTCTAGGA TCAACCCTCT GGATCCAAAT CCTGTCTCCA AGACTTATGA
65401  TATGTGTTAC TTTGTGTAAG TCACTTATTT AATCTCTCTG CACCTCAAGT
65451  TCCTCATTTG TAAAGTAGAG ATAAAAACAG TACCTATTTC CTAGAGTTGT
65501  TGTAAAGATT AAATAAGATC ATACATGTAC ATCTCTGAAT GAAAGGAAAT
65551  GCCTAATAAA TATTAGCTAT TATTATGTAC AAAATACATG TAAGAATTAA
65601  TGAATACCGC AGGCAATTAA TTCCATGTTT TACTGTCTTT TTGGCATATT
65651  TCCACTCCCT ACTCCTTTCT AGCATTCCTA GGAACAGAGT ATTGGAAATA
65701  TGAAACAGAC ATGTCATGCC TAATTCATTT CCTGGCACTT TTCTACAAAC
65751  TCCCTAGCAA AGAGCATCTT ATTAATAGGA AATAACAAAC ATTAAATGCA
65801  TTAATGACAT CTGAAAATCG AAGCTCTTCA CTCTCACCAC ACCAGGCTGT
65851  GGATGACTGT TCCCTATTTC ATGGTGACTA AAGATGTCAG AAGCACTTGG
65901  GTCTGGTTCC TGGCTAGTCT CTGCTGCCTG CTGCCTAAGG CAACCCTACT
65951  GATTCTTTTG TACACCCAGA GGCCTCAGAT GAGGGCACAC CTCTCATCAT
66001  AACAGAAGAA AAAGGGATGG AAAACAGGAT TCTTTTTGTT TGTATCTTTT
66051  CTGGGACTGC TGCAGTCCCC TTCTATGCAG TCTCCATCTA GCTTGTTGGA
66101  ATCATTTCCT TTATCTCTTG AAGTATCTCT TTCCAGTCAA TGAGCACTCT
66151  CCCCTCCCCT CTCAGTCTGT GGTATTCCTG CATCATATTG CAAGTGTGTT
66201  AGTGACAAGC TGTATACTAG TCCAGTCACA GCTGTTCCAT GACATGTTAC
66251  ATCTATTTTT TCTATTTTTA ACATAAATTT TTAATAACAG TAACACAAGA
66301  AGACATAGCA GCAAATGTAT CATCTTACAA TGAAAAAATA TTTGTTTTCC
66351  AGCTATAATA GAAACAGGAA GCCCAATGAT CCCATCTCCA ACTGTGATAT
66401  GATTCATATT CACATCTTTC TCACATAAAT TGAAAACCAT TTGTGTCTTT
66451  TGATGCAACT TACCCAGTTT TCTTGGCAGA TTCCCTTCCT GAACCCCTTA
66501  TTTTGAGGAT CTAAGGAGAA CAGGTGTTCA TGGTTTAGCT TGGGCTCACA
66551  TTTCCTGTGC CTACCTCTAT ACAACCCAAC ATTAGCAACC TGTCAAACAC
66601  AATGAGTGTT TGGCGTACCA TAGCCGTCAT GTCTCTTTGG AATAGTCCAG
66651  TGGAGTATTG AACCTCAGTG TTACATAATT GCTCCAGGGA AGCCTATTTT
66701  ACCCATTTTT AGTGTTAAAT ACAGCTCACT CACTGGTCAC GTAACACTCT
66751  AAGACTGACG AAGGCTTGAA TCAAAGCAAA GCCTAAATGT TACTGAGGCT
66801  AGGAGTATAA CACCAGCCTT GGGTTATTTT TTCCAAGTAG ACACTGAGTC
66851  TTACACTCAG CATTTGTCAC CTTGCACTCA TAGGTACCCA CATCAAATAT
66901  CAGATGCCTG GTGATACTAG CAACTAGAAT TTGGCACAAA GTCCAGCATT
66951  TGTTTATTCT TCTATATTAT ATTACCAGAT AGATATACAA AGCTCTGGAG
67001  AAGACCAGTC CAGCTATCTT TACTTACCTT ATCACTGTGG CTGTCTAGAC
67051  AGTTGAAGAA AATGTGTAGA TGCTCTACTC TCAGGTTTTC CCTGCTATGA
67101  ACCATTGTAG GGCATTAGAA TGCTCTCCCT CTCTTCTCTT GGAAGTATAT
67151  CTATGCAAAT GCTCATGCAT GCTACAACTT GACATCCCTC CTCTGTGCCC
```

FIGURE 3, page 21 of 27

```
67201  CATATTTACT GAACAAATAA AAGAGCAAAT AGATAAATGA ATGAATTATT
67251  AACATGGGTT TGAGGAAATG CTTGGAGAAA TTTTGGGCCA TGATATGGAA
67301  GTAGGTATTG TCCCTTTCTC ATTTAATGCA AAGAAAATAA GGTACATATT
67351  GCAGGAGATG ATTTATATAT AGCCCTGGGT TTATTCAACA TGTGATTTCA
67401  CATAAGGTTT TGGTCTATCT TTCATCTCAC TGGGTTCCCA ATCAATACAT
67451  GTCACCCCTG TTTTCCCTTT CCTCTCACCC CAAGACACAC AAAAATTACA
67501  AACTACATAA CAGCACAACC AAGATTACTT TAAGATTATT CAAATTCAAT
67551  AGGAAAAGAT TTGAAGAAAA AAATTAAAGG GAATTATAAA GCTAGAAGAA
67601  AAATTACATC TCCTCTCTGA CTCAGGTCTA AAGCCAATGG AGCTATAAGT
67651  GGGTTCATTA CAGAACTTTT ACCCAGCCCA GGATACAAGA AAACTGAGCT
67701  CTGGTACCCT CTGCTCATTT ATATAAAACT TAGACTATGA GGCATGTTAA
67751  AGAACCACAG GGTGGTTTGG AGTGTGTGTT TCAATGGCTT GGGTCATGTA
67801  TAAGTTGGTC TTTGCTATGT GATAAATCAT CCCAATACTT AATGTTTTAA
67851  ACAACAGCAA GTTGCTTACT AATTCATGGA TCAACTGTGC AGTTTGCTGA
67901  TCTGAGCCAG ACTTGGCTGA ATTTGGCTGG GTTTGCTCAT ATGTCTGTAG
67951  CCAACTTTGG GGGATGGGGA AAGCAGCTAA GGGCTGTCTG GTCTATGATG
68001  GCCTCAGCTA GTCAACTGGG AAGCCTGAGG ATTCTCTCCA TATGGTCTAC
68051  CATCATGCAG CAGGCCATTC TGGACTTGTT CACATTGCAG CAGCAGGGTT
68101  CCAAGAGAGT GGAAATGTGC AAGACTTCTT AAAAGTTTAG GCTTGGAACT
68151  GCCACTCTGA TATGTCTGCC ACTTTCTGTT GCCCAAAACA AGTTGTGAGA
68201  ACACTCCTAA CTGAAGCGGG GAGGAAAGCA GATTCAGCAT AGGTACAAGC
68251  TGCAAAGTCA CATTACAGAG GGCATAAATG AAAGGAGAAA AGAAGGTTTA
68301  TGGCCACTTT TACATAAAGA CTTTATTATT CTTCTCTTTC CCCTTCTCCT
68351  TCCAGATTGT CCCCTTCTCC TGGCAAGTAA GAGTCCAGGA AAAAAGTCAA
68401  TTCAGTTACA TGAATGGGAA CAAAAACACA ATGGCTTGGT AGGGTGTTTC
68451  TATTTAGTTT TGTCCTGTGG TAGATTGCAA AAGTTGTCAT AACCCTCCTA
68501  CTCCTCCTCC TGCTTCTTCT CCTATGGTGG AAAAAATCAG CAGCTATGCT
68551  GCTTAGGGCT CTAATCTATT CTTGTAGTGA GAAACTCTCC TTATCTCATA
68601  AGTATCAAAG TGTATTTCAG AAACAGGATC AGCCTTCCCC TGTGACTATT
68651  TGGCAATAAT TCTCATGCTG TCTATAGCCA TCTCTCCATG ATGGTAGTAG
68701  GTGATACGAT GCAAGCCTAA AACAGGATTG CAAATTGCTT TCTATATGAC
68751  TTTCATTATC CCAGCAAGAA ACTGAGGGCT TTCTCGGGAT TTTTTTAAGC
68801  ATCGGACCTG ACCTGTCATT CTCAACTCAC ATAAAAATCA TCCCTATAGT
68851  AAGAAACACT TTGCTGAGAC CTGTGGCTTA TATGCTTTTT TTCTCCCCAA
68901  GATCAAGTAG TAAACATCAG GATGGTCCTG TGGGACTAAG GATGAGCCAT
68951  GTTATGAGAT CTGTCAGCAG GTTGATGCTC AGAACCCAAC AAGTGAATAA
69001  ATAGATTTTG CTTTTATTAA AGCATCATCT TTCAAATCAT CAAACGTTTC
69051  AAGGTGTGGC TAGTTTCTGA GCTTCCCTTG CAGAAAGGAA ATTAAAAGCC
69101  ACCTGAGGTT GTTTGCAAAA AAAAAAAAAA AAAAAAAAAA TGCACCATAC
69151  CCCATCCTAT CATCCCTTCA AATGACACCC AATTCCAGTT TCAGAGCAGC
69201  ATGGGACTTG AACTTTTGTA TGTTCATGAC TCTTTATTGC CCCATGACAC
69251  CCTAGCAGGT AGTCTGTCCA TGGCTTTGTT ACTTCATCTC TAAATGCACA
69301  CCCAGCTCCA TATTATTGCA CAGGAAATGG CTAACAGATG AAGACAGCAC
69351  CTTGAGAGCT GCAGAATGGA AAGTAAATCT AAAATTTCTC TGTTTCCTAG
69401  GTCTAATGTG GGACCCCGTC AGCTTACCGT ATGGAATACT TCCAATCTGA
69451  GTCATGACAA CCGACGGAAA TACATCTTTA GTGATGAGGA AGGACAAAAC
69501  CAGCTGGGCA TCCGGATCCA CCAGGACATC CCCCTCCCTC CAAGGAGAAG
69551  AGAGCTCCCT GCCTTGCGGA CCACCAATGG GAAAGCAGAC TCCCTAAATG
69601  TATCTCGGAA CTCAGTGATG CAGGAACTCT CAGAGCTCGA GAAGCAGATT
69651  CAGGTGATCC GTCAGGAGCT GCAGCTGGCT GTGAGCAGGA AAACGGAGCT
69701  GGAGGAGTAT CAAAGGACAA GTCGGACTTG TGAGTCCTAG GTGACCACAC
69751  TGCTTCCCTT TCTCAGTTCC TGACCTTCCT CTGAGCCCTT GAGACACTTT
69801  GTAATGCTCT TTTGTAACTA TCGACAAAGG TGTGGGGAAG CTGAGGTCTA
69851  GGTCTTCTTA AAGGTCAAGT CTGCTCTCCC TCGCCTAAAG TGCAGCAGCA
69901  GCTCCTCTCA AGCTCACTCT CTAGGTCTCC AGGGTAGGAG TGTTTTTCTA
69951  GCAAGAATCT TAGTCAGGAG TAAGCTCTGT GCGAGAGATC TGTGAATAAC
70001  CAGATAACCC CAGCTGCCGT TAACCTTTTC ACCAGGTGCC ACAGTAATAT
70051  TTCTGGTTTT TAGCCCTTTC TCTGCACTAC CAACAAGAGA TAAAATTGTT
70101  ACTCACACTT ATGTCTTACT GGGTTGCTGG TTTTCATCGT AACACAGAAC
70151  GAGGTTATCT AGGGTTGTAG CTTTTGATAC AACTCCCCGA TCTAGATTTA
70201  TTCCTACATT CTGAATGGGG AGCAGGTAAG AGCAGAGCAC CTCCCACTGG
70251  GGGTGGGGTA TTTAAAAATT AACTCATTAG TATCATAAAC GTCAAGGATT
70301  GATTGGACCA GGCAAGAGCC ATGTTTTTGA GAAGGTTCTG GATCTCTGAC
70351  TCCATCCTGA CTGTTTAGTA AGAGCATGCT TACACCCTAC TGTGAAAAGG
```

FIGURE 3, page 22 of 27

70401 GGAGGGGATG TGGTAAGCAG AAACAGAAGA CAGGCAGCAG AGGCATTAAA
70451 AATGCATACC ATGCTTTCAG AACAAAAGCT CTGGGCCAGA AAGGCAATTT
70501 GGCTAAAAAA TGAATAAGAC TACTTCTAAT GTAACTAAGC ATCTCCACTA
70551 TGGTGTGTGC CTTTTATAAA GGAAAAGAGA GAAAAAGGCA AAGCAAGGTT
70601 GTGGCCTTAG GTTGGACCTG GAATATCCCT TATTGCCTAT AATGGAATAT
70651 GTGACACTGT GGGTGAAATG TTCTACACAC CACACACTAG GCCATTTTCA
70701 GATCAGCAGT CACCCATCGC TTAGCATAGA AATCCCAAAA CCTCCAGCCC
70751 GGGAACACTA TAAGCTTCGA CCATTCAGGA ATCTGCCCTG CACTTTGCAT
70801 ATCTGTATAG AAAATCAAGT CAATCCCCCA TCCTCACACC CACTCATCTC
70851 TGAGGAGCTA TGAACTGGTT TTGGTCCCTC TAATGATCCT CCAGCCTCAT
70901 CTAATGCCCC CCAAAGACTG ATACAAGTAA CCTCCCCTCT GCTTAGGTGT
70951 CACTTTCTCA GCATATCAAG TTTAGGCAGC AAGGGAAAGG AATATGGGTC
71001 AGTTCTCAAA TGTCAATGTA GATAAGAGTC ATCTAGTAGA GAACTCATCA
71051 GAGTGCGGAT TGCCAAGACC CTTCTCCAGA GATTATGGGG TTGGGGGTGG
71101 AGGTCTAGAG GTGAGCTCAG AAACCTACTG TTAACCAACA CCCCCAAGTG
71151 ACTGACACAG GTGGTCTAAA AATTACTTTT CTAGAAACAC CATTCTGGAA
71201 GTTTGGCTGC CCACAGGCAG GAGGAGAAGC ATGAAGAGAA AACCTGTTTG
71251 AGAAGTTTTG TTTTGTTTTG TTTTGCTTTT TAATAATTTT AGCACACATC
71301 TGCTGACTCT CCTTCAACAT CCTCACCCCC ACCCCTGGGC ACCATTTAGG
71351 ACAAGACTTC CTTATTTATC AATTACTTGA TTTATCTTCT CAGGACTCAT
71401 TGTTCCACCC CCAACCAATT TGAATGCCTA CAATAAGTTC AGGAGCTGTG
71451 CCAAGCACTT TCCTCTTTTA CAGCTGGAGA TCACTGGAAA GGTGTCTCAG
71501 TCACAAAACT TCTCCCTCTA CTACTGGATG AAATGTCTGC ATTTCCACCA
71551 AAATCTACCC AGTCACCCAG GGAATAACAA CTTAAGCTGT AGTTAGATAA
71601 CACCTAGTGA TTAATTGGCT GAGAAAACCC TGGAGTGGAG GGAGGCTCAG
71651 AGATACTGAT ATGGATGTGG GAGGGCTCTA AAGTTAGAGG TCACCAACTC
71701 CACAGATGAA ACAGTTCAAT AATGAGGAAA CAGGTGAGCC CTGAAAACAC
71751 AAAAGGACAG TTCTGTGTTG AAACACCCCA TCCCCTCACG TTCTCACCCC
71801 AGGCCCAGAA GTAGGTTGCA ACTGCCTTTG GAAGATTTTG CCCCTTAGCC
71851 ATCCCCACCC ACTTGTACCA GCTAAGAATG CTGGAGACTC TGCCACCATG
71901 CTCTGCGTGC CCCTGAACCT CTGTGCAGCC CGGAAGGCTG ATGTACAGGT
71951 GTACCTCAAT CCACATTACA GCCATGCTCC TAATGTACAT GGACATTTTT
72001 GTAACTCAGC TCATATTCTG ACTGTATTTG AGAAGCTGGC TGTTTAAGGG
72051 AACCCAGAAG TGAATTCTTT TGTAAAGTAA AGCACCCTTT TGTAATGCAA
72101 TTAATTATCC CTTAATGTAT CTGTTTTGTA AGTCTGCATT TTTGTATATC
72151 GGATTTACCT TAAGCTTCTC TAGTGAGGCA TTCTGAGCAG TGGTGATCAC
72201 ATGCCAGATC GCCCTGCCTA TCCACAAAGT AGATGACCAA TGCACGCTCC
72251 TCAAACATCT TTGGAGGAAC TACCTGGCCA AAACACTGGC CAGGATGCAG
72301 CAAGCAGCAG CAGGGGCTGA CAGCAGGCTT ACTGCCATCA ACATTGCTTG
72351 AAATGCCTCT ATGTTCTGAA TAAAGAAAAA CCATAATTGC TTGTGGTGAA
72401 ACGAAGCAGT CTTCATGTTA AGTAGCAATG GTTATTTTTA TTGGTAGTAA
72451 CTGAACAGTG TTTTGCAATT TGTGAAACAG TGTATTGTGT TTTGTAAAAT
72501 GATGTCATGA AATGGTGGGT CCTTGGAAAC CTCCTTTCCG TTCAGCTCTG
72551 CCTCTGTTCT TTCAACTCCT TTGAGGCTCA AAAAAAACAC AAAGATCAGA
72601 AGCCTTCAGA TAGAGGGTGG TATTCTGGTA AAGAAGAAAG AGATAAGGGA
72651 CGCTACCTTG CTTTTCTGGC ACAGGAAGCA CATGATAAAG CATGCTCAGA
72701 TGAGCTGGAA CAGATATAGC TACCTGGTTC GTGTAAATAA GAATAATCAA
72751 GGCCCCAGAG TGTGTATGCT TCCAGGTGGA GGAGAAAGGG GAATCTCCCA
72801 AAATTTAAAA ACAAATTGGA AGAATAACCA GGACAGCCAA GTGAAGCAGC
72851 CACAGGGACC CAAGCAGTCG AGGTCTTTAA TGTGCCTGGA GATGACTCTC
72901 TGCTATTCAT GAATCTTGCT ATTGCACAAA CCCTATCAAG AGCTGCTGCT
72951 TCCCTTCCAG CCAGAAAAGT GGTAAGCGGA GCAAGTGCCA AGCAGAACAG
73001 ACCTTATCAT CTGGGTAACA GACTTCTCAG TGTTGGTGCT GTGTCTGTTA
73051 GAGCCTTAGA GCAAGTTAAG CACTTCCTTG GTGTGGGTAA AGAATAAAGG
73101 GGAAAGAAAC TACTTTAGAG CCTCTTTTTC TCCCAACTCA TATTTTTGAT
73151 AGGAAAAACA GAAAACCCAT CCAGTTCTTC AGAAATTGCT TTCTAGGCAT
73201 TAATACTACT TTACTATCTA TACTGTTTAG TTATTCCTTT CTTTACCCAC
73251 CTAAACTATC CATCTAATCC AGGATTCCCT CACTCTTTTT TTTTAGTTAC
73301 TAATCATTTT ATGAAAATAA TGTATTTATA AGTATTTTCT TAAGGTTTGT
73351 GAAGAGTATT TGCATTGTGT CTTCATTTTA ATGTGTTTGC AATCGCTCCG
73401 CTCCAGGAAG AACGGAAATG CTGTCTTGTG AGCATGAAGT GAACGGGCTG
73451 TTTTGCTCCA GCCACTTTTC TTGTACAACC ACATGGATGG ATTAGATGTC
73501 CTCAGGTCTT TTCCATCTTC AGTTTCTATG ACTGTGGAAT AAATGTTCAG
73551 ATAGAAACTT CACTTTTGGA TGTACTGCTG GCTTTGTCTT TGGGGATTCA

```
73601  AATGTTGACA TGATACCAGT TCCTTCTTAA TAGGAGACCC ATTAATGCTA
73651  TGATTTATGC TTATTTCCTT GCTATAGTCC AAAGAAGAAA CACAAGATAT
73701  GCTGAGAAAT CTCAGAGCTC AGGCATCATG AAGTAGAACT GAAATGGCTT
73751  CATCTGAGAT AGACATTCCA GGAAAAAGCA CAAGTTCAGA GGTCTCTAAA
73801  ATCCTGTACT GATCACCCTC ATCAGTAATT CGACAAACAT TTGCTAAACA
73851  GCTTCCATGT ACGTGCCAAG TGCTGGAGAC ACAATAGTGA AGAAGATAGG
73901  TATGGTCCCT AACTTATGAC CTTTTTTCTT TTTTTTTTTT TTTTTTTGAG
73951  ACGGAGTCTT GCTCTGTCAC CAGGATGGAG TGCAGTGGCA TGATCTCGGC
74001  TCACTGCAAC CTCTGCCTCC CAGGTTCAAG TGATTCTCCT GCCTCAGCCT
74051  CCCGCCCGAG TAACTGGGAC TACAGGCGCC TGCCACCATG TCTGGCTAAT
74101  TTTTTGTATT TTAGTAGAGA TGGAGTTTCA ACATGTTGGC CAGGATGGTA
74151  TCGATCTCCT TACCTCGTGA TCCACCCACC TCGGCCTCCC AAAGTGTGGG
74201  GATTACAGGC ATGAGCCACC ACGCCCACCC TCAATCTGAC CTTTTTACAA
74251  CCTATAAACA GGTAATACTG TAACAACTAA CATATATTGG GTACTTATTA
74301  TAAACCATGA TCTCATTTAA TCTTAACAAC CCCACAAGAT AGGCACTATA
74351  GATGTAGTCT TAAGTAGGTA AATGAGACCT CCCAGTTTAC AGATAAAAAA
74401  ACAAGAGTCA GAGAAACTAT GTAACTTGCC CAAGGTTGCA GAACTAGTAA
74451  TAGTAACAGA GATTTGTACA ACCATACAGG ATTCCGGTCA CTGCCTCACA
74501  ATTTTCTATT CTTCCTTGAA TCCCCTTTTA GTCTTTCTGC CTTACTGCTT
74551  CTTTCCCATG CCTCGGCCTG GCCCCTAGCT CCACAG (SEQ ID NO:3)
```

FEATURES:

| | | |
|---|---|---|
| Start: | 1651 | |
| Exon: | 1651 | 2349 |
| Intron: | 2350 | 29157 |
| Exon: | 29158 | 29762 |
| Intron: | 29763 | 44435 |
| Exon: | 44436 | 45483 |
| Intron: | 45484 | 52584 |
| Exon: | 52585 | 52730 |
| Intron: | 52731 | 57554 |
| Exon: | 57555 | 57670 |
| Intron: | 57671 | 59239 |
| Exon: | 59240 | 59391 |
| Intron: | 59392 | 63553 |
| Exon: | 63554 | 63718 |
| Intron: | 63719 | 65069 |
| Exon: | 65070 | 65149 |
| Intron: | 65150 | 69400 |
| Exon: | 69401 | 69740 |
| Stop: | 69738 | |

MAP POSITION FOR ALLELIC VARIANTS:

STS that hits the 3' end of the cDNA:

WI-14669
dbSTS id: 37082, GenBank Accession: G23244
Organism: Homo sapiensPrimer1: TCATAGAAACTGAAGATGGAAAAGA (SEQ ID NO:5)
Primer2: GGAAGAACGGAAATGCTGTCSTS (SEQ ID NO:6) location: 7633..7759 Chromosome: 9

GB4 Map: Chr.9
Reference interval: D9S176-D9S279 (104.9-120.4 cM)
Physical position: 326.27 cR3000 (P2.11)
RH details: RHdb RH62705
Typed by: Whitehead (see WI-14669)

RH mapping panel:

| | # | SHGCNAME | CHROM# | LOD_SCORE | DIST.(cRs) |
|---|---|---|---|---|---|
| 11000282865712 | 1 | SHGC-9736 | 9 | 8.23 | 29 |
| | 2 | SHGC-57676 | 9 | 6.4 | 40 |

FIGURE 3, page 24 of 27 blast match to HTG:
Coverage by HTG sequence AL137023.1:
Regions Covered:
1922 - 2971
2970 - 3118
3123 - 3234
3232 - 3385
3384 - 3550
3548 - 3629
3626 - 5481
5509 - 7789

HTG sequence, submitted 20-Jan-2000
emb|AL137023.1|AL137023 Homo sapiens chromosome 9 clone RP11-403A22 map q34.13-34.3, * SEQUENCING IN PROGRESS *, 19 unordered pieces
Length = 184814

Score = 4389 bits (2214), Expect = 0.0
Identities = 2261/2281 (99%), Gaps = 1/2281 (0%)

Allelic Variants (SNPs):

| | | | |
|---|---|---|---|
| 3,248 | g | a | atttgtgaacttaacgttgacaagtaataatgaggagatgaatctttaag[g/a]acaagac agagtccttatttagtaatgagttttctgccttttatatgtta (SEQ ID NO:7) |
| 9,928 | g | a | cttatgaaacaggagtgagcttattttggtgtggtagggctgagtacctg[g/a]aagagtt ccaaatctgaatcctcaaacttgtgaatatgttatttttat (SEQ ID NO:8) |
| 11,387 | t | c | agtacaacctgcatgcaatctatgggtgttttggacagaaggcctcaac[t/c]agaagcc aaacagaagttgtgttaatactccccagattaaaagaaaagt (SEQ ID NO:9) |
| 11,578 | c | t | aaccagacattcttaaacagagattcctttaaacaaataatttgcttcta[c/t]atattgt aaatgtaataatgggagcaaatatatacacagatccacacaca (SEQ ID NO:10) |
| 11,731 | a | g | cacattgtgttatacacataaagaaatgcttcaatgtgacctgaacatga[a/g]tgataaa tctagatccgaatttatctagtgtgccttcacctggccacaga (SEQ ID NO:11) |
| 14,101 | t | c | aggaatttctaacttgaaattgtggttatatctccaattctcaccttaag[t/c]taaaaat acttaaagatgtcttgaaaaagtgtttttctcttacctataac (SEQ ID NO:12) |
| 14,437 | c | t | cttatcaaatataatgccctgagcttcatgccattcccttgctcaaaaac[c/t]attttac tataataatattccctttctttttccatgacccaacacttctg (SEQ ID NO:13) |
| 16,732 | T(17) | T(16) | ccattgaaacactgaaatttaaatggcctcctaacccatcctttaccacc[t/-]ttttttttttttttttaagatggagtctcacactgttgcctgggctggag (SEQ ID NO:14) |
| 18,612 | a | c | ctcctgtcaaacaaagtatcgggaaatcagacaagagttcagatcttggt[a/c]agattag ccaagtctattcctaacttcctgttttactcactgctcatccg (SEQ ID NO:15) |
| 18,968 | a | g | acctgggaaaaaaaatcacatttggtagttttaaagtatagaatttta[a/g]cctcact gaattccactatattatatgctatgacctcatatatctgtttt (SEQ ID NO:16) |
| 20,360 | a | g | cttccaattttgtttttctgggaggttattgttttctgttttatttgcc[a/g]ttgtaat tcaagggtctattacactgttttgctcatagtaatcactcaga (SEQ ID NO:17) |
| 23,731 | t | a | ctactcactgccttgtctacctcatttgttcttccacttagttctgtaac[t/a]ttgaagc agctctgaagtacagtgaaacccatgacctggtttgaagctag (SEQ ID NO:18) |
| 26,282 | a | t | ttaagccatcatgttgatagatcataaaatgacatctatcattctctgag[a/t]ctttcat aactgaaaaaggaataaatgcagtgtagagtcaggctagagtg (SEQ ID NO:19) |
| 29,047 | t | g | tagacaggaagcatagttttccaaactatgggaattttatcccagaacta[t/g]gtatcac agtgaaattaaaggattaagcctcataagaaagcaaaagtacc (SEQ ID NO:20) |
| 29,346 | c | t | ctcctccttacccagaataattccaagttccaccttggttctatcatcaa[c/t]atcaccg ctaacctcccctccacccaggacctcttgagcttcctacagat (SEQ ID NO:21) |
| 29,542 | a | g | ttggggtcatgccccctgaacttcgttgggtgctgggagattcccagaat[a/g]tggagga actgaggacagagggtctgcccttaggactcattgctcatgga (SEQ ID NO:22) |
| 29,577 | a | g | ggagattcccagaatatggaggaactgaggacagagggtctgcccttagg[a/g]ctcattg ctcatggaaaaacaacacagtctgtctttgagcactacgtaca (SEQ ID NO:23) |

FIGURE 3, page 25 of 27

| | | | |
|---|---|---|---|
| 29,779 | c | t | ctacaaatctcacttcaggacaatatttatcaaggtaggatgcaaggtct[c/t]ggttata<br>tccccattcatagggccatgacagagagtaaaattcccctatc (SEQ ID NO:24) |
| 32,135 | c | t | aaaaaaaattagctaagcatgctggcaccgcgactgtagtcccagctacg[c/t]gggaggc<br>tgatgcaggagaatcgcttgaacctgggaggcagaggttgcag (SEQ ID NO:25) |
| 33,150 | g | t | gctgacagaactgttaacatcttaaaatgttaatgaaatcaccaaaaaca[g/t]ggcattt<br>tcagctaggctttcagattagaaaagtcatttctcatggcaga (SEQ ID NO:26) |
| 35,710 | g | a | taagcattcttgtcctaaggacctctaccaacacaaactggttaacccac[g/a]tatttca<br>acatgtacttaaaagaaatgcagttgcattaaacatggaagcc (SEQ ID NO:27) |
| 37,765 | a | g | ctcaagaaatcacgcacatttaatgtttaatttggagaactgtcccatat[a/g]tggagaa<br>gaaaatcaaacagaattggaccacaggtaagctctgtggctaa (SEQ ID NO:28) |
| 38,468 | g | a | ctggaggtctatggacattgtgaaatatcaaaattggctgtaagagttct[g/a]aaagaca<br>atccaaagagagaatagcttagggctcttgaatgaaaaagagc (SEQ ID NO:29) |
| 38,915 | g | a | tcagtaaacctaacaagaattaggtgatcctggtaggaagggagtttgag[g/a]gaatgtt<br>actagtaataatattcttaaagattcctaatcaggcaaaagca (SEQ ID NO:30) |
| 39,464 | g | c | gtgataatatgtagacagaaatgaaggctgaaaacaatggagttatttca[g/c]agctatt<br>tccacagccagaaaaaatacaaattcataataaacataaaaac (SEQ ID NO:31) |
| 41,195 | g | a | ccaccttaagccctttatgagactagcagagagagagtaaaagaggaagc[g/a]aaagaaa<br>gaaggaagaagcattgttcctcacatgtggacttatgttcagt (SEQ ID NO:32) |
| 44,478 | t | c | tttcccaggtttctagccaataccactttcagaggcctcagtggttccat[t/c]agagtaa<br>aaggttccaccatcgtcagctcagaaaacaactttttcatctg (SEQ ID NO:33) |
| 51,524 | a | g | tatggcagtggttgcaggtatttatctttgtcaccctagtaactttgaga[a/g]ctctaca<br>gagtaggccttcaataagtgttgaataaatgaacgatttgct (SEQ ID NO:34) |
| 54,016 | t | g | tgagctactgctgcagtccccagcagttccactccactcagggcattcac[t/g]tatctca<br>ggagctttacctgagaaggcccacgtgcccagcactggccctg (SEQ ID NO:35) |
| 54,405 | a | c | cttcattttaacaagctccccaggcaattcactgattgaggtgaaattgg[a/c]atctagg<br>cagagcttatcattaatgccctctcaccacttctctctgggcc (SEQ ID NO:36) |
| 55,007 | c | t | cgccttttcacgtaactgaaatttatcatagctatctgcactttgcagtc[c/t]aaaatca<br>agagtagttatttaaggaaggatcccagagacattaggcttca (SEQ ID NO:37) |
| 55,156 | t | g | tcatattgctaccacaaatatttgtggaatattggcaagtgataacttgt[t/g]gctacgt<br>agctgtcaaggtacattatggtactgtggcagtcgaactttga (SEQ ID NO:38) |
| 64,177 | t | c | ttttccctggtccagaggggtttgagacccattggggccaaggccaagct[t/c]cacaagg<br>ccgcagttctctcctgttacctagacatcaacgcactgattta (SEQ ID NO:39) |
| 66,196 | c | g | actctcccctcccctctcagtctgtggtattcctgcatcatattgcaagt[c/g]tgttagt<br>gacaagctgtatactagtccagtcacagctgttccatgacatg (SEQ ID NO:40) |
| 66,780 | a | g | tcactggtcacgtaacactctaagactgacgaaggcttgaatcaaagcaa[a/g]gcctaaa<br>tgttactgaggctaggagtataacaccagccttgggttatttt (SEQ ID NO:41) |
| 69,176 | t | c | aaaaaaaaaaaaaatgcaccataccccatcctatcatcccttcaaatga[t/c]acccaat<br>tccagtttcagagcagcatgggacttgaactttgtatgttca (SEQ ID NO:42) |
| 70,027 | a | g | catccccctccctccaaggagaagagagctccctgccttgcggaccacca[a/g]tgggaaa<br>gcagactccctaaatgtatctcggaactcagtgatgcaggaac (SEQ ID NO:43) |
| 70,419 | a | g | taagagcatgcttacaccctactgtgaaaaggggaggggatgtggtaagc[a/g]gaaacag<br>aagacaggcagcagaggcattaaaaatgcataccatgctttca (SEQ ID NO:44) |
| 71,332 | c | t | aataattttagcacacatctgctgactctccttcaacatcctcaccccca[c/t]ccctggg<br>caccatttaggacaagacttccttatttatcaattacttgatt (SEQ ID NO:45) |
| 72,153 | a | g | aattatcccttaatgtatctgttttgtaagtctgcatttttgtatatcgg[a/g]tttacct<br>taagcttctctagtgaggcattctgagcagtggtgatcacatg (SEQ ID NO:46) |
| 72,711 | t | g | cgctaccttgctttctggcacaggaagcacatgataaagcatgctcaga[t/g]gagctgg<br>aacagatatagctacctggttcgtgtaaataagaataatcaag (SEQ ID NO:47) |
| 74,434 | g | c | agtttacagataaaaaaacaagagtcagagaaactatgtaacttgcccaa[g/c]gttgcag<br>aactagtaatagtaacagagatttgtacaaccatacaggattc (SEQ ID NO:48) |

FIGURE 3, page 26 of 27

| POSITION | Allele 1 | Allele 2 | | Protein Position | | |
|---|---|---|---|---|---|---|
| 3,248 | g | a | Intron | | | |
| 9,928 | g | a | Intron | | | |
| 11,387 | t | c | Intron | | | |
| 11,578 | c | t | Intron | | | |
| 11,731 | a | g | Intron | | | |
| 14,101 | t | c | Intron | | | |
| 14,437 | c | t | Intron | | | |
| 16,732 | T(17) | T(16) | Intron | | | |
| 18,612 | a | c | Intron | | | |
| 18,968 | a | g | Intron | | | |
| 20,360 | a | g | Intron | | | |
| 23,731 | t | a | Intron | | | |
| 26,282 | a | t | Intron | | | |
| 29,047 | t | g | Intron | | | |
| 29,346 | c | t | Exon | 296 | N | N |
| 29,542 | a | g | Exon | | | |
| 29,577 | a | g | Exon | | | |
| 29,779 | c | t | Intron | | | |
| 32,135 | c | t | Intron | | | |
| 33,150 | g | t | Intron | | | |
| 35,710 | g | a | Intron | | | |
| 37,765 | a | g | Intron | | | |
| 38,468 | g | a | Intron | | | |
| 38,915 | g | a | Intron | | | |
| 39,464 | g | c | Intron | | | |
| 41,195 | g | a | Intron | | | |
| 44,478 | t | c | Exon | | | |
| 51,524 | a | g | Intron | | | |
| 54,016 | t | g | Intron | | | |
| 54,405 | a | c | Intron | | | |
| 55,007 | c | t | Intron | | | |
| 55,156 | t | g | Intron | | | |
| 64,177 | t | c | Intron | | | |
| 66,196 | c | g | Intron | | | |
| 66,780 | a | g | Intron | | | |
| 69,176 | t | c | Intron | | | |
| 70,027 | a | g | Exon | | | |
| 70,419 | a | g | Intron | | | |
| 71,332 | c | t | Intron | | | |
| 72,153 | a | g | Intron | | | |
| 72,711 | t | g | Intron | | | |
| 74,434 | g | c | Intron | | | |

FIGURE 3, page 27 of 27

SEQUENCE LISTING

<160> NUMBER OF SEQ ID NOS: 6

<210> SEQ ID NO 1
<211> LENGTH: 1017
<212> TYPE: DNA
<213> ORGANISM: human

<400> SEQUENCE: 1

```
atgccctttt gccacaatat aattaatatt tcctgtgtga aaaacaactg gtcaaatgat      60
gtccgtgctt ccctgtacag tttaatggtg ctcataattc tgaccacact cgttggcaat     120
ctgatagtta ttgtttctat atcacacttc aaacaacttc ataccccaac aaattggctc     180
attcattcca tggccactgt ggactttctt ctggggtgtc tggtcatgcc ttacagtatg     240
gtgagatctg ctgagcactg ttggtatttt ggagaagtct tctgtaaaat tcacacaagc     300
accgacatta tgctgagctc agcctccatt ttccatttgt ctttcatctc cattgaccgc     360
tactatgctg tgtgtgatcc actgagatat aaagccaaga tgaatatctt ggttatttgt     420
gtgatgatct tcattagttg gagtgtccct gctgtttttg catttggaat gatctttctg     480
gagctaaact tcaaaggcgc tgaagagata tattacaaac atgttcactg cagaggaggt     540
tgctctgtct tctttagcaa aatatctggg gtactgacct ttatgacttc tttttatata     600
cctggatcta ttatgttatg tgtctattac agaatatatc ttatcgctaa agaacaggca     660
agattaatta gtgatgccaa tcagaagctc caaattggat tggaaatgaa aaatggaatt     720
tcacaaagca aagaaaggaa agctgtgaag acattgggga ttgtgatggg agttttccta     780
atatgctggt gccctttctt tatctgtaca gtcatggacc cttttcttca ctacattatt     840
ccacctactt tgaatgatgt attgatttgg tttggctact tgaactctac atttaatcca     900
atggtttatg catttttcta tccttggttt agaaaagcac tgaagatgat gctgtttggt     960
aaaattttcc aaaaagattc atccaggtgt aaattatttt tggaattgag ttcatag       1017
```

<210> SEQ ID NO 2
<211> LENGTH: 338
<212> TYPE: PRT
<213> ORGANISM: human

<400> SEQUENCE: 2

```
Met Pro Phe Cys His Asn Ile Ile Asn Ile Ser Cys Val Lys Asn Asn
 1               5                  10                  15

Trp Ser Asn Asp Val Arg Ala Ser Leu Tyr Ser Leu Met Val Leu Ile
            20                  25                  30

Ile Leu Thr Thr Leu Val Gly Asn Leu Ile Val Ile Val Ser Ile Ser
        35                  40                  45

His Phe Lys Gln Leu His Thr Pro Thr Asn Trp Leu Ile His Ser Met
    50                  55                  60

Ala Thr Val Asp Phe Leu Leu Gly Cys Leu Val Met Pro Tyr Ser Met
65                  70                  75                  80

Val Arg Ser Ala Glu His Cys Trp Tyr Phe Gly Glu Val Phe Cys Lys
                85                  90                  95

Ile His Thr Ser Thr Asp Ile Met Leu Ser Ser Ala Ser Ile Phe His
            100                 105                 110

Leu Ser Phe Ile Ser Ile Asp Arg Tyr Tyr Ala Val Cys Asp Pro Leu
        115                 120                 125

Arg Tyr Lys Ala Lys Met Asn Ile Leu Val Ile Cys Val Met Ile Phe
```

-continued

```
    130                 135                 140

Ile Ser Trp Ser Val Pro Ala Val Phe Ala Phe Gly Met Ile Phe Leu
145                 150                 155                 160

Glu Leu Asn Phe Lys Gly Ala Glu Glu Ile Tyr Tyr Lys His Val His
                165                 170                 175

Cys Arg Gly Gly Cys Ser Val Phe Phe Ser Lys Ile Ser Gly Val Leu
            180                 185                 190

Thr Phe Met Thr Ser Phe Tyr Ile Pro Gly Ser Ile Met Leu Cys Val
        195                 200                 205

Tyr Tyr Arg Ile Tyr Leu Ile Ala Lys Glu Gln Ala Arg Leu Ile Ser
    210                 215                 220

Asp Ala Asn Gln Lys Leu Gln Ile Gly Leu Glu Met Lys Asn Gly Ile
225                 230                 235                 240

Ser Gln Ser Lys Glu Arg Lys Ala Val Lys Thr Leu Gly Ile Val Met
                245                 250                 255

Gly Val Phe Leu Ile Cys Trp Cys Pro Phe Phe Ile Cys Thr Val Met
            260                 265                 270

Asp Pro Phe Leu His Tyr Ile Ile Pro Pro Thr Leu Asn Asp Val Leu
        275                 280                 285

Ile Trp Phe Gly Tyr Leu Asn Ser Thr Phe Asn Pro Met Val Tyr Ala
    290                 295                 300

Phe Phe Tyr Pro Trp Phe Arg Lys Ala Leu Lys Met Met Leu Phe Gly
305                 310                 315                 320

Lys Ile Phe Gln Lys Asp Ser Ser Arg Cys Lys Leu Phe Leu Glu Leu
                325                 330                 335

Ser Ser


<210> SEQ ID NO 3
<211> LENGTH: 3501
<212> TYPE: DNA
<213> ORGANISM: human

<400> SEQUENCE: 3

tgtgtgcctt gcccacggcc cacatggaaa ctcagcttcc ctgggctctc acctcagtgc     60

tctttgcacc atgccacttc acttcttacc atagacttta gtctgtatat caaaaatcct    120

taataagtgg gaccacaata tcattcttca ctagtaggtg ccattattta agacatcaaa    180

aattcttata tgaaaattta aaccttaatt tttaaaaatt gacctcaagt tggttctttc    240

tgcaatagag agaaagactg gactgatatc aaagaaactg aactagtaat tgagaccaca    300

gctcatattc aagctttaat gatttgtgaa ttaaacttca atttcttgcc agtaaaatga    360

ggttaatgaa gcatgtcatg tcttccttac aaaaaatgat gttggtctta taaatgtcaa    420

ataaaactgt aactgaaata atgcatggaa tatatgtaga agtactttgc aagctgcaaa    480

taaatatatg taagcttctt cttattacaa ttaattataa aataagaaat atataattta    540

cgtatgacca agtgcagaag tgggcatagt gcgtattaat tctgcacaag aggcacattt    600

aaaagacttc ttgtcttttt cataaacata ttttaattcc aaattttctg gcaattttct    660

ttctaccctt tacaatgtaa gtctccccca ctagactggc ttcctatgga cacagtattg    720

tttccataga ttaagatgtg tgatcataat catcatttga tcttctctga cctacaaatg    780

tggcagtttc atatagttca acctaataat ttagcttcat atttctagaa gaatgtccag    840

ctccaggtaa aagtttttta aaaattgctg tactgaacta ttgaatggaa cttggaaata    900

aagtcccttc caaaataact attcttcaac agagagtaat aggtaaatgt tttagaagtg    960
```

-continued

```
agaggactca aattgccaat gatttactct tttatttttc ctcctaggtt tctgggataa   1020
gtatgtgcaa ataaaaaata aacatgagaa ggaactgtaa cctgattatg gatttgggaa   1080
aaagataaat caacacacaa agggaaaagt aaactgattg acagccctca ggaatgatgc   1140
ccttttgcca caatataatt aatatttcct gtgtgaaaaa caactggtca aatgatgtcc   1200
gtgcttccct gtacagttta atggtgctca taattctgac cacactcgtt ggcaatctga   1260
tagttattgt ttctatatca cacttcaaac aacttcatac cccaacaaat tggctcattc   1320
attccatggc cactgtggac tttcttctgg ggtgtctggt catgccttac agtatggtga   1380
gatctgctga gcactgttgg tattttggag aagtcttctg taaaattcac acaagcaccg   1440
acattatgct gagctcagcc tccattttcc atttgtcttt catctccatt gaccgctact   1500
atgctgtgtg tgatccactg agatataaag ccaagatgaa tatcttggtt atttgtgtga   1560
tgatcttcat tagttggagt gtccctgctg tttttgcatt tggaatgatc tttctggagc   1620
taaacttcaa aggcgctgaa gagatatatt acaaacatgt tcactgcaga ggaggttgct   1680
ctgtcttctt tagcaaaata tctggggtac tgacctttat gacttctttt tatatacctg   1740
gatctattat gttatgtgtc tattacagaa tatatcttat cgctaaagaa caggcaagat   1800
taattagtga tgccaatcag aagctccaaa ttggattgga aatgaaaaat ggaatttcac   1860
aaagcaaaga aaggaaagct gtgaagacat tggggattgt gatgggagtt ttcctaatat   1920
gctggtgccc tttctttatc tgtacagtca tggacccttt tcttcactac attattccac   1980
ctactttgaa tgatgtattg atttggtttg gctacttgaa ctctacattt aatccaatgg   2040
tttatgcatt tttctatcct tggtttagaa aagcactgaa gatgatgctg tttggtaaaa   2100
ttttccaaaa agattcatcc aggtgtaaat tatttttgga attgagttca tagaattatt   2160
atattttact gttttgcaaa tcggttgatg atcatattta tgaacacaac ataacgaacc   2220
acatgcacca accacatgga ttttttttta aatcagttac ttgagtcaaa gtatgtatgg   2280
tgagttaaat tatgatgctt ataggtaatt tcctatttgg gacatagtag gtatacgctt   2340
ttccattctt accacacata atggaacttt gcaaatccag tatttaaagg cctacatttt   2400
atataacttt tcctgccctt agaagaactg ccatgagttt actgtggtac cttagtcagc   2460
tgttcagtgg tggaaactat agggctgaat ttgaggatgc aaatcagaat gattttgtca   2520
tatacgtata catgtcctgg tcacatatgt gtataagtct tttagtaaaa tcaactaaaa   2580
gtacacacat taaatgttac cgctaaataa ttgttgacac ataatttatt tgtattgtta   2640
atatatattc caatccttaa atatcttgat cttcacattt ttaaattatg tttttctgat   2700
tctcatgctt ctaagaaatt tgaaaaataa aggaaaatat aaaaataaaa tatatacaaa   2760
ccaaatgaaa ttaaaaaaat gttattcata gtatacttcc tggtaaggat tatatcatct   2820
aaaattcttt attttatatt aatatttctc tttttcaact tttattttgg agtcggggca   2880
tatgtgcaca tattaactaa atataatgca tgatgctgag gtttgagcta tgagtaatcc   2940
ctttttgtgg ctgtataacg tgactgcaca gatgtacaaa tatattttta accattccct   3000
attgttaatt ccagttgttt ctaacttttc taaaaataat ataaattaaa tgaaattcct   3060
gctttttacc tgccactgaa gtcatgaaaa tgtctagaag gattttacca tgtcttaagg   3120
tcatatctgg catgataggg ttcaaaacac aggctacctg gtattaaaca aattcacttt   3180
gctgggctcc acaatacaca gaaggagaag cagtcatcca tcaaagtagc taaacatgag   3240
ggccaacaag aagtataatc agactagatg taccatggct atttagatgg catatataaa   3300
```

-continued

```
aatacaaaag aggaacaaat aatggtttca aataagattc tctaaaggaa gtgggcaaac   3360

attctaaatt acaagcattc atcagcaatt gagctgatga atacaaactt cacatggtct   3420

gtttcagatt gagtatcacc ggggatttgg atttaccttc tgctcatgaa taagttaggg   3480

taaggcaaat gattttaaac g                                              3501
```

<210> SEQ ID NO 4
<211> LENGTH: 290
<212> TYPE: PRT
<213> ORGANISM: human

<400> SEQUENCE: 4

```
Met Tyr Ser Phe Met Ala Gly Ser Ile Phe Ile Thr Ile Phe Gly Asn
 1               5                  10                  15

Leu Ala Met Ile Ile Ser Ile Ser Tyr Phe Lys Gln Leu His Thr Pro
            20                  25                  30

Thr Asn Phe Leu Ile Leu Ser Met Ala Ile Thr Asp Phe Leu Leu Gly
        35                  40                  45

Phe Thr Ile Met Pro Tyr Ser Met Ile Arg Ser Val Glu Asn Cys Trp
    50                  55                  60

Tyr Phe Gly Leu Thr Phe Cys Lys Ile Tyr Tyr Ser Phe Asp Leu Met
65                  70                  75                  80

Leu Ser Ile Thr Ser Ile Phe His Leu Cys Ser Val Ala Ile Asp Arg
                85                  90                  95

Phe Tyr Ala Ile Cys Tyr Pro Leu Leu Tyr Ser Thr Lys Ile Thr Ile
            100                 105                 110

Pro Val Ile Lys Arg Leu Leu Leu Leu Cys Trp Ser Val Pro Gly Ala
        115                 120                 125

Phe Ala Phe Gly Ala Val Phe Ser Glu Ala Tyr Ala Asp Gly Ile Glu
    130                 135                 140

Gly Tyr Asp Ile Leu Val Ala Cys Ser Ser Ser Cys Pro Val Met Phe
145                 150                 155                 160

Asn Lys Leu Trp Gly Thr Thr Leu Phe Met Ala Gly Phe Phe Thr Pro
                165                 170                 175

Gly Ser Met Met Val Gly Ile Tyr Gly Lys Ile Phe Ala Val Ser Arg
            180                 185                 190

Lys His Ala His Ala Ile Asn Asn Leu Arg Glu Asn Gln Asn Asn Gln
        195                 200                 205

Val Lys Lys Asp Lys Lys Ala Ala Lys Thr Leu Gly Ile Val Ile Gly
    210                 215                 220

Val Phe Leu Leu Cys Trp Phe Pro Cys Phe Phe Thr Ile Leu Leu Asp
225                 230                 235                 240

Pro Phe Leu Asn Phe Ser Thr Pro Val Val Leu Phe Asp Ala Leu Thr
                245                 250                 255

Trp Phe Gly Tyr Phe Asn Ser Thr Cys Asn Pro Leu Ile Tyr Gly Phe
            260                 265                 270

Phe Tyr Pro Trp Phe Arg Arg Ala Leu Lys Tyr Ile Leu Leu Gly Lys
        275                 280                 285

Ile Phe
    290
```

<210> SEQ ID NO 5
<211> LENGTH: 101
<212> TYPE: DNA
<213> ORGANISM: human

-continued

```
<400> SEQUENCE: 5

tgagctgatg aatacaaact tcacatggtc tgtttcagat tgagtatcac yggggatttg     60

gatttacctt ctgctcatga ataagttagg gtaaggcaaa t                        101


<210> SEQ ID NO 6
<211> LENGTH: 101
<212> TYPE: DNA
<213> ORGANISM: human

<400> SEQUENCE: 6

aactataggg ctgaatttga ggatgcaaat cagaatgatt ttgtcatata ygtatacatg     60

tcctggtcac atatgtgtat aagtctttta gtaaaatcaa c                        101
```

ISOLATED HUMAN G-PROTEIN COUPLED RECEPTORS THAT ARE MEMBERS OF THE AMINERGIC SUBFAMILY, NUCLEIC ACID MOLECULES ENCODING HUMAN GPCR PROTEINS, AND USES THEREOF

RELATED APPLICATIONS

The present application claims priority to U.S. Ser. No. 60/192,311, filed Mar. 27, 2000.

FIELD OF THE INVENTION

The present invention is in the field of G-Protein coupled receptors (GPCRs) that are related to the aminergic receptor subfamily, recombinant DNA molecules and protein production. The present invention specifically provides novel GPCR peptides and proteins and nucleic acid molecules encoding such protein molecules, for use in the development of human therapeutics and human therapeutic development.

BACKGROUND OF THE INVENTION

G-protein coupled receptors

G-protein coupled receptors (GPCRs) constitute a major class of proteins responsible for transducing a signal within a cell. GPCRs have three structural domains: an amino terminal extracellular domain, a transmembrane domain containing seven transmembrane segments, three extracellular loops, and three intracellular loops, and a carboxy terminal intracellular domain. Upon binding of a ligand to an extracellular portion of a GPCR, a signal is transduced within the cell that results in a change in a biological or physiological property of the cell. GPCRs, along with G-proteins and effectors (intracellular enzymes and channels modulated by G-proteins), are the components of a modular signaling system that connects the state of intracellular second messengers to extracellular inputs.

GPCR genes and gene-products are potential causative agents of disease (Spiegel et al., *J. Clin Invest.* 92:1119–1125 (1993); McKusicketal., *J. Med. Genet.* 30:1–26(1993)). Specific defects in the rhodopsin gene and the V2 vasopressin receptor gene have been shown to cause various forms of retinitis pigmentosum (Nathans et al, *Annu. Rev. Genet.* 26:403–424(1992)), and nephrogenic diabetes insipidus (Holtzman et al., *Hum. Mol. Genet.* 2:1201–1204 (1993)). These receptors are of critical importance to both the central nervous system and peripheral physiological processes. Evolutionary analyses suggest that the ancestor of these proteins originally developed in concert with complex body plans and nervous systems.

The GPCR protein superfamily can be divided into five families: Family I, receptors typified by rhodopsin and the β2-purinergic receptor and currently represented by over 200 unique members (Dohlman et al., *Annu. Rev. Biochem.* 60:653–688 (1991)); Family II, the parathyroid hormone/calcitonin/secretin receptor family (Juppner et al., *Science* 254:1024–1026 (1991); Lin et al., *Science* 254:1022–1024 (1991)); Family III, the metabotropic glutamate receptor family (Nakanishi, *Science* 258 597:603 (1992)); Family IV, the cAMP receptor family, important in the chemotaxis and development of *D. discoideum* (Klein et al., *Science* 241:1467–1472 (1988)); and Family V, the fungal mating pheromone receptors such as STE2 (Kurjan, *Annu. Rev. Biochem.* 61:1097–1129 (1992)).

There are also a small number of other proteins that present seven putative hydrophobic segments and appear to be unrelated to GPCRs; they have not been shown to couple to G-proteins. *Drosophila* expresses a photoreceptor-specific protein, bride of sevenless (boss), a seven-transmembrane-segment protein that has been extensively studied and does not show evidence of being a GPCR (Hart et al., *Proc. Natl. Acad. Sci. USA* 90:5047–5051 (1993)). The gene frizzled (fz) in *Drosophila* is also thought to be a protein with seven transmembrane segments. Like boss, fz has not been shown to couple to G-proteins (Vinson et al., *Nature* 338:263–264 (1989)).

G proteins represent a family of heterotrimeric proteins composed of α, β and γ subunits, that bind guanine nucleotides. These proteins are usually linked to cell surface receptors, e.g., receptors containing seven transmembrane segments. Following ligand binding to the GPCR, a conformational change is transmitted to the G protein, which causes the α-subunit to exchange a bound GDP molecule for a GTP molecule and to dissociate from the βγ-subunits. The GTP-bound form of the α-subunit typically functions as an effector-modulating moiety, leading to the production of second messengers, such as cAMP (e.g., by activation of adenyl cyclase), diacylglycerol or inositol phosphates. Greater than 20 different types of α-subunits are known in humans. These subunits associate with a smaller pool of β and γ subunits. Examples of mammalian G proteins include Gi, Go, Gq, Gs and Gt. G proteins are described extensively in Lodish et al., *Molecular Cell Biology*, (Scientific American Books Inc., New York, N.Y., 1995), the contents of which are incorporated herein by reference. GPCRs, G proteins and G protein-linked effector and second messenger systems have been reviewed in *The G-Protein Linked Receptor Fact Book*, Watson et al., eds., Academic Press (1994).

Aminergic GPCRs

One family of the GPCRS, Family II, contains receptors for acetylcholine, catecholamine, and indoleamine ligands (hereafter referred to as biogenic amines). The biogenic amine receptors (aminergic GPCRs) represent a large group of GPCRs that share a common evolutionary ancestor and which are present in both vertebrate (deuterostome), and invertebrate (protostome) lineages. This family of GPCRs includes, but is not limited to the 5-HT-like, the dopamine-like, the acetylcholine-like, the adrenaline-like and the melatonin-like GPCRs.

Dopamine receptors

The understanding of the dopaminergic system relevance in brain function and disease developed several decades ago from three diverse observations following drug treatments. These were the observations that dopamine replacement therapy improved Parkinson's disease symptoms, depletion of dopamine and other catecholamines by reserpine caused depression and antipsychotic drugs blocked dopamine receptors. The finding that the dopamine receptor binding affinities of typical antipsychotic drugs correlate with their clinical potency led to the dopamine overactivity hypothesis of schizophrenia (Snyder, S. H., *Am J Psychiatry* 133, 197–202 (1976); Seeman, P. and Lee, T., *Science* 188, 1217–9 (1975)). Today, dopamine receptors are crucial targets in the pharmacological therapy of schizophrenia, Parkinson's disease, Tourette's syndrome, tardive dyskinesia and Huntington's disease. The dopaminergic system includes the nigrostriatal, mesocorticolimbic and tuberoinfindibular pathways. The nigrostriatal pathway is part of the striatal motor system and its degeneration leads to Parkinson's disease; the mesocorticolimbic pathway plays a key role in reinforcement and in emotional expression and is the desired site of action of antipsychotic drugs; the tuberoinfundibular pathways regulates prolactin secretion from the pituitary.

Dopamine receptors are members of the G protein coupled receptor superfamily, a large group proteins that share a seven helical membrane-spanning structure and transduce signals through coupling to heterotrimeric guanine nucleotide-binding regulatory proteins (G proteins). Dopamine receptors are classified into subfamilies: D1-like (D1 and D5) and D2-like (D2, D3 and D4) based on their different ligand binding profiles, signal transduction properties, sequence homologies and genomic organizations (Civelli, O., Bunzow, J. R. and Grandy, D. K., *Annu Rev Pharmacol Toxicol* 33, 281–307 (1993)). The D1-like receptors, D1 and D5, stimulate cAMP synthesis through coupling with Gs-like proteins and their genes do not contain introns within their protein coding regions. On the other hand, the D2-like receptors, D2, D3 and D4, inhibit cAMP synthesis through their interaction with Gi-like proteins and share a similar genomic organization which includes introns within their protein coding regions.

Serotonin receptors

Serotonin (5-Hydroxytryptanine; 5-HT) was first isolated from blood serum, where it was shown to promote vasoconstriction (Rapport, M. M., Green, A. A. and Page, I. H., *J Biol Chem* 176, 1243–1251 (1948). Interest on a possible relationship between 5-HT and psychiatric disease was spurred by the observations that hallucinogens such as LSD and psilocybin inhibit the actions of 5-HT on smooth muscle preparations (Gaddum, J. H. and Hameed, K. A., *Br J Pharmacol* 9, 240–248 (1954)). This observation lead to the hypothesis that brain 5-HT activity might be altered in psychiatric disorders (Wooley, D. W. and Shaw, E., *Proc Natl Acad Sci USA* 40,228–231 (1954); Gaddum, J. H. and Picarelli, Z. P., *Br J Pharmacol* 12, 323–328(1957)). This hypothesis was strengthened by the introduction of tricyclic antidepressants and monoamine oxidase inhibitors for the treatment of major depression and the observation that those drugs affected noradrenaline and 5-HT metabolism. Today, drugs acting on the serotoninergic system have been proved to be effective in the pharmacotherapy of psychiatric diseases such as depression, schizophrenia, obsessive-compulsive disorder, panic disorder, generalized anxiety disorder and social phobia as well as migraine, vomiting induced by cancer chemotherapy and gastric motility disorders.

Serotonin receptors represent a very large and diverse family of neurotransmitter receptors. To date thirteen 5-HT receptor proteins coupled to G proteins plus one ligand gated ion channel receptor (5-HT3) have been described in mammals. This receptor diversity is thought to reflect serotonin's ancient origin as a neurotransmitter and a hormone as well as the many different roles of 5-HT in mammals. The 5-HT receptors have been classified into seven subfamilies or groups according to their different ligand-binding affinity profiles, molecular structure and intracellular transduction mechanisms (Hoyer, D. et al., *Pharmacol. Rev.* 46, 157–203 (1994)).

Adrenergic GPCRs

The adrenergic receptors comprise one of the largest and most extensively characterized families within the G-protein coupled receptor "superfamily". This superfamily includes not only adrenergic receptors, but also muscarinic, cholinergic, dopaminergic, serotonergic, and histaminergic receptors. Numerous peptide receptors include glucagon, somatostatin, and vasopressin receptors, as well as sensory receptors for vision (rhodopsin), taste, and olfaction, also belong to this growing family. Despite the diversity of signalling molecules, G-protein coupled receptors all possess a similar overall primary structure, characterized by 7 putative membrane-spanning .alpha. helices (Probst et al., 1992). In the most basic sense, the adrenergic receptors are the physiological sites of action of the catecholamines, epinephrine and norepinephrine. Adrenergic receptors were initially classified as either .alpha. or .beta. by Ahlquist, who demonstrated that the order of potency for a series of agonists to evoke a physiological response was distinctly different at the 2 receptor subtypes (Ahlquist, 1948). Functionally, .alpha. adrenergic receptors were shown to control vasoconstriction, pupil dilation and uterine inhibition, while .beta. adrenergic receptors were implicated in vasorelaxation, myocardial stimulation and bronchodilation (Regan et al., 1990). Eventually, pharmacologists realized that these responses resulted from activation of several distinct adrenergic receptor subtypes..beta. adrenergic receptors in the heart were defined as .beta..sub.1, while those in the lung and vasculature were termed .beta..sub.2 (Lands et al., 1967).

.alpha. Adrenergic receptors, meanwhile, were first classified based on their anatomical location, as either pre or post-synaptic (.alpha..sub.2 and .alpha..sub.1, respectively) (Langer et al., 1974). This classification scheme was confounded, however, by the presence of .alpha..sub.2 receptors in distinctly non-synaptic locations, such as platelets (Berthelsen and Pettinger, 1977). With the development of radioligand binding techniques, .alpha. adrenergic receptors could be distinguished pharmacologically based on their affinities for the antagonists prazosin or yohimbine (Stark, 1981). Definitive evidence for adrenergic receptor subtypes, however, awaited purification and molecular cloning of adrenergic receptor subtypes. In 1986, the genes for the hamster .beta..sub.2 (Dickson et al., 1986) and turkey .beta..sub.1 adrenergic receptors (Yarden et al., 1986) were cloned and sequenced. Hydropathy analysis revealed that these proteins contain 7 hydrophobic domains similar to rhodopsin, the receptor for light. Since that time the adrenergic receptor family has expanded to include 3 subtypes of .beta. receptors (Emorine et al., 1989), 3 subtypes of .alpha..sub.1 receptors (Schwinn et al., 1990), and 3 distinct types of .beta..sub.2 receptors (Lomasney et al., 1990).

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1 a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Martin C. Michel, et al., Naunyn-Schmiedeberg's Arch. Pharmacol. (1995) 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting the flow of urine through the urethra.

The .alpha..sub.2 receptors appear to have diverged rather early from either .beta. or .alpha..sub.1 receptors. The .alpha..sub.2 receptors have been broken down into 3 molecularly distinct subtypes termed .alpha..sub.2C2, .alpha..sub.2C4, and .alpha..sub.2 C10 based on their chromosomal location. These subtypes appear to correspond to the pharmacologically defined .alpha..sub.2B, .alpha..sub.2C, and alpha..sub.2A subtypes, respectively (Bylund et al., 1992). While all the receptors of the adrenergic type are recognized by epinephrine, they are pharmacologically distinct and are encoded by separate genes. These receptors are generally coupled to different second messenger pathways that are linked through G-proteins. Among the adrenergic receptors, .beta..sub.1 and beta..sub.2 receptors activate the adenylate cyclase, .alpha..sub.2 receptors inhibit adenylate cyclase and .alpha..sub.1 receptors activate phospholipase C pathways, stimulating breakdown of polyphosphoinositides (Chung, F. Z. et al., J. Biol. Chem., 263:4052 (1988)).alpha..sub.1 and .alpha..sub.2 adrenergic receptors differ in their cell activity for drugs.

Issued US patents that disclose the utility of members of this family of proteins include, but are not limited to, U.S. Pat. No. 6,063,785 Phthalimido arylpiperazines useful in the treatment of benign prostatic hyperplasia; U.S. Pat. No. 6,060,492 Selective .beta.3 adrenergic agonists; U.S. Pat. No. 6,057,350 Alpha 1a adrenergic receptor antagonists; U.S. Pat. No. 6,046,192 Phenylethanolaminotetralincarboxamide derivatives; U.S. Pat. No. 6,046,183 Method of synergistic treatment for benign prostatic hyperplasia; U.S. Pat. No. 6,043,253 Fused piperidine substituted arylsulfonamides as .beta.3-agonists; U.S. Pat. No. 6,043,224 Compositions and methods for treatment of neurological disorders and neurodegenerative diseases; U.S. Pat. No. 6,037,354 Alpha 1a adrenergic receptor antagonists; U.S. Pat. No. 6,034,106 Oxadiazole benzenesulfonamides as selective .beta..sub.3 Agonist for the treatment of Diabetes and Obesity; U.S. Pat. No. 6,011,048 Thiazole benzenesulfonamides as .beta.3 agonists for treatment of diabetes and obesity; U.S. Pat. No. 6,008,361 U.S. Pat. No. 5,994,506 Adrenergic receptor; U.S. Pat. No. 5,994,294 Nitrosated and nitrosylated .alpha.-adrenergic receptor antagonist compounds, compositions and their uses; U.S. Pat. No. 5,990, 128.alpha..sub.1C specific compounds to treat benign prostatic hyperplasia; U.S. Pat. No. 5,977,154 Selective .beta.3 adrenergic agonist; U.S. Pat. No. 5,977,115 Alpha 1a adrenergic receptor antagonists; U.S. Pat. No. 5,939,443 Selective .beta.3 adrenergic agonists; U.S. Pat. No. 5,932,538 Nitrosated and nitrosylated .alpha.-adrenergic receptor antagonist compounds, compositions and their uses; U.S. Pat. No. 5,922,722 Alpha 1a adrenergic receptor antagonists 26 U.S. Pat. Nos. 5,908,830 and 5,861,309 DNA endoding human alpha 1 adrenergic receptors.

GPCRs, particularly members of the aminergic receptor subfamily, are a major target for drug action and development. Accordingly, it is valuable to the field of pharmaceutical development to identify and characterize previously unknown GPCRs. The present invention advances the state of the art by providing a previously unidentified human GPCR.

SUMMARY OF THE INVENTION

The present invention is based in part on the identification of nucleic acid sequences that encode amino acid sequences of human GPCR peptides and proteins that are related to the aminergic subfamily, allelic variants thereof and other mammalian orthologs thereof. These unique peptide sequences, and nucleic acid sequences that encode these peptides, can be used as models for the development of human therapeutic targets, aid in the identification of therapeutic proteins and serve as targets for the development of human therapeutic agents.

The proteins of the present inventions are GPCRs that participate in signaling pathways mediated by the aminergic subfamily in cells that express these proteins (see expression information in FIG. 1, the GPCR of the present invention is expressed in fetal brain, brain, placenta, liver, stomach and kidney). As used herein, a "signaling pathway" refers to the modulation (e.g., stimulation or inhibition) of a cellular function/activity upon the binding of a ligand to the GPCR protein. Examples of such functions include mobilization of intracellular molecules that participate in a signal transduction pathway, e.g., phosphatidylinositol 4,5-bisphosphate ($PIP_2$), inositol 1,4,5-triphosphate ($IP_3$) and adenylate cyclase; polarization of the plasma membrane; production or secretion of molecules; alteration in the structure of a cellular component; cell proliferation, e.g., synthesis of DNA; cell migration; cell differentiation; and cell survival.

The response mediated by the receptor protein depends on the type of cell it is expressed on. Some information regarding the types of cells that express other members of the subfamily of GPCRs of the present invention is already known in the art (see references cited in Background and information regarding closest homologous protein provided in FIG. 2 and expression information provided in FIG. 1 (the GPCR of the present invention is expressed in fetal brain, brain, placenta, liver, stomach and kidney). For example, in some cells, binding of a ligand to the receptor protein may stimulate an activity such as release of compounds, gating of a channel, cellular adhesion, migration, differentiation, etc., through phosphatidylinositol or cyclic AMP metabolism and turnover while in other cells, the binding of the ligand will produce a different result. Regardless of the cellular activity/response modulated by the particular GPCR of the present invention, a skilled artisan will clearly know that the receptor protein is a GPCR and interacts with G proteins to produce one or more secondary signals, in a variety of intracellular signal transduction pathways, e.g., through phosphatidylinositol or cyclic AMP metabolism and turnover, in a cell thus participating in a biological process in the cells or tissues that express the GPCR (the GPCR of the present invention is expressed in fetal brain, brain, placenta, liver, stomach and kidney (FIG. 1)).

As used herein, "phosphatidylinositol turnover and metabolism" refers to the molecules involved in the turnover and metabolism of phosphatidylinositol 4,5-bisphosphate ($PIP_2$) as well as to the activities of these molecules. $PIP_2$ is a phospholipid found in the cytosolic leaflet of the plasma membrane. Binding of ligand to the receptor activates, in some cells, the plasma-membrane enzyme phospholipase C that in turn can hydrolyze $PIP_2$ to produce 1,2-diacylglycerol (DAG) and inositol 1,4,5-triphosphate ($IP_3$). Once formed $IP_3$ can diffuse to the endoplasmic reticulum surface where it can bind an $IP_3$ receptor, e.g., a calcium channel protein containing an $IP_3$ binding site. $IP_3$ binding can induce opening of the channel, allowing calcium ions to be released into the cytoplasm. $IP_3$ can also be phosphorylated by a specific kinase to form inositol 1,3,4,5-tetraphosphate ($IP_4$), a molecule that can cause calcium entry into the cytoplasm from the extracellular medium. $IP_3$ and $IP_4$ can subsequently be hydrolyzed very rapidly to the inactive products inositol 1,4-biphosphate ($IP_2$) and inositol 1,3,4-triphosphate, respectively. These inactive products can be recycled by the cell to synthesize $PIP_2$. The other second messenger produced by the hydrolysis of $PIP_2$, namely 1,2-diacylglycerol (DAG), remains in the cell membrane where it can serve to activate the enzyme protein kinase C. Protein kinase C is usually found soluble in the cytoplasm of the cell, but upon an increase in the intracellular calcium concentration, this enzyme can move to the plasma membrane where it can be activated by DAG. The activation of protein kinase C in different cells results in various cellular responses such as the phosphorylation of glycogen synthase, or the phosphorylation of various transcription factors, e.g., NF-KB. The language "phosphatidylinositol activity", as used herein, refers to an activity of $PIP_2$ or one of its metabolites.

Another signaling pathway in which the receptor may participate is the cAMP turnover pathway. As used herein, "cyclic AMP turnover and metabolism" refers to the molecules involved in the turnover and metabolism of cyclic AMP (cAMP) as well as to the activities of these molecules. Cyclic AMP is a second messenger produced in response to ligand-induced stimulation of certain G protein coupled receptors. In the cAMP signaling pathway, binding of a ligand to a GPCR can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

By targeting an agent to modulate a GPCR, the signaling activity and biological process mediated by the receptor can be agonized or antagonized in specific cells and tissues (the GPCR of the present invention is expressed in fetal brain, brain, placenta, liver, stomach and kidney (FIG. 1)). Such agonism and antagonism serves as a basis for modulating a biological activity in a therapeutic context (mammalian therapy) or toxic context (anti-cell therapy, e.g. anti-cancer agent).

DESCRIPTION OF THE FIGURE SHEETS

FIG. 1 provides the nucleotide sequence of a cDNA molecule or transcript sequence that encodes the GPCR of the present invention. In addition structure and functional information is provided, such as ATG start, stop and tissue distribution, where available, that allows one to readily determine specific uses of inventions based on this molecular sequence (the GPCR of the present invention is expressed in fetal brain, brain, placenta, liver, stomach and kidney (FIG. 1)).

FIG. 2 provides the predicted amino acid sequence of the GPCR of the present invention. In addition structure and functional information, such as protein family and function, modification sites, is provided that allows one to readily determine specific uses of inventions based on this molecular sequence as well as significant fragments of the proteins of the present invention.

FIG. 3 provides genomic sequences that span the gene encoding the GPCR protein of the present invention. In addition structure and functional information, such as intron/exon structure, promoter location, etc., is provided that allows one to readily determine specific uses of inventions based on this molecular sequence as well as important fragments for use in probe and primer design and heterologous gene expression control. FIG. 3 also provides SNP information that has been found in the gene encoding the GPCR protein of the present invention. The following variations were seen: C3440T and C2525T.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a GPCR protein or part of a GPCR protein, that are related to the aminergic subfamily. Utilizing these sequences, additional genomic sequences were assembled and transcript and/or cDNA sequences were isolated and characterized. Based on this analysis, the present invention provides amino acid sequences of human GPCR peptides and proteins, nucleic acid sequences in the form of transcript sequences, cDNA sequences and/or genomic sequences that encode these GPCR peptides and proteins, nucleic acid variation (allelic information), tissue distribution of expression, and information about the closest art known protein/peptide/domain that has structural or sequence homology to the GPCR of the present invention.

In addition to being previously unknown, the peptides that are provided in the present invention are selected based on their ability to be used for the development of commercially important products and services. Specifically, the present peptides are selected based on homology and/or structural relatedness to known GPCR proteins of the aminergic subfamily and the expression pattern observed (the GPCR of the present invention is expressed in fetal brain, brain, placenta, liver, stomach and kidney (FIG. 1)). The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the know aminergic family or subfamily of GPCR proteins.

Specific Embodiments

Peptide Molecules

The present invention provides nucleic acid sequences that encode protein molecules that have been identified as being members of the GPCR family of proteins (protein sequences are provided in FIG. 2, transcript/cDNA sequences are provided in FIG. 1 and genomic sequences are provided in FIG. 3). The peptide sequences provided in FIG. 2, as well as the obvious variants described herein, such as allelic variants, will be referred herein as the GPCR peptides of the present invention, GPCR peptides, or peptides/proteins of the present invention.

The present invention provides isolated peptide and protein molecules that consist of, consist essentially of or are comprised of the amino acid sequences of the GPCR peptides disclosed in the FIG. 2, (encoded by the nucleic acid molecule shown in FIG. 1, transcript/cDNA and FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the GPCR peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated GPCR peptide can be purified from cells that naturally express it, purified from cells that have been altered to express it (recombinant), or synthesized using known protein synthesis methods (the GPCR of the present invention is expressed in fetal brain, brain, placenta, liver, stomach and kidney (FIG. 1)). For example, a nucleic acid molecule encoding the GPCR peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). The amino acid sequence that such a protein consists of is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that are comprised of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein is comprised of an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the GPCR peptides of the present invention are the naturally occurring mature proteins. A brief description of how various types of these proteins can be made/isolated is provided below.

The GPCR peptides of the present invention can be attached to heterologous sequences to form chimeric or fusion proteins. Such chimeric and fusion proteins comprise a GPCR peptide operatively linked to a heterologous protein having an amino acid sequence not substantially homologous to the GPCR peptide. "Operatively linked" indicates that the GPCR peptide and the heterologous protein are fused in-frame. The heterologous protein can be fused to the N-terminus or C-terminus of the GPCR peptide.

In some uses, the fusion protein does not affect the activity of the GPCR peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant GPCR peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A GPCR peptide-encoding nucleic acid can be cloned into such an expression vector such that the fusion moiety is linked in-frame to the GPCR peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the GPCR peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; Biocomputing: *Informatics and Genome Projects*, Smith, D. W., ed., Academic Press, New York, 1993*; Computer Analysis of Sequence Data, Part* 1, Griffin, A. M., and Griffin, H. G., eds., Humana Press, New Jersey, 1994*; Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM 120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*NucleicAcids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the GPCR peptides of the present invention as well as being encoded by the same genetic locus as the GPCR peptide provided herein. map position was determined to be on chromosome 6 near markers SHGC-1836 (LOD=13.79) and SHGC-12753 (LOD=9.94) (FIG. 3).

Allelic variants of a GPCR peptide can readily be identified as being a human protein having a high degree (significant) of sequence homology/identity to at least a portion of the GPCR peptide as well as being encoded by the same genetic locus as the GPCR peptide provided herein. Genetic locus can readily be determined based on the genomic information provided in FIG. 3, such as the genomic sequence mapped to the reference human (map position was determined to be on chromosome 6 near markers SHGC-1836 (LOD=13.79) and SHGC-12753 (LOD=9.94) (FIG. 3)). As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a GPCR peptide encoding nucleic acid molecule under stringent conditions as more fully described below.

FIG. 3 provides SNP information that has been found in the gene encoding the GPCR protein of the present invention. The following variations were seen: C3440T and C2525T.

Paralogs of a GPCR peptide can readily be identified as having some degree of significant sequence homology/identity to at least a portion of the GPCR peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a GPCR peptide encoding nucleic acid molecule under moderate to stringent conditions as more fully described below.

Orthologs of a GPCR peptide can readily be identified as having some degree of significant sequence homology/identity to at least a portion of the GPCR peptide as well as being encoded by a gene from another organism. Preferred orthologs will be isolated from mammals, preferably primates, for the development of human therapeutic targets and agents. Such orthologs will be encoded by a nucleic acid sequence that will hybridize to a GPCR peptide encoding nucleic acid molecule under moderate to stringent conditions, as more fully described below, depending on the degree of relatedness of the two organisms yielding the proteins.

Non-naturally occurring variants of the GPCR peptides of the present invention can readily be generated using recombinant techniques. Such variants include, but are not limited to deletions, additions and substitutions in the amino acid sequence of the GPCR peptide. For example, one class of substitutions are conserved amino acid substitution. Such substitutions are those that substitute a given amino acid in a GPCR peptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

Variant GPCR peptides can be fully functional or can lack function in one or more activities, e.g. ability to bind ligand, ability to bind G-protein, ability to mediate signaling, etc. Fully functional variants typically contain only conservative variation or variation in non-critical residues or in non-critical regions. FIG. 2 provides the result of protein analysis that identifies critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as ligand/effector molecule binding or in assays such as an in vitro proliferative activity. Sites that are critical for ligand-receptor binding can also be determined by structural analysis such as crystallization, nuclear magnetic resonance or photoaffimity labeling (Smith et al., *J. Mol. Biol.* 224:899–904 (1992); de Vos et al. *Science* 255:306–312 (1992)).

The present invention further provides fragments of the GPCR peptides, in addition to proteins and peptides that comprise and consist of such fragments, particularly fragments identified in FIG. 2. The fragments to which the invention pertains, however, are not to be construed as encompassing fragments that may be disclosed publicly prior to the present invention.

As used herein, a fragment comprises at least 8 10, 12, 14, 16 or more contiguous amino acid residues from a GPCR peptide. Such fragments can be chosen based on the ability to retain one or more of the biological activities of the GPCR peptide or could be chosen for the ability to perform a function, e.g. ability to bind ligand or effector molecule or act as an immunogen. Particularly important fragments are biologically active fragments, peptides which are, for example, about 8 or more amino acids in length. Such fragments will typically comprise a domain or motif of the GPCR peptide, e.g., active site, a G-protein binding site, a transmembrane domain or a ligand-binding domain. Further, possible fragments include, but are not limited to, domain or motif containing fragments, soluble peptide fragments, and fragments containing immunogenic structures. Predicted domains and functional sites are readily identifiable by computer programs well-known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in GPCR peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Accordingly, the GPCR peptides of the present invention also encompass derivatives or analogs in which a substituted amino acid residue is not one encoded by the genetic code, in which a substituent group is included, in which the mature GPCR peptide is fused with another compound, such as a compound to increase the half-life of the GPCR peptide (for example, polyethylene glycol), or in which the additional amino acids are fused to the mature GPCR peptide, such as a leader or secretory sequence or a sequence for purification of the mature GPCR peptide or a pro-protein sequence.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad Sci* 663:48–62 (1992)).

Protein/Peptide Uses

The proteins of the present invention can be used in substantial and specific assays related to the functional information provided in the Figures and Back Ground Section; to raise antibodies or to elicit another immune response; as a reagent (including the labeled reagent) in assays designed to quantitatively determine levels of the protein (or its binding partner or receptor) in biological fluids; and as markers for tissues in which the corresponding protein is preferentially expressed (either constitutively or at a particular stage of tissue differentiation or development or in a disease state). Where the protein binds or potentially binds to another protein (such as, for example, in a receptor-ligand interaction), the protein can be used to identify the binding partner so as to develop a system to identify inhibitors of the binding interaction. Any or all of these research utilities are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, GPCRs isolated from humans and their human/mammalian orthologs serve as targets for identifying agents for use in mammalian therapeutic applications, e.g. a human drug to modulate the cells or tissues that express the receptor (the GPCR of the present invention is expressed in fetal brain, brain, placenta, liver, stomach and kidney (FIG. 1)). Approximately 70% of all pharmaceutical agents modulate the activity of a GPCR. A combination of the invertebrate and mammalian ortholog can be used in selective screening methods to find agents specific for invertebrates. The structural and functional information provided in the Background and Figures provide specific and substantial uses for the molecules of the present invention. Such uses can readily be determined using the information provided herein, that known in the art and routine experimentation.

The receptor polypeptides (including variants and fragments that may have been disclosed prior to the present invention) are useful for biological assays related to GPCRs. Such assays involve any of the known GPCR functions or activities or properties useful for diagnosis and treatment of GPCR-related conditions that are specific for the subfamily of GPCRs that the one of the present invention belongs to, particularly in cells and tissues that express this receptor (the GPCR of the present invention is expressed in fetal brain, brain, placenta, liver, stomach and kidney (FIG. 1)).

The receptor polypeptides are also useful in drug screening assays, in cell-based or cell-free systems. Cell-based systems can be native, i.e., cells that normally express the receptor protein, as a biopsy or expanded in cell culture (the GPCR of the present invention is expressed in fetal brain, brain, placenta, liver, stomach and kidney (FIG. 1)). In one embodiment, however, cell-based assays involve recombinant host cells expressing the receptor protein.

The polypeptides can be used to identify compounds that modulate receptor activity of the protein in its natural state, or an altered form that causes a specific disease or pathology associated with the receptor. Both the GPCRs of the present invention and appropriate variants and fragments can be used in high-throughput screens to assay candidate compounds for the ability to bind to the receptor. These compounds can be further screened against a functional receptor to determine the effect of the compound on the receptor activity. Further, these compounds can be tested in animal or invertebrate systems to determine activity/effectiveness. Compounds can be identified that activate (agonist) or inactivate (antagonist) the receptor to a desired degree.

Further, the receptor polypeptides can be used to screen a compound for the ability to stimulate or inhibit interaction between the receptor protein and a molecule that normally interacts with the receptor protein, e.g. a ligand or a component of the signal pathway that the receptor protein normally interacts (for example, a G-protein or other interactor involved in cAMP or phosphatidylinositol turnover and/or adenylate cyclase, or phospholipase C activation). Such assays typically include the steps of combining the receptor protein with a candidate compound under conditions that allow the receptor protein, or fragment, to interact with the target molecule, and to detect the formation of a complex between the protein and the target or to detect the biochemical consequence of the interaction with the receptor protein and the target, such as any of the associated effects of signal transduction such as G-protein phosphorylation, cAMP or phosphatidylinositol turnover, and adenylate cyclase or phospholipase C activation.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for ligand binding. Other candidate compounds include mutant receptors or appropriate fragments containing mutations that affect receptor function and thus compete for ligand. Accordingly, a fragment that competes for ligand, for example with a higher affinity, or a fragment that binds ligand but does not allow release, is encompassed by the invention.

The invention further includes other end point assays to identify compounds that modulate (stimulate or inhibit) receptor activity. The assays typically involve an assay of events in the signal transduction pathway that indicate receptor activity. Thus, a cellular process such as proliferation, the expression of genes that are up- or down-regulated in response to the receptor protein dependent signal cascade, can be assayed. In one embodiment, the regulatory region of such genes can be operably linked to a marker that is easily detectable, such-as luciferase.

Any of the biological or biochemical functions mediated by the receptor can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the receptor can be assayed (the GPCR of the present invention is expressed in fetal brain, brain, placenta, liver, stomach and kidney (FIG. 1)).

Binding and/or activating compounds can also be screened by using chimeric receptor proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a G-protein-binding region can be used that interacts with a different G-protein then that which is recognized by the native receptor. Accordingly, a different set of signal transduction components is available as an end-point assay for activation. Alternatively, the entire transmembrane portion or subregions (such as transmembrane segments or intracellular or extracellular loops) can be replaced with the entire transmembrane portion or subregions specific to a host cell that is different from the host cell from which the amino terminal extracellular domain and/or the G-protein-binding region are derived. This allows for assays to be performed in other than the specific host cell from which the receptor is derived. Alternatively, the amino terminal extracellular domain (and/or other ligand-binding regions) could be replaced by a domain (and/or other binding region) binding a different ligand, thus, providing an assay for test compounds that interact with the heterologous amino terminal extracellular domain (or region) but still cause signal transduction. Finally, activation can be detected by a reporter gene containing an easily detectable coding region operably linked to a transcriptional regulatory sequence that is part of the native signal transduction pathway.

The receptor polypeptides are also useful in competition binding assays in methods designed to discover compounds that interact with the receptor. Thus, a compound is exposed to a receptor polypeptide under conditions that allow the compound to bind or to otherwise interact with the polypeptide. Soluble receptor polypeptide is also added to the mixture. If the test compound interacts with the soluble receptor polypeptide, it decreases the amount of complex formed or activity from the receptor target. This type of assay is particularly useful in cases in which compounds are sought that interact with specific regions of the receptor. Thus, the soluble polypeptide that competes with the target receptor region is designed to contain peptide sequences corresponding to the region of interest.

To perform cell free drug screening assays, it is sometimes desirable to immobilize either the receptor protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of receptor-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a receptor-binding protein and a candidate compound are incubated in the receptor protein-presenting wells and the amount of complex trapped in the well can be quantitated. Methods for detecting such complexes, in addition to those described above for the GST-immobilized complexes, include immunodetection of complexes using antibodies reactive with the receptor protein target molecule, or which are reactive with receptor protein and compete with the target molecule, as well as enzyme-linked assays which rely on detecting an enzymatic activity associated with the target molecule.

Agents that modulate one of the GPCRs of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of receptor protein activity identified according to these drug screening assays can be used to treat a subject with a disorder mediated by the receptor pathway, by treating cells or tissues that express the GPCR (the GPCR of the present invention is expressed in fetal brain, brain, placenta, liver, stomach and kidney (FIG. 1)). These methods of treatment include the steps of administering a modulator of the GPCR's activity in a pharmaceutical composition to a subject in need of such treatment, the modulator being identified as described herein.

In yet another aspect of the invention, the GPCR proteins can be used as "bait proteins" in a two-hybrid assay or three-hybrid assay (see, e.g., U.S. Pat. No. 5,283,317; Zervos et al. (1993) Cell 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the GPCR and are involved in GPCR activity. Such GPCR-binding proteins are also likely to be involved in the propagation of signals by the GPCR proteins or GPCR targets as, for example, downstream elements of a GPCR-mediated signaling pathway. Alternatively, such GPCR-binding proteins are likely to be GPCR inhibitors.

The two-hybrid system is based on the modular nature of most transcription factors, which consist of separable DNA-binding and activation domains. Briefly, the assay utilizes two different DNA constructs. In one construct, the gene that codes for a GPCR protein is fused to a gene encoding the DNA binding domain of a known transcription factor (e.g., GALA). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a GPCR-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the GPCR protein.

This invention further pertains to novel agents identified by the above-described screening assays. Accordingly, it is within the scope of this invention to further use an agent identified as described herein in an appropriate animal model. For example, an agent identified as described herein (e.g., a GPCR modulating agent, an antisense GPCR nucleic acid molecule, a GPCR-specific antibody, or a GPCR-binding partner) can be used in an animal or other model to determine the efficacy, toxicity, or side effects of treatment with such an agent. Alternatively, an agent identified as described herein can be used in an animal or insect model to determine the mechanism of action of such an agent. Furthermore, this invention pertains to uses of novel agents identified by the above-described screening assays for treatments as described herein.

The GPCR proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism (the GPCR of the present invention is expressed in fetal brain, brain, placenta, liver, stomach and kidney (FIG. 1)). The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagents, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein (the GPCR of the present invention is expressed in fetal brain, brain, placenta, liver, stomach and kidney (FIG. 1)). Accordingly, methods for treatment include the use of the GPCR protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods.

Antibodies are preferably prepared from regions or discrete fragments of the GPCR proteins. Antibodies can be prepared from any region of the peptide as described herein. However, preferred regions will include those involved in function/activity and/or receptor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition (the GPCR of the present invention is expressed in fetal brain, brain, placenta, liver, stomach and kidney (FIG. 1)). Antibody detection of circulating fragments of the full length protein can be used to identify turnover.

Further, the antibodies can be used to assess expression in disease states such as in active stages of the disease or in an individual with a predisposition toward disease related to the protein's function, particularly in cells and tissues that express the receptor (the GPCR of the present invention is expressed in fetal brain, brain, placenta, liver, stomach and kidney (FIG. 1)). When a disorder is caused by an inappropriate tissue distribution, developmental expression, level of expression of the protein, or expressed/processed form, the antibody can be prepared against the normal protein. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism (the GPCR of the present invention is expressed in fetal brain, brain, placenta, liver, stomach and kidney (FIG. 1)). The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing (the GPCR of the present invention is expressed in fetal brain, brain, placenta, liver, stomach and kidney (FIG. 1)). Thus, where a specific protein has been correlated with expression in a specific tissue, antibodies that are specific for this protein can be used to identify a tissue type.

The antibodies are also useful for inhibiting protein function, for example, blocking the binding of the GPCR peptide to a binding partner such as a ligand. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a GPCR peptide or protein of the present invention (cDNA, transcript and genomic sequence). Such nucleic acid molecules will consist of, consist essentially of, or comprise a nucleotide sequence that encodes one of the GPCR peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule, for example from about 1–300 additional nucleotides.

The present invention further provides nucleic acid molecules that are comprised of the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule is comprised of a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, human genomic sequences (FIG. 3) and cDNA/transcript sequences (FIG. 1), the nucleic acid molecules in the figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the GPCR peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the GPCR proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene (map position was determined to be on chromosome 6 near markers SHGC-1836 (LOD=13.79) and SHGC-12753 (LOD=9.94) (FIG. 3)).

FIG. 3 provides SNP information that has been found in the gene encoding the GPCR protein of the present invention. The following variations were seen: C3440T and C2525T.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C, followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2 (FIG. 3 provides SNP information that has been found in the gene encoding the GPCR protein of the present invention. The following variations were seen: C3440T and C2525T).

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods (map position was determined to be on chromosome 6 near markers SHGC-1836 (LOD=13.79) and SHGC-12753 (LOD=9.94) (FIG. 3)). This is particularly useful in determining whether a particular protein is an allelic variant of one the proteins provided herein The nucleic acid molecules are also useful in making vectors containing the gene regulatory regions of the nucleic acid molecules of the present invention as described in detail below.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form and distribution of nucleic acid expression. Accordingly, the probes can be used to detect the presence of, or to determine levels of, a specific nucleic acid molecule in cells, tissues, and in organisms (the GPCR of the present invention is expressed in fetal brain, brain, placenta, liver, stomach and kidney (FIG. 1)). The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in GPCR protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a GPCR protein, such as by measuring a level of a receptor-encoding nucleic acid in a sample of cells from a subject e.g., mRNA or genomic DNA, or determining if a receptor gene has been mutated (the GPCR of the present invention is expressed in fetal brain, brain, placenta, liver, stomach and kidney (FIG. 1)).

Nucleic acid expression assays are useful for drug screening to identify compounds that modulate GPCR nucleic acid expression, particularly in cells and tissues that express the receptor (the GPCR of the present invention is expressed in fetal brain, brain, placenta, liver, stomach and kidney (FIG. 1)).

The invention thus provides a method for identifying a compound that can be used to treat a disorder associated with nucleic acid expression of the GPCR gene. The method typically includes assaying the ability of the compound to modulate the expression of the GPCR nucleic acid and thus identifying a compound that can be used to treat a disorder characterized by undesired GPCR nucleic acid expression. The assays can be performed in cell-based and cell-free systems. Cell-based assays include cells naturally expressing the GPCR nucleic acid (the GPCR10f the present invention is expressed in fetal brain, brain, placenta, liver, stomach and kidney (FIG. 1)) or recombinant cells genetically engineered to express specific nucleic acid sequences.

The assay for GPCR nucleic acid expression can involve direct assay of nucleic acid levels, such as mRNA levels, or on collateral compounds involved in the signal pathway. Further, the expression of genes that are up or down-regulated in response to the GPCR protein signal pathway can also be assayed. In this embodiment the regulatory regions of these genes can be operably linked to a reporter gene such as luciferase.

Thus, modulators of GPCR gene expression can be identified in a method wherein a cell is contacted with a candidate compound and the expression of mRNA determined. The level of expression of GPCR mRNA in the presence of the candidate compound is compared to the level of expression of GPCR mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate GPCR nucleic acid expression, particularly to modulate activities within a cell or tissue that expresses the proteins (the GPCR of the present invention is expressed in fetal brain, brain, placenta, liver, stomach and kidney (FIG. 1)). Modulation includes both up-regulation (i.e. activation or agonization) or down-regulation (suppression or antagonization) or nucleic acid expression.

Alternatively, a modulator for GPCR nucleic acid expression can be a small molecule or drug identified using the screening assays described herein as long as the drug or small molecule inhibits the GPCR nucleic acid expression in the cells and tissues that express the protein (the GPCR of the present invention is expressed in fetal brain, brain, placenta, liver, stomach and kidney (FIG. 1)).

The nucleic acid molecules are also useful for monitoring the effectiveness of modulating compounds on the expression or activity of the GPCR gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in GPCR nucleic acid, and particularly in qualitative changes that lead to pathology. The nucleic acid molecules can be used to detect mutations in GPCR genes and gene expression products such as mRNA. The nucleic acid molecules can be used as hybridization probes to detect naturally-occurring genetic mutations in the GPCR gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the GPCR gene associated with a dysfunction provides a diagnostic tool for an active disease or susceptibility to disease when the disease results from overexpression, underexpression, or altered expression of a GPCR protein.

Individuals carrying mutations in the GPCR gene can be detected at the nucleic acid level by a variety of techniques (map position was determined to be on chromosome 6 near markers SHGC-1836 (LOD=13.79) and SHGC-12753 (LOD=9.94) (FIG. 3)). Genomic DNA can be analyzed directly or can be amplified by using PCR prior to analysis (FIG. 3 provides SNP information that has been found in the gene encoding the GPCR protein of the present invention. The following variations were seen: C3440T and C2525T). RNA or cDNA can be used in the same way. In some uses, detection of the mutation involves the use of a probe/primer in a polymerase chain reaction (PCR) (see, e.g. U.S. Pat.

Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, (1.7 contacting the nucleic acid sample with one or more primers which specifically hybridize to 19>a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a GPCR gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and SI protection or the chemical cleavage method. Furthermore, sequence differences between a mutant GPCR gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS*85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include, selective oligonucleotide hybridization, selective amplification, and selective primer extension.

The nucleic acid molecules are also useful for testing an individual for a genotype that while not necessarily causing the disease nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the GPCR gene in an individual in order to select an appropriate compound or dosage regimen for treatment. FIG. 3 provides SNP information that has been found in the gene encoding the GPCR protein of the present invention. The following variations were seen: C3440T and C2525T.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control GPCR gene expression in cells, tissues, and organisms. A DNA antisense nucleic acid molecule is designed to be complementary to a region of the gene involved in transcription, preventing transcription and hence production of GPCR protein. An antisense RNA or DNA nucleic acid molecule would hybridize to the mRNA and thus block translation of mRNA into GPCR protein.

Alternatively, a class of antisense molecules can be used to inactivate mRNA in order to decrease expression of GPCR nucleic acid. Accordingly, these molecules can treat a disorder characterized by abnormal or undesired GPCR nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the GPCR protein, such as ligand binding.

The nucleic acid molecules also provide vectors for gene therapy in patients containing cells that are aberrant in GPCR gene expression. Thus, recombinant cells, which include the patient's cells that have been engineered ex vivo and returned to the patient, are introduced into an individual where the cells produce the desired GPCR protein to treat the individual.

The invention also encompasses kits for detecting the presence of a GPCR nucleic acid in a biological sample, particularly cells and tissues that normally express the protein (the GPCR of the present invention is expressed in fetal brain, brain, placenta, liver, stomach and kidney (FIG. 1)). For example, the kit can comprise reagents such as a labeled or labelable nucleic acid or agent capable of detecting GPCR nucleic acid in a biological sample; means for determining the amount of GPCR nucleic acid in the sample; and means for comparing the amount of GPCR nucleic acid in the sample with a standard. The compound or agent can be packaged in a suitable container. The kit can further comprise instructions for using the kit to detect GPCR protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, expression patterns, mutations, variants, or polymorphisms among samples.

Using such arrays, the present invention provides methods to identify the expression of the GPCR proteins/peptides of the present invention and allelic variation within this gene/protein. In detail, such methods comprise incubating a test sample with one or more nucleic acid molecules and assaying for binding of the nucleic acid molecule with components within the test sample. Such assays will typically involve arrays comprising many genes or alleles, at least one of which is a gene and or alleles of the GPCR gene of the present invention (FIG. 3 provides SNP information that has been found in the gene encoding the GPCR protein of the present invention. The following variations were seen: C3440T and C2525T.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the GPCR disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified GPCR genes of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, eg. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:3140 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., Gene Expression Technology: Methods in Enzymology 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd ed, Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as GPCRs, appropriate secretion signals are incorporated into the vector. The signal sequence can be endogenous to the peptides or heterologous to these peptides.

Where the peptide is not secreted into the medium, which is typically the case with GPCRs, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a GPCR protein or peptide that can be further purified to produce desired amounts of GPCR protein or fragments. Thus, host cells containing expression vectors are useful for peptide production.

Host cells are also useful for conducting cell-based assays involving the GPCR protein or GPCR protein fragments, such as those described above as well as other formats known in the art. Thus, a recombinant host cell expressing a native GPCR protein is useful for assaying compounds that stimulate or inhibit GPCR protein function.

Host cells are also useful for identifying GPCR protein mutants in which these functions are affected. If the mutants naturally occur and give rise to a pathology, host cells containing the mutations are useful to assay compounds that have a desired effect on the mutant GPCR protein (for example, stimulating or inhibiting function) which may not be indicated by their effect on the native GPCR protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a GPCR protein and identifying and evaluating modulators of GPCR protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the GPCR protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the GPCR protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, GPCR protein activation, and signal transduction, may not be evident from in vitro cell-free or cell-based assays. Accordingly, it is useful to provide non-human transgenic animals to assay in vivo GPCR protein function, including ligand interaction, the effect of specific mutant GPCR proteins on GPCR protein function and ligand interaction, and the effect of chimeric GPCR proteins. It is also possible to assess the effect of null mutations, that is mutations that substantially or completely eliminate one or more GPCR protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:

(a) a nucleotide sequence that encodes a protein comprising the amino acid sequence of SEQ ID NO: 2;

(b) a nucleotide sequence consisting of the nucleic acid sequence of SEQ ID NO:1; and (c) a nucleotide sequence consisting of the nucleic acid sequence of SEQ ID NO:3.

2. A nucleic acid vector comprising a nucleic acid molecule of claim 1.

3. A host cell containing the vector of claim 2.

4. A method for detecting the presence of a nucleic acid molecule of claim 1 in a sample, said method comprising:

contacting the sample with an oligonucleotide comprising at least 20 contiguous nucleotides that hybridizes to said nucleic acid molecule under stringent conditions, wherein the stringent condition is hybridization in 6× sodium chloride/sodium citrate (SSC) at about 45° C., followed by one or more washes in 0.2×SCC, 0.1% SDS at 50–65° C., and determining whether the oligonucleotide binds to said nucleic acid molecule in the sample.

5. A process for producing a polypeptide comprising culturing the host cell of claim 3 under conditions sufficient for the production of said polypeptide from a nucleic acid molecule that encodes said polypeptide, and recovering said polypeptide from the host cell culture.

6. An isolated polynucleotide consisting of a nucleotide sequence set forth in SEQ ID NO:1.

7. An isolated polynucleotide consisting of a nucleotide sequence set forth in SEQ ID NO:3.

8. A vector according to claim 2, wherein said vector is selected from the group consisting of a plasmid, virus, and bacteriophage.

9. A vector according to claim 2, wherein said isolated nucleic acid molecule is inserted into said vector in proper orientation and correct reading frame such that the protein of SEQ ID NO:2 may be expressed by a cell transformed with said vector.

10. A vector according to claim 9, wherein said isolated nucleic acid molecule is operatively linked to a promoter sequence.

11. An isolated nucleic acid molecule consisting of a nucleotide sequence that is complementary to a nucleotide sequence of claim 1.

* * * * *